(12) United States Patent
Kühn-Wache et al.

(10) Patent No.: US 7,816,325 B2
(45) Date of Patent: Oct. 19, 2010

(54) SECONDARY BINDING SITE OF DIPEPTIDYL PEPTIDASE IV (DP IV)

(75) Inventors: Kerstin Kühn-Wache, Halle/Saale (DE); Joachim Bär, Halle/Saale (DE); Hans-Ulrich Demuth, Halle/Saale (DE); Torsten Hoffmann, Halle/Saale (DE); Ulrich Heiser, Halle/Saale (DE); Wolfgang Brandt, Halle/Saale (DE)

(73) Assignee: OSI Pharmaceuticals, Inc., Ardsley, NY (US)

( * ) Notice: Subject to any disclaimer, the term of this patent is extended or adjusted under 35 U.S.C. 154(b) by 640 days.

(21) Appl. No.: 11/478,217

(22) Filed: Jun. 29, 2006

(65) Prior Publication Data

US 2006/0234940 A1   Oct. 19, 2006

Related U.S. Application Data

(63) Continuation of application No. 10/667,200, filed on Sep. 18, 2003, now abandoned.

(60) Provisional application No. 60/443,417, filed on Jan. 29, 2003.

(51) Int. Cl.
*A61K 38/08* (2006.01)
*A61K 39/395* (2006.01)

(52) U.S. Cl. ................. 514/16; 530/329; 424/146.1

(58) Field of Classification Search .......... None
See application file for complete search history.

(56) References Cited

U.S. PATENT DOCUMENTS 6,376,549 B1 *   4/2002   Fine et al. ............... 514/635

FOREIGN PATENT DOCUMENTS

WO   WO-01/97808   * 12/2001

OTHER PUBLICATIONS

Hinke, 2002, Biochemical and Biophysical research Communications, 291, 1302-1308.*
Wakimasu, 1978, Chem. Pharm. Bull., 26, 1522-1526.*
Kuhn-Wache, 2001, 2nd General meeting of the International Proteolysis Society (IPS), Abstract P. 17, 2 pages.*

* cited by examiner

*Primary Examiner*—Andrew D Kosar
*Assistant Examiner*—Satyanarayana R Gudibande
(74) *Attorney, Agent, or Firm*—Michael J. Rafa; OSI Pharmaceuticals Inc.

(57) ABSTRACT

The present application relates to the secondary binding site of dipeptidyl peptidase IV, its relationship amongst substrates and to the modulation of substrate specificity of dipeptidyl peptidase IV (DP IV, synonym: DPP IV, CD26, EC 3.4.14.5). The application relates further to compounds that bind to the secondary binding site of DP IV and their use to modulate the substrate specificity of DP IV; methods of treatment of various DP IV mediated disorders; and screening methods for the identification of secondary binding sites on DP IV and DP IV-like enzymes.

18 Claims, 43 Drawing Sheets active site of DPIV
docked with Lys-Z-nitro-Pyr

SEQUENCE LISTING

<160> NUMBER OF SEQ ID NOS: 14

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Thr Phe Thr Ser Asp Tyr
1               5

<210> SEQ ID NO 2
<211> LENGTH: 30
<212> TYPE: PRT
<213> ORGANISM: Homo sapiens

<400> SEQUENCE: 2

Tyr Ala Glu Gly Thr Phe Ile Ser Asp Tyr Ser Ile Ala Met Ala Lys
1               5                   10                  15

Ile His Gln Gln Ala Phe Val Asn Trp Leu Leu Ala Gln Lys
            20                  25                  30

<210> SEQ ID NO 3
<211> LENGTH: 6
<212> TYPE: PRT
<213> ORGANISM: Homo sapiens

<400> SEQUENCE: 3

Tyr Ala Glu Gly Thr Phe
1               5

<210> SEQ ID NO 4
<211> LENGTH: 6
<212> TYPE: PRT
<213> ORGANISM: Artificial
<220> FEATURE:
<223> OTHER INFORMATION: synthetic peptide

<400> SEQUENCE: 4

Thr Phe Thr Asp Asp Tyr
1               5

<210> SEQ ID NO 5
<211> LENGTH: 6
<212> TYPE: PRT
<213> ORGANISM: Artificial
<220> FEATURE:
<223> OTHER INFORMATION: synthetic peptide, with C-terminal amide
<220> FEATURE:
<221> NAME/KEY: MOD_RES
<222> LOCATION: (6)..(6)
<223> OTHER INFORMATION: AMIDATION

<400> SEQUENCE: 5

Tyr Ala Glu Ser Thr Phe
1               5

<210> SEQ ID NO 6
<211> LENGTH: 11
<212> TYPE: PRT
<213> ORGANISM: Artificial
<220> FEATURE:
<223> OTHER INFORMATION: synthetic peptide thiazolidine

```
<220> FEATURE:
<221> NAME/KEY: MOD_RES
<222> LOCATION: (11)..(11)

<400> SEQUENCE: 6

Arg Arg Leu Ser Tyr Ser Arg Arg Arg Phe Glu
1               5                   10

<210> SEQ ID NO 7
<211> LENGTH: 27
<212> TYPE: DNA
<213> ORGANISM: Artificial
<220> FEATURE:
<223> OTHER INFORMATION: synthetic probe/primer

<400> SEQUENCE: 7
tcatcgatgc atcatcatca tcatcat                                         27

<210> SEQ ID NO 8
<211> LENGTH: 26
<212> TYPE: DNA
<213> ORGANISM: Artificial
<220> FEATURE:
<223> OTHER INFORMATION: synthetic probe/primer

<400> SEQUENCE: 8
taggtaccgc taaggtaaag agaaac                                          26

<210> SEQ ID NO 9
<211> LENGTH: 38
<212> TYPE: DNA
<213> ORGANISM: Artificial
<220> FEATURE:
<223> OTHER INFORMATION: synthetic probe/primer

<400> SEQUENCE: 9
gacatgggca acacaagaag caatttcttt gcagtggc                             38

<210> SEQ ID NO 10
<211> LENGTH: 38
<212> TYPE: DNA
<213> ORGANISM: Artificial
<220> FEATURE:
<223> OTHER INFORMATION: synthetic probe/primer

<400> SEQUENCE: 10
gccactgcaa agaaattgct tcttgtgttg cccatgtc                             38

<210> SEQ ID NO 11
<211> LENGTH: 37
<212> TYPE: DNA
<213> ORGANISM: Artificial
<220> FEATURE:
<223> OTHER INFORMATION: synthetic probe/primer

<400> SEQUENCE: 11
gcagacactg tcttcgcact gaactgggcc acttacc                              37

<210> SEQ ID NO 12
<211> LENGTH: 37
<212> TYPE: DNA
<213> ORGANISM: Artificial
<220> FEATURE:
<223> OTHER INFORMATION: synthetic probe/primer

<400> SEQUENCE: 12
```

```
ggtaagtggc ccagttcagt gcgaagacag tgtctgc                                37

<210> SEQ ID NO 13
<211> LENGTH: 36
<212> TYPE: DNA
<213> ORGANISM: Artificial
<220> FEATURE:
<223> OTHER INFORMATION: synthetic probe/primer

<400> SEQUENCE: 13
gcaatttggg gctggtcata gcgagggtac gtaacc                                 36

<210> SEQ ID NO 14
<211> LENGTH: 36
<212> TYPE: DNA
<213> ORGANISM: Artificial
<220> FEATURE:
<223> OTHER INFORMATION: synthetic probe/primer

<400> SEQUENCE: 14
ggttacgtac cctcgctatg accagcccca aattgc                                 36
```

SECONDARY BINDING SITE OF DIPEPTIDYL PEPTIDASE IV (DP IV)

CROSS REFERENCE TO RELATED APPLICATIONS

This application is a continuation of U.S. patent application Ser. No. 10/667,200, filed Sep. 18, 2003 now abandoned which claims priority of U.S. patent application Ser. No. 10/246,817, filed Sep. 18, 2002 and also claims priority of U.S. Provisional Patent Application Ser. No. 60/443,417 filed Jan. 29, 2003, all of which are incorporated herein by reference in their entirety.

FIELD OF THE APPLICATION

The present application relates to the secondary binding site of dipeptidyl peptidase IV, its relationship with any type of substrates and to the modulation of substrate specificity of dipeptidyl peptidase IV (DP IV, synonym: DPP IV, CD26, EC 3.4.14.5).

The application relates further to compounds that bind to the secondary binding site of DP IV and their use to modulate the substrate specificity of DP IV.

Furthermore, the present invention provides a method for treating DP IV mediated disorders, selected from but not restricted to, impaired glucose tolerance, glucosuria, lipid disorders, dyslipidemia, hyperlipidaemia, hypertriglyceridemia, hypercholesterolemia, low HDL levels, high LDL levels, metabolic acidosis, hyperglycemia, diabetes mellitus, diabetic neuropathy and nephropathy and of sequelae caused by diabetes mellitus in mammals, metabolism-related hypertension and cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, Syndrome X, ovarian hyperandrogenism (polycystic ovarian syndrome), growth hormone deficiency, neutropenia, tumor metastasis, benign prostatic hypertrophy, gingivitis, osteoporosis, and other conditions, in mammals.

The present application also provides a screening method for the identification of agents, which bind to the secondary binding site of dipeptidyl peptidase IV.

Further on, a screening method for the identification and determination of one or more secondary binding sites of DP IV-like enzymes is provided.

BACKGROUND OF THE INVENTION

The exopeptidase dipeptidyl peptidase IV (DP IV, CD26, EC 3.4.14.5) is involved in a number of physiological regulation processes. On the one hand, DP IV is a peptidase which can change the activity of a number of peptide hormones, neuropeptides and chemokines in a very specific manner (Mentlein, Reg. Pep. 85, pp. 9-24 (1999) while on the other hand the DP IV protein molecule exerts protein-protein interactions, so mediating the regulation of intracellular signaling cascades. A growing number of peptide substrates containing proline, alanine or serine in the penultimate position are identified as substrates of DP IV in vitro and in vivo. Bioactive peptides which are substrates for DP IV and members of such regulation cascades are, among others, NPY, GIP, GLP-1, glucagons, VIP and PACAP. Furthermore, many DP IV-inhibitors belonging to different structural classes are known.

It is known that DP IV-Inhibitors may be useful for the treatment of impaired glucose tolerance and diabetes mellitus (International Patent Application, Publication Number WO 99/61431, Pederson R A et al, Diabetes. 1998 August; 47(8): 1253-8 and Pauly R P et al, Metabolism 1999 March; 48(3): 385-9). In particular WO 99/61431 discloses DP IV-Inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples of low molecular weight dipeptidyl peptidase IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, amino-acyl-borono-prolyl-inhibitors, cyclopropyl-fused pyrrolidines and heterocyclic compounds. Inhibitors of dipeptidyl peptidase IV are described in U.S. Pat. Nos. 6,380,398, 6,011,155; 6,107,317; 6,110,949; 6,124,305; 6,172,081; and WO 95/15309, WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, WO 02/04610, WO 02/051836, WO 02/068420, WO 02/076450; WO 02/083128, WO 02/38541, WO 03/000180, WO 03/000181, WO 03/000250, WO 03/002530, WO 03/002531, WO 03/002553, WO 03/002593, WO 03/004496, WO 03/004498, WO 03/024965, WO 03/024942, WO 03/035067, WO 03/037327, WO 03/035057, WO 03/045977, WO 03/055881, WO 03/68748, WO 03/68757, WO 03/057666, WO 03057144, WO 03/040174 and WO 03/033524, the teachings of which are herein incorporated by reference in their entirety, especially concerning these inhibitors, their definition, uses and their production.

Definitions

The term "active site" as used in the claims and in the description is generally known to a person skilled in the art and means the catalytical site or region of DP IV and/or DP IV-like enzymes, which is responsible for the cleavage or biodegradation of the natural substrates of these enzymes.

The term "secondary binding site" as used in the claims and in the description means a site or region of DP IV and/or DP IV-like enzymes, which is different from the active site, e.g. a) a receptor site or b) a substrate recognition site or c) a regulatory site or allosteric site. The secondary binding site can a) affect the receptor function of DP IV and/or DP IV-like enzymes or b) affect the catalytic activity of DP IV and/or DP IV-like enzymes, especially the selectivity and/or specificity of these enzymes toward their substrates. Some secondary binding sites are complementary to the structure of the substrate of the enzymes, co-enzymes, co-factors and other compounds, which are involved in the activity and function of the enzyme. The enzymes may even have one or more secondary binding sites.

The secondary binding site is an element of the enzyme distinct from the catalytic site with a different form of regulation than the competition between substrates and inhibitors at the catalytic site (Darnell, J., Lodish, H. and Baltimore, D.

1990, Molecular Cell Biology 2$^{nd}$ Edition, Scientific American Books, New York, page 63).

The term "DP IV and/or DP IV-like enzymes" means DP IV or DP IV-like enzymes or both.

The term "activity modifying" as used in the claims and in the description means both the modification of the enzymatic activity as well as the modification of the selectivity or specificity of DP IV and/or DP IV-like enzymes. Especially preferred is the modification of the selectivity or specificity of DP IV and/or DP IV-like enzymes toward their natural substrates.

"Effectors", as that term is used herein, are defined as molecules or ligands that interact with a secondary binding site of DP IV and/or DP IV-like enzymes, thereby changing their catalytical behaviour in vitro and/or in vivo. Effectors can increase or decrease the catalytical activity of the enzymes. Examples of effectors are activators or inhibitors. The effectors as used herein do not act at the active sites of enzymes, but at least one secondary binding site, e.g. a regulatory site, or an allosteric site. The term "effectors" is used herein synonymously with "agent" or "compound".

The term "DP IV-inhibitor" is generally known to a person skilled in the art and means enzyme inhibitors, which interact with the active site or catalytical site of DP IV or DP IV-like enzymes or DP IV and/or DP IV-like enzymes and inhibit the catalytical activity of these enzymes.

The "use of effectors" encompasses one single effector or two or more effectors together. Preferred is the use of two effectors. Especially preferred is the use of one single effector.

"Conditions associated with diabetes mellitus" itself include hyperglycaemia, insulin resistance, including acquired insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance and gestational diabetes.

"Complications associated with diabetes mellitus" includes renal disease, especially renal disease associated with Type 2 diabetes, neuropathy and retinopathy.

Renal diseases associated with Type 2 diabetes include nephropathy, glomerulonephritis, glomerular sclerosis, nephrotic syndrome, hypertensive nephrosclerosis and end stage renal disease.

Diabetes mellitus is preferably Type 2 diabetes.

Classification of Diabetes

Clinical diabetes may be divided into four general subclasses, including (1) type 1 (caused by beta cell destruction and characterized by absolute insulin deficiency) (2) type 2 (characterized by insulin resistance and relative insulin deficiency) (3) other specific types of diabetes (associated with various identifiable clinical conditions or syndromes) and (4) gestational diabetes mellitus. In addition to these clinical categories, two conditions—impaired glucose tolerance and impaired fasting glucose—refer to a metabolic state intermediate between normal glucose homeostasis and overt diabetes. These conditions significantly increase the later risk of diabetes mellitus and may in some instances be part of its natural history. It should be noted that patients with any form of diabetes might require insulin treatment at some point. For this reason the previously used terms insulin-dependent diabetes (for type 1 diabetes mellitus) and non-insulin-dependent diabetes (for type 2) have been eliminated.

Diabetes is currently classified as follows:

Clinical Diabetes
1. Type 1 diabetes, formerly called insulin-dependent diabetes mellitus (IDDM) or "juvenile-onset diabetes"
2. Type 2 diabetes, formerly called non-insulin-dependent diabetes (NIDDM) or "adult-onset diabetes"
3. Other specific types
   a) Genetic defects of β-cell function (e.g., maturity-onset diabetes of the young [MODY] types 1-3 and point mutations in mitochondrial DNA)
   b) Genetic defects in insulin action
   c) Disease of the exocrine pancreas (e.g., pancreatitis, trauma, pancreatectomy, neoplasia, cystic fibrosis, hemochromatosis, fibrocalculous pancreatopathy).
   d) Endocrinopathies (e.g. acromegaly, Cusing's syndrome, hyperthyroidism, pheochromocytoma, glucagonoma, somatostinoma, aldosteronoma)
   e) Drug or chemical induced (e.g., glucocorticosteroids, thiazides, diazoxide, pentamidine, vacor, thyroid hormone, phenytoin [Dilantin], β-agonists, oral contraceptives)
   f) Infections (e.g., congenital rubella, cytomegalovirus)
   g) Uncommon forms of immune-mediated diabetes (e.g., "stiff-man", syndrome, anti-insulin receptor antibodies)
   h) Other genetic syndromes (e.g., Down, Klinefelter's, Turner's syndrome, Huntington's disease, myotonic dystrophy, lipodystrophy, ataxia-telangiectasia)
4. Gestational diabetes mellitus Risk Categories
1. Impaired fasting glucose
2. Impaired glucose tolerance Type 1 Diabetes Mellitus Patients with this disorder have little or no insulin secretory capacity and depend on exogenous insulin to prevent metabolic decompensation (e.g., ketoacidosis) and death.

Commonly but not always, diabetes appears abruptly (i.e., over days and weeks) in previously healthy non-obese children or young adults; in older age groups it may have a more gradual onset. At the time of initial evaluation the typical patient often appears ill, has marked symptoms (e.g., polyuria, polydipsia, polyhagia, and weight loss), and may demonstrate ketoacidosis. Type 1 diabetes is believed to have a long a symptomatic preclinical stage often lasting years, during which pancreatic beta cells are gradually destroyed by an autoimmune attack that is influenced by HLA and other genetic factors, as well as the environment. Initially, insulin therapy is essential to restore metabolism toward normal. However, a so-called honeymoon period may follow and last weeks or moths, during which time smaller doses of insulin are required because of partial recovery of beta cell function and reversal of insulin resistance caused by acute illness. Thereafter, insulin secretory capacity is gradually lost (over several years). The association of type 1 diabetes with specific immune response (HLA) genes and the presence of antibodies to islet cells and their constituents provides strong support for the theory that type 1 diabetes is an autoimmune disease. This syndrome accounts for lees than 10% of diabetes in United States.

Type 2 Diabetes Mellitus

Type 2, by far the most common form of the disease, is found in over 90% of the diabetic patient population. These patients retain a significant level of endogenous insulin secretory capacity. However, insulin levels are low relative to the magnitude of insulin resistance and ambient glucose levels.

Type 2 patients are not dependent on insulin for immediate survival and ketosis rarely develops, except under conditions of great physical stress. Nevertheless, these patients may require insulin therapy to control hyperglycemia. Type 2 diabetes typically appears after the age of 40 years, has a high rate of genetic penetrance unrelated to HLA genes, and is associated with obesity. The clinical features of type 2 diabetes may be mild (fatigue, weakness, dizziness, blurred vision, or other non-specific complaints may dominate the picture) or may be tolerated for many years before the patient seeks medical attention. Moreover, if the level of hyperglycemia is insufficient to produce symptoms, the disease may become evident only after complications develop.

Other Specific Types of Diabetes

This category encompasses a variety of diabetic syndromes attributed to a specific disease, drug, or condition. Genetic research has provided new insights into pathogenesis of MODY, which was formerly included as a form of type 2 diabetes. MODY encompasses several genetic defects of beta cell function, among which mutations at several genetic loci on different chromosomes have been identified. The most common forms—MODY type 3—is associated with a mutation for a transcription factor encoded on chromosome 12 named hepatocyte nuclear 1α (HNF 1, also known as TCF1) and -MODY type 2 is associated with mutations of the glucokinase gene (on chromosome 7) Mutations of the HNF-4α gene (on chromosome 20) are responsible for type 1 of MODY. Each of these conditions is inherited in an autosomal dominant pattern. Two new rare forms of MODY are associated with mutations of the HNF-1β (on chromosome 17) and an insulin gene transcription factor termed PDX-1 or 1DX-1 (on chromosome 13).

The distinction between the various subclasses of diabetes mellitus is usually made on clinical grounds. However, a small subgroup of patients are difficult to classify, that is, they display features common to both type 1 and 2 diabetes. Such patients are commonly non-obese and have reduced insulin secretory capacity that is not sufficient to make them ketosis prone. Many initially respond to oral agents but, with time, require insulin. Some appear to have a slowly evolving form of type 1 diabetes, whereas others defy easy categorization.

Gestational Diabetes

The term gestational diabetes describes women with impaired glucose tolerance that appears or is first detected during pregnancy. Gestational diabetes usually appears in the $2^{nd}$ or $3^{rd}$ trimester, a time when pregnancy-associated insulin antagonistic hormones peak. After delivery, glucose tolerance generally (but not always) reverts to normal.

Diagnosis

The diagnosis of diabetes is usually straightforward when the classic symptoms of polyuria, polydipsia, and weight loss are present. All that is required is a random plasma glucose measurement from venous blood that is 200 mg/dL or greater. If diabetes is suspected but not confirmed by a random glucose determination, the screening test of choice is overnight fasting plasma glucose level. The diagnosis is established if fasting is equal to or greater than 126 mg/dL on at least two separate occasions.

Related Conditions

Impaired Glucose Tolerance and Impaired Fasting Glucose

Impaired glucose tolerance (IGT) and impaired fasting glucose (IFG) are terms applied to individuals who have glucose levels that are higher than normal, (under fed or fasting conditions, respectively) but lower than those accepted as diagnostic for diabetes mellitus. Both conditions are associated with an increased risk for cardiovascular disease, but do not produce the classic symptoms or the microvascular and neuropathic complications associated with diabetes mellitus. In a subgroup of patients (about 25 to 30%), however, type 2 diabetes eventually develops.

Impaired Glucose Metabolism

Impaired Glucose Metabolism (IGM) is defined by blood glucose levels that are above the normal range but are high enough to meet the diagnostic criteria for type 2 diabetes mellitus. The incidence of IGM varies from country to country, but usually occurs 2-3 time more frequently than overt diabetes. Until recently, individuals with IGM were felt to be pre-diabetics, but data from several epidemiological studies argue that subjects with IGM are heterogeneous with respect to their risk of diabetes and their risk of cardiovascular morbidity and mortality. The data suggest that subjects with IGM, in particular, those with impaired glucose tolerance (IGT), do not always develop diabetes, but whether they are diabetic or not, they are, nonetheless, at high risk for cardiovascular morbidity and mortality. Among subjects with I GM, about 58% have Impaired Glucose tolerance (IGT), another 29% have impaired fasting glucose (IFG), and 13% have both abnormalities (IFG/IGT). As discussed above, IGT is characterized by elevated post-prandial (post-meal) hyperglycemia while IFG has been defined by the ADA (American Diabetes Association) on the basis of fasting glycemic values.

The categories of (a) normal glucose tolerance (NGT), (b) impaired glucose metabolism (IGM) and (c) overt type 2 diabetes mellitus are periodically revised and adopted by the Expert Committee of the American Diabetes Association (ADA). The actual values as defined in "Report of the Expert Committee on the Diagnosis and Classification of Diabetes Mellitus. Diabetes Care (26) 1, 2003, 5-20" and "The Diabetes Ready-Reference Guide for Health Care Professionals, 2000, published by the American Diabetes Association" are:
  a) Normal Glucose Tolerance (NGT)=fasting glucose level <6.1 mmol/L or less than 110 mg/dl and a 2h post-prandial glucose level of <7.8 mmol/L or <140 mg/dl.
  b) Impaired Glucose Metabolism (IGM) is impaired fasting glucose (IFG) defined as IFG=fasting glucose level of 6.1-7.0 mmol/L or 110-126 mg/dl and/or impaired glucose tolerance (IGT)=a 2 h post-prandial glucose level (75 g OGTT) of 7.8-11.1 mmol/L or 140-200 mg/dl).
  c) Type 2 diabetes=fasting glucose of greater than 7 mmol/L or 126 mg/dl or a 2 h post-prandial glucose level (75 g OGTT) of greater than 11.1 mmol/L or 200 mg/dl.

These criteria were defined using the WHO recommended conditions for administration of an oral glucose tolerance test (75 g O GTT) i. e., the oral administration of a glucose load containing the equivalent of 75 g of anhydrous glucose dissolved in water with a blood sample taken 2 hours later to analyze to post-prandial glucose. Other OGTT test conditions have confirmed the associated risks of the IGT and IFG categories including: 1) using 50 g glucose instead of 75 g, 2) using a casual (non-fasting) glucose sample as the analyte, and 3) analysing the post-prandial glucose at 1 hour rather than 2 hours post-glucose load. Under all of these conditions, the glycemic categories defined above have been linked to the increased risks described below, but the standardized OGTT is preferred in order to minimize variations in test results.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "pharmaceutically acceptable" embraces both human and veterinary use: for example the term "pharmaceutically acceptable" embraces a veterinarily acceptable compound or a compound acceptable in human medicine a health care.

Throughout the description and the claims the expression "acyl" can denote a C1-20 acyl residue, preferably a C1-8 acyl residue and especially preferred a C1-4 acyl residue; "cycloalkyl" can denote a C3-12 cycloalkyl residue, preferably a C4, C5 or C6 cycloalkyl residue; and "carbocyclic" can denote a C3-12 carbocyclic residue, preferably a C4, C5 or C6 carbocyclic residue. "Heteroaryl" is defined as an aryl residue, wherein 1 to 4, and more preferably 1, 2 or 3 ring atoms are replaced by heteroatoms like N, S or O. "Heterocyclic" is defined as a cycloalkyl residue, wherein 1, 2 or 3 ring atoms are replaced by heteroatoms like N, S or O. "Peptides" are selected from dipeptides to decapeptides, preferred are dipeptides, tripeptides, tetrapeptides and pentapeptides. The amino acids for the formation of the "peptides" can be selected from those listed above.

Throughout the description and the claims the expression "alkyl" can denote a $C_{1-50}$ alkyl group, preferably a $C_{6-30}$ alkyl group, especially a $C_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-10}$ alkynyl group, preferably a $C_{2-6}$ alkynyl group, which has the triple bond(s) at any desired location and may be substituted or unsubstituted; the expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the afore-mentioned substituents may in turn have one or more (but preferably zero) alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae $(alkyl)_2N-$ or alkyl-NH—, —CO—N(alkyl)$_2$ or —CO—NH(alkyl), -alkyl-OH or -alkyl-COOH.

SUMMARY OF THE INVENTION

The inventors of the present application unexpectedly show, that the biodegradation of different substrates, which bind to the same catalytic domain of DP IV and/or DP IV-like enzymes, can be modulated in an unexpected very specific manner.

The invention provides a method to identify the site in the DP IV protein or in DP IV-like enzymes or in both, DP IV and DP IV-like enzymes which is responsible for the modulation of the substrate specificity of DP IV and also provides new compounds, which regulate the substrate specificity of DP IV and which are useful for the treatment of, for example, impaired glucose tolerance, glucosuria, lipid disorders, dyslipidemia, hyperlipidaemia, hypertriglyceridemia, hypercholesterolemia, low HDL levels, high LDL levels, metabolic acidosis, hyperglycemia, diabetes mellitus, diabetic neuropathy and nephropathy and of sequelae caused by diabetes mellitus in mammals, metabolism-related hypertension and cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, Syndrome X, ovarian hyperandrogenism (polycystic ovarian syndrome), growth hormone deficiency, neutropenia, tumor metastasis, benign prostatic hypertrophy, gingivitis, osteoporosis, and other conditions, in mammals.

Other Potential target diseases and the actual stage of research are summarized in table 1.

TABLE 1

Target diseases for DP IV-inhibition

| Target disease | Development stage | Comments |
|---|---|---|
| AIDS | cell culture | mechanism not fully understood |
| Autoimmune diseases | cell culture and animal models | high doses necessary |
| Rheumatoid Arthritis | animal models | |
| Multiple sclerosis | animal experiments | |
| Psoriasis | cell culture and animal experiments | |
| Graft rejection | animal experiments | |
| Wound healing | | |
| Anxiety | effective in animal models | |
| Diabetes type II | Phase II studies | |
| Cancer | cell culture, animal models | DP IV and FAP are involved |
| Obesity | animal experiments | NPY, GLP-1 and orexine mediated |

The problem of the invention is solved by using a prolyl oligopeptidase (POP) based computer-generated model of DP IV and of the crystal structure of DP IV for the identification of secondary binding sites of DP IV and by providing specific compounds, which bind to at least one secondary binding site and are able to modify very differently and/or specifically the DP IV-catalyzed truncation of substrates of DP IV and DP IV-like enzymes, e.g. bioactive peptides. The overall result is a significant increase of substrate dependent DP IV-selectivity by such compounds and thereby minimization of side reactions with other substrates and as such of potential side effects after complete inhibition of DP IV-activity.

BRIEF DESCRIPTION OF THE DRAWINGS

Further understanding of these and other aspects of the instant invention may be had by reference to the figures wherein.

Figure 1:
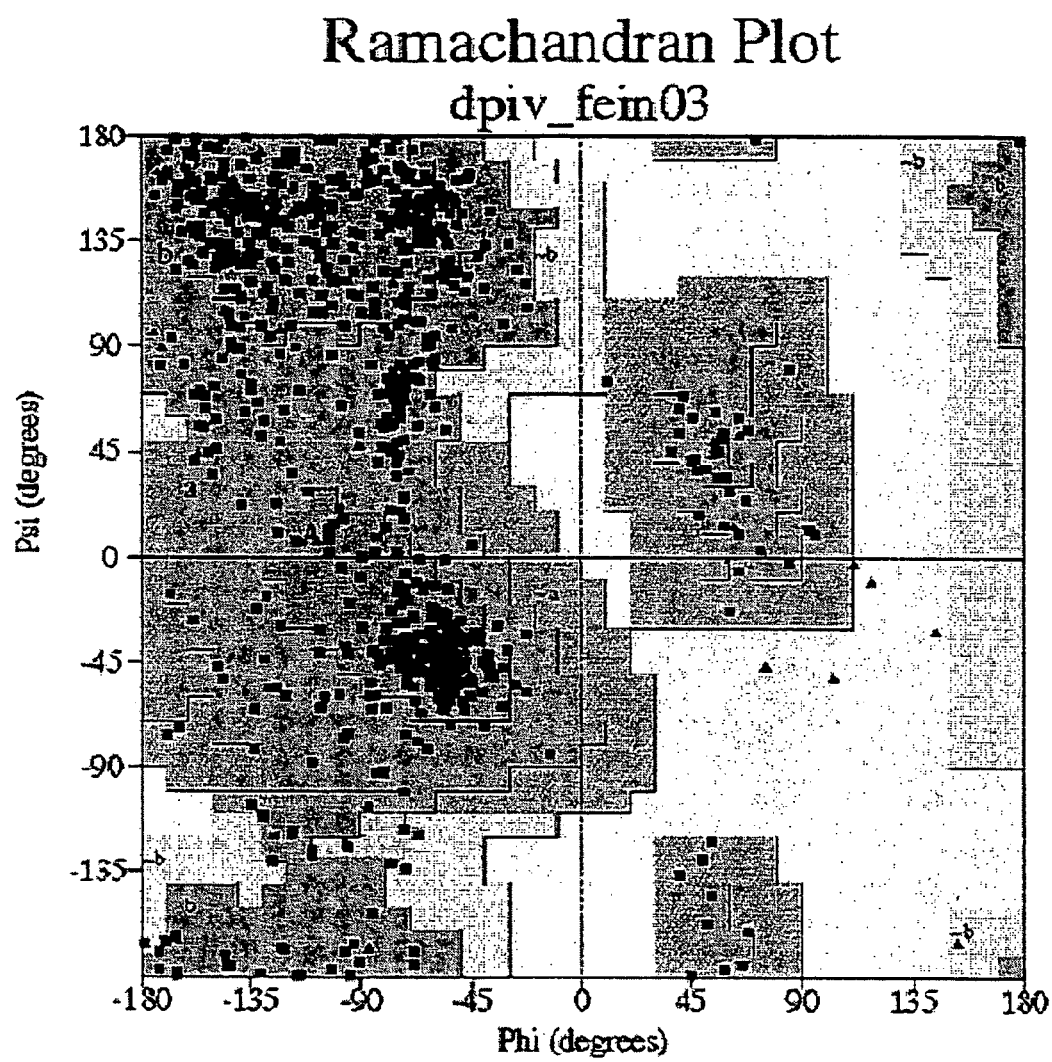
FIG. 1 shows a plot of the distribution of the backbone dihedral angles of the complete model of human DP IV. There are no residues in disallowed regions, but some residues are located in only generously allowed areas. Most of them represent residues in loops at the surface of the propeller domain.
Figure 2A:
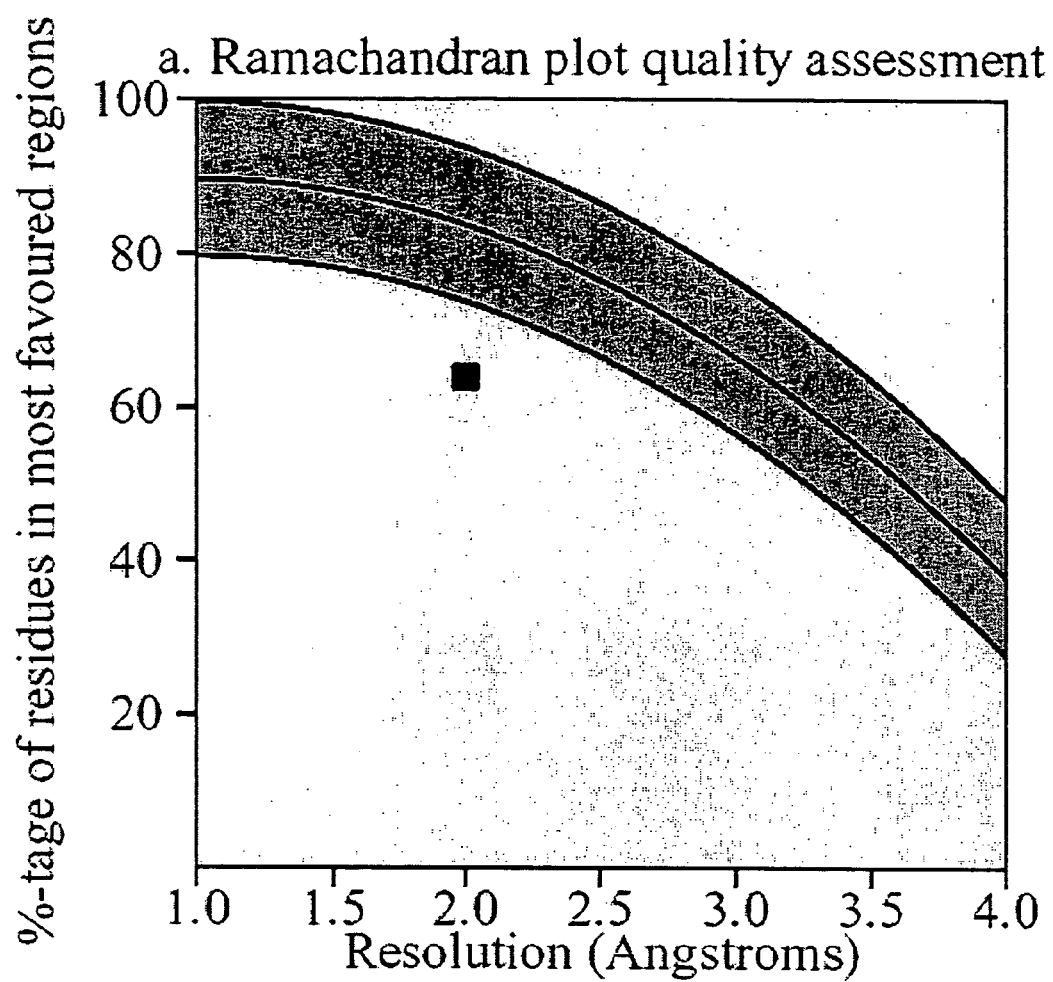
Figure 2B:
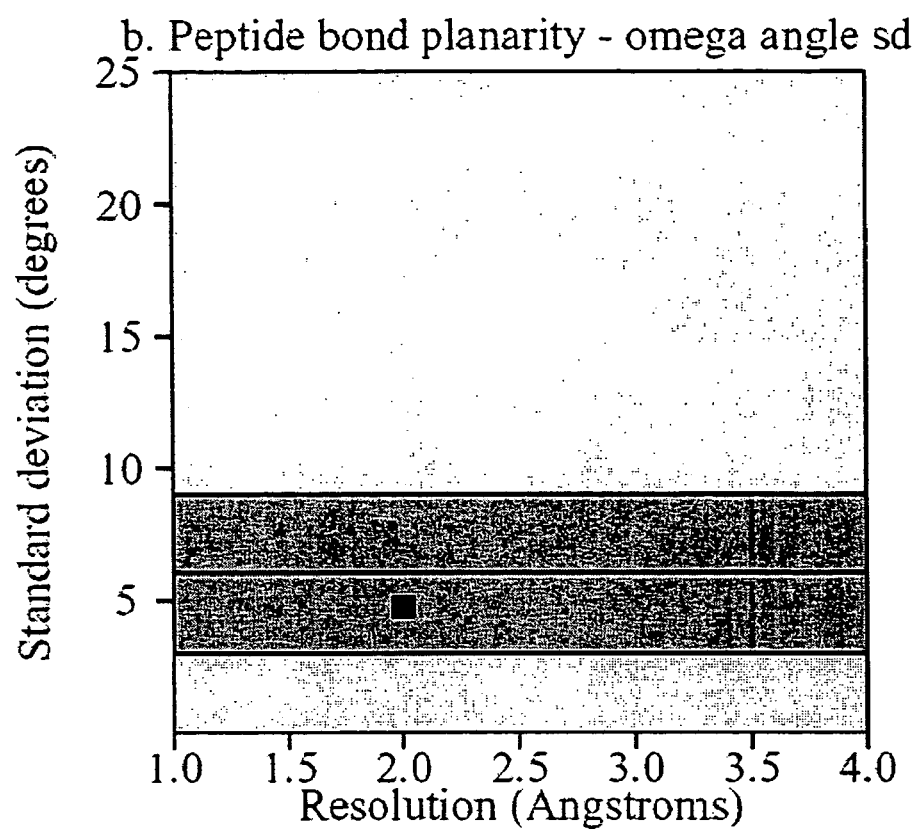
Figure 2C:
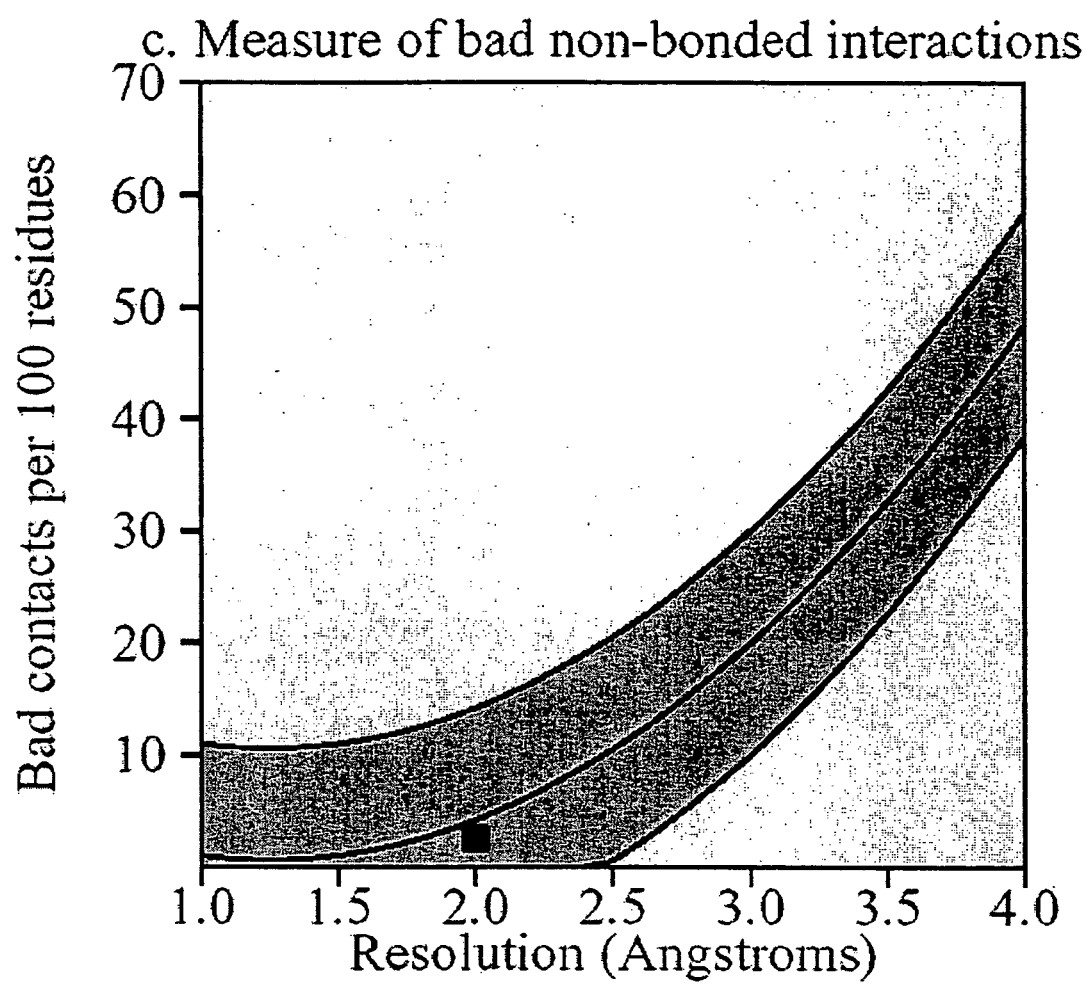
Figure 2D:
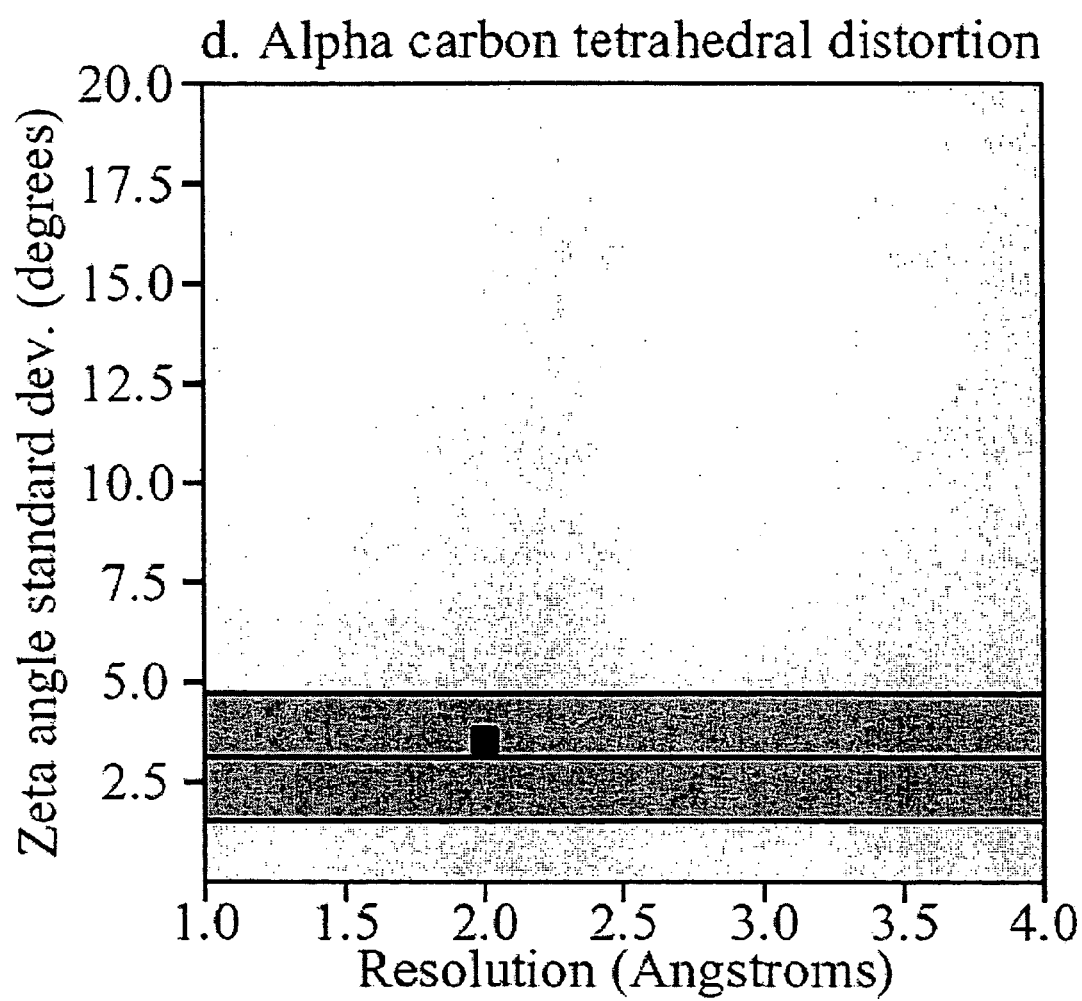
Figure 2E:
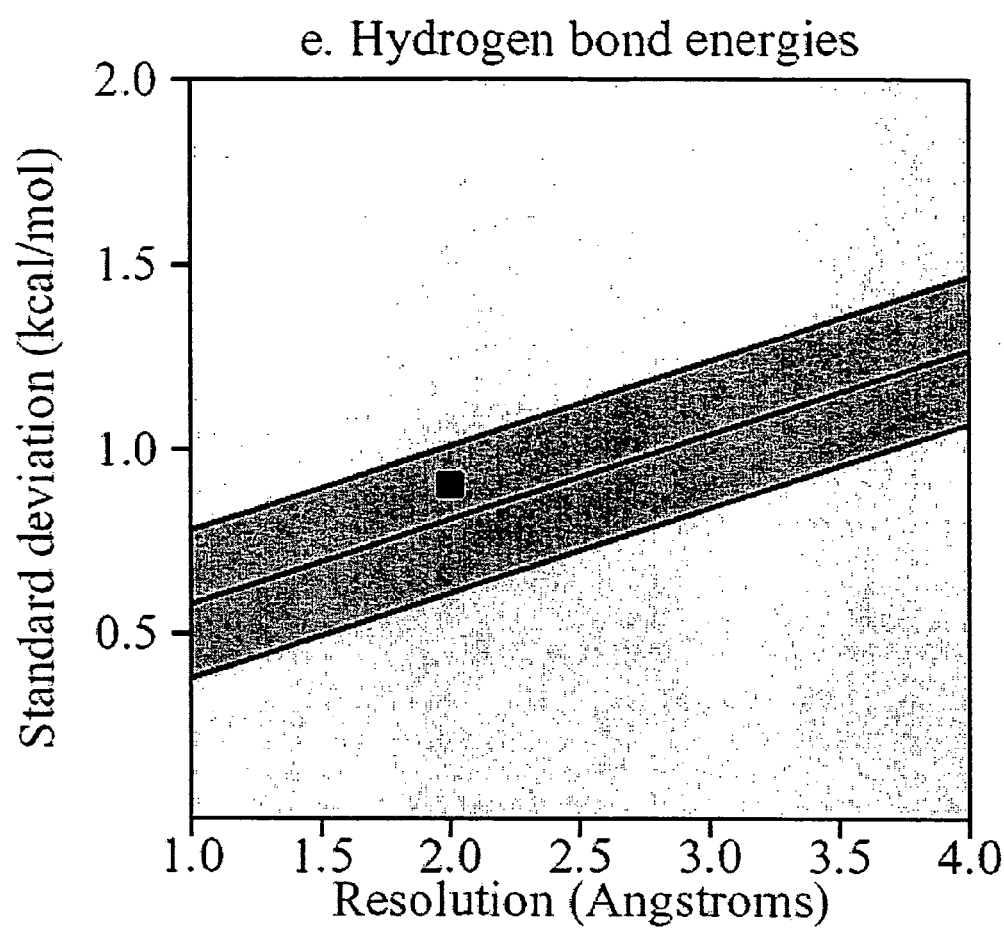
Figure 2F:
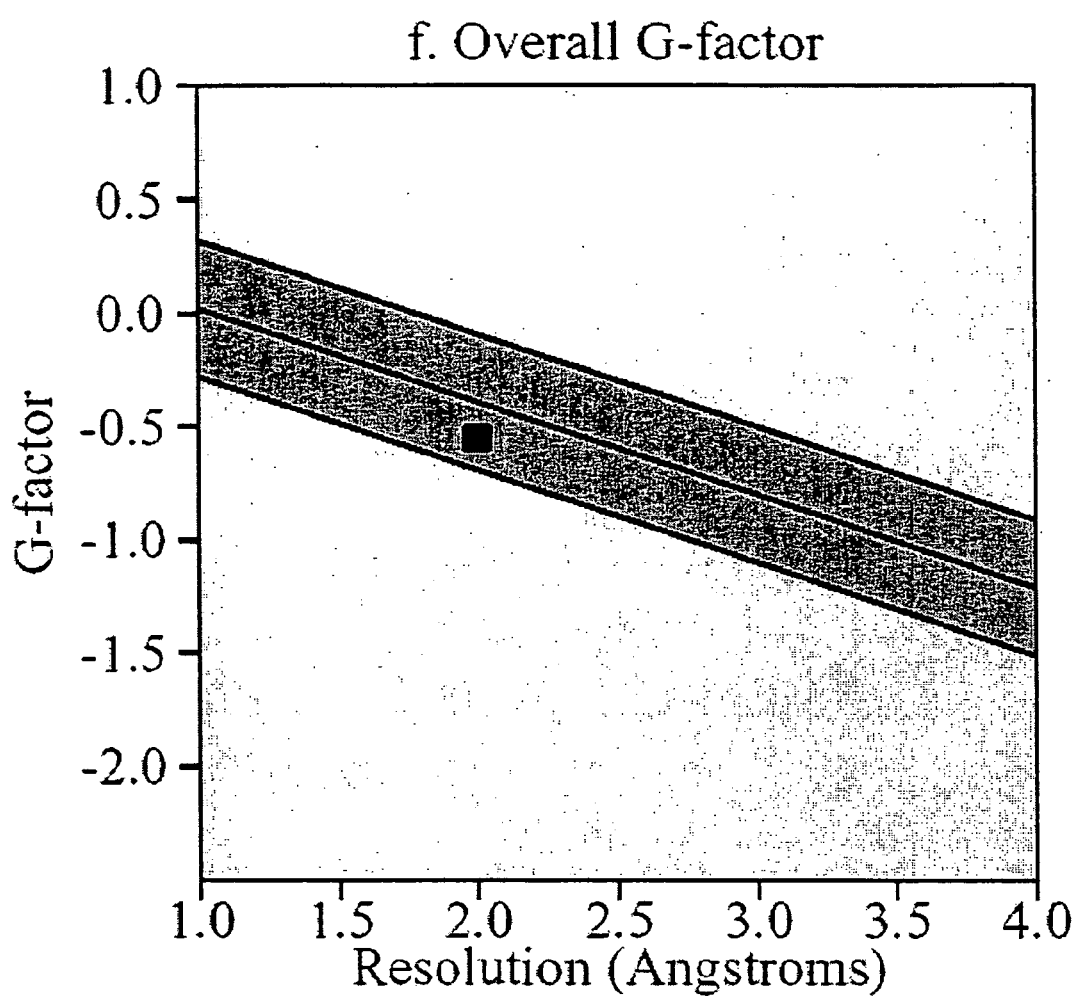

The plot statistics is a measure for the plot quality. The plot statistics for FIG. 1 is as follows:

| | | |
|---|---|---|
| Residues in most favoured regions | 435 | 62.8% |
| Residues in additionally allowed regions | 226 | 32.6% |
| Residues in generously allowed regions | 32 | 4.6% |
| Residues in disallowed regions | 0 | 0.0% |
| Number of non-glycine and non-proline residues | 693 | 100.0% |
| Number of end-residues (excl. Gly and Pro) | 1 | |
| Number of glycine residues (shown as triangles) | 43 | |
| Number of proline residues | 29 | |
| Total number of residues | 766 | |

FIG. 2 shows the analysis of the quality of the model of human DP IV with regard to some essential stereo-chemical parameters. The plot statistics is as follows:

| Stereochemical parameter | No. of data points | Parameter value | Comparison Values | | No. of band widths from mean | |
|---|---|---|---|---|---|---|
| | | | Typical value | Band width | | |
| a. %-tage residues in A, B, L | 693 | 63.9 | 83.8 | 10.0 | −2.0 | WORSE |
| b. Omega angle standard deviation | 765 | 4.7 | 6.0 | 3.0 | −0.4 | Inside |
| c. Bad contacts/100 residues | 19 | 2.5 | 4.2 | 10.0 | −0.2 | Inside |
| d. Zeta angle standard deviation | 723 | 3.5 | 3.1 | 1.6 | 0.3 | Inside |
| e. H-bond energy standard deviation | 389 | 0.9 | 0.8 | 0.2 | 0.5 | Inside |
| f. Overall G-factor | 766 | −0.6 | −0.4 | 0.3 | −0.5 | Inside |

Figure 3:
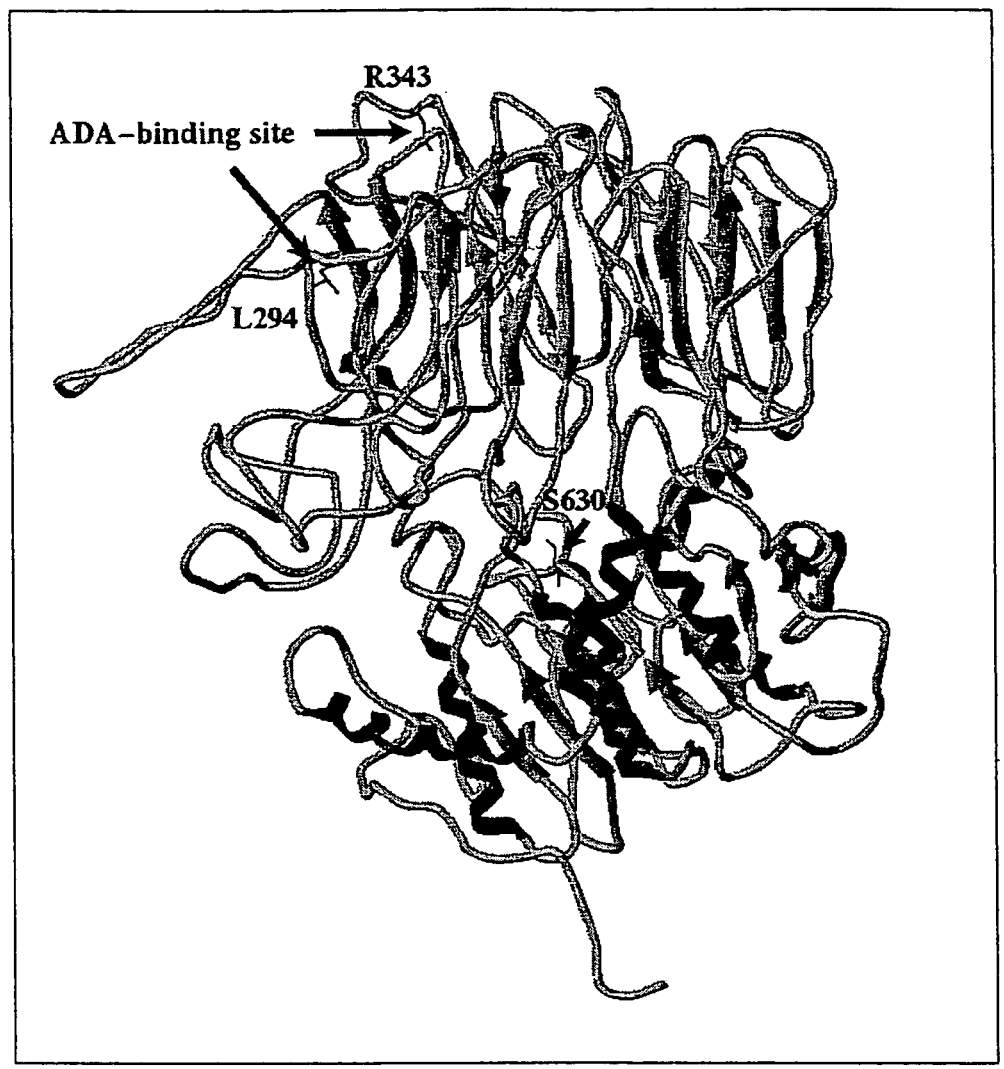
Figure 4:
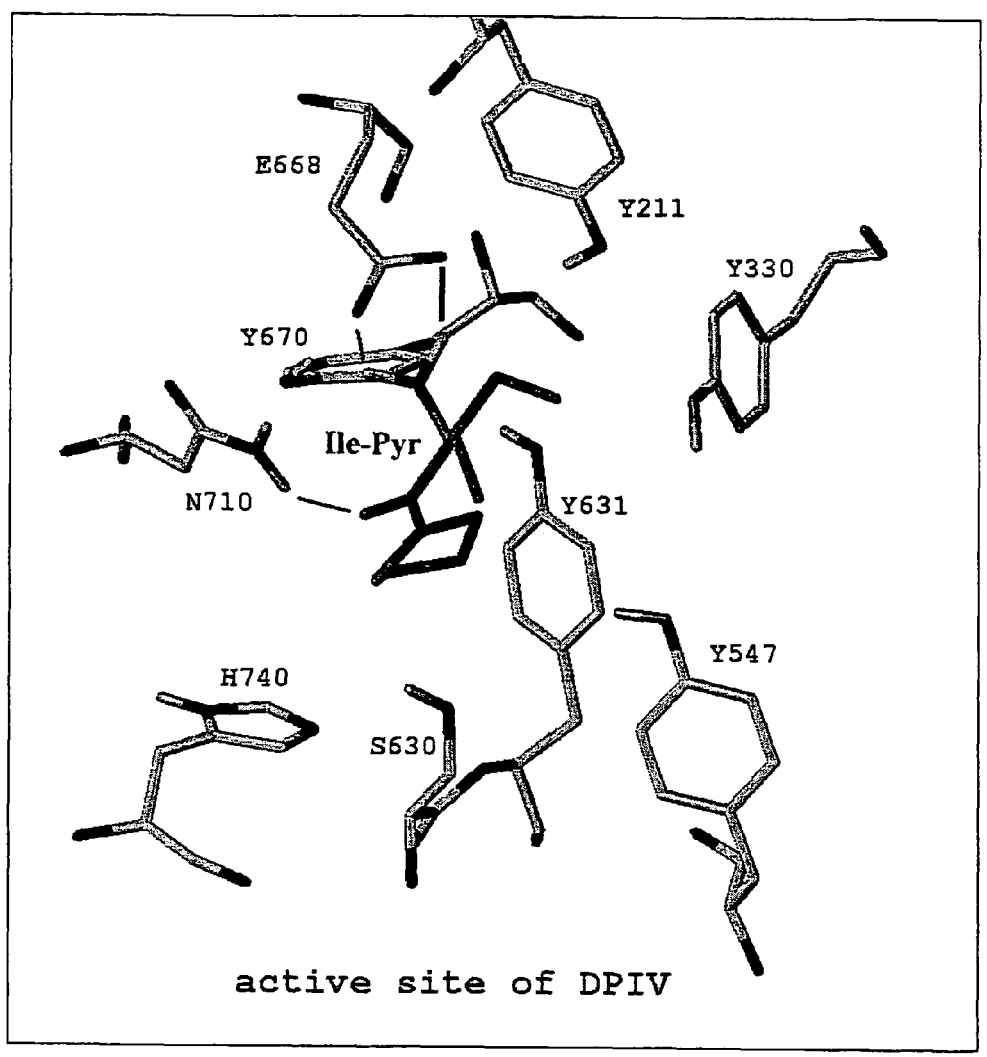
Figure 5:
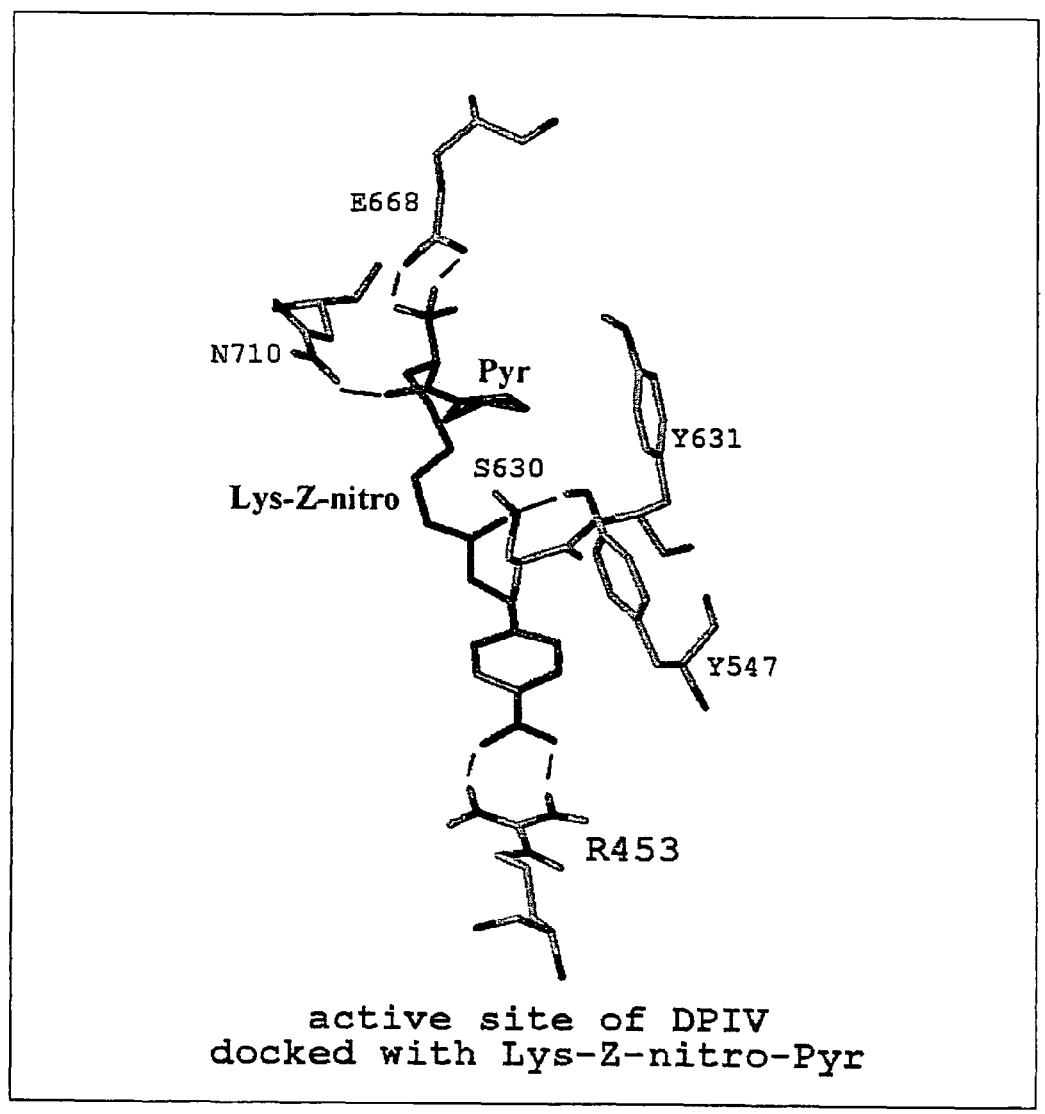
Figure 6:
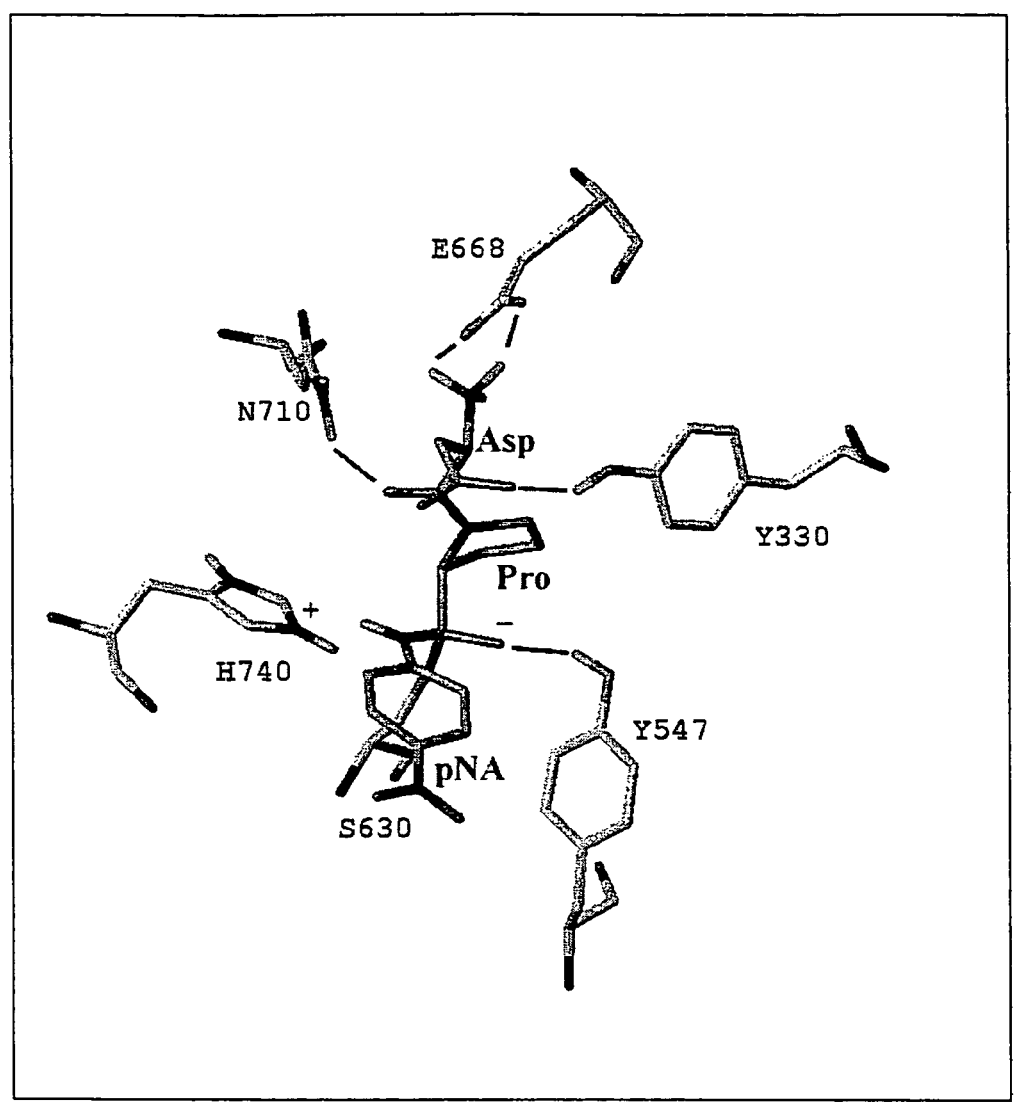
Figure 7:
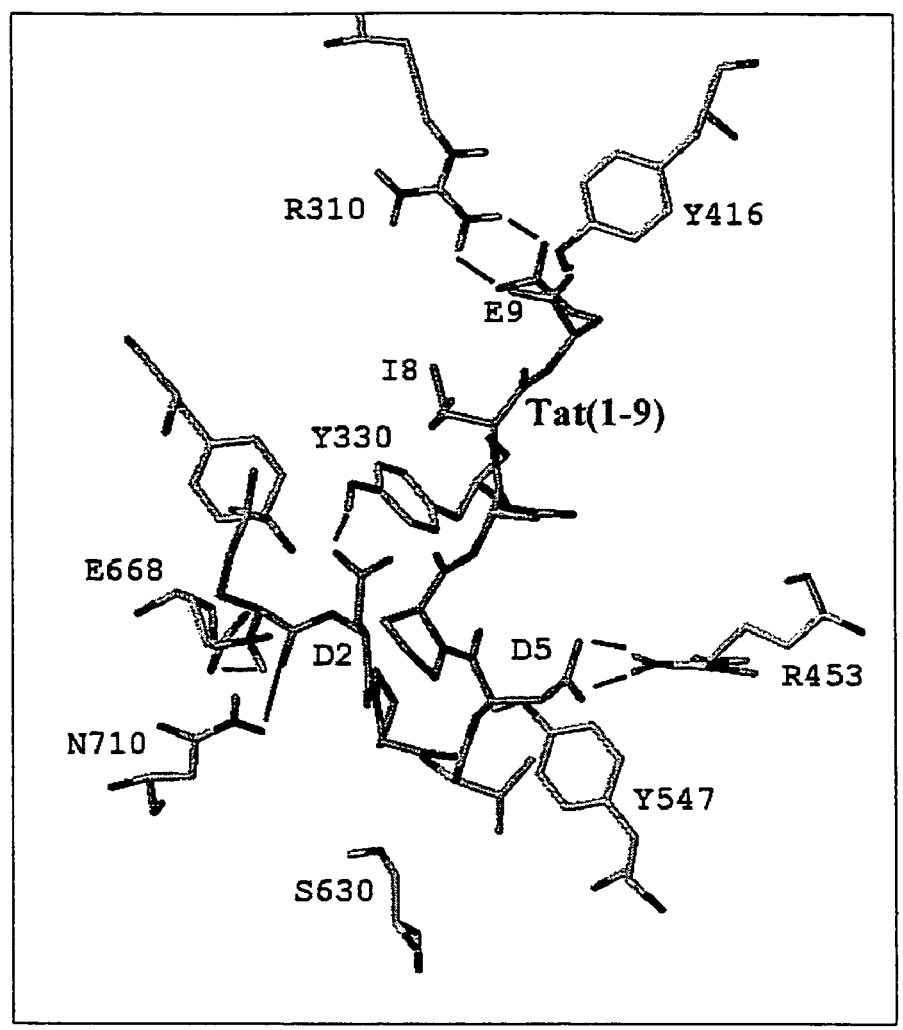
Figure 8:
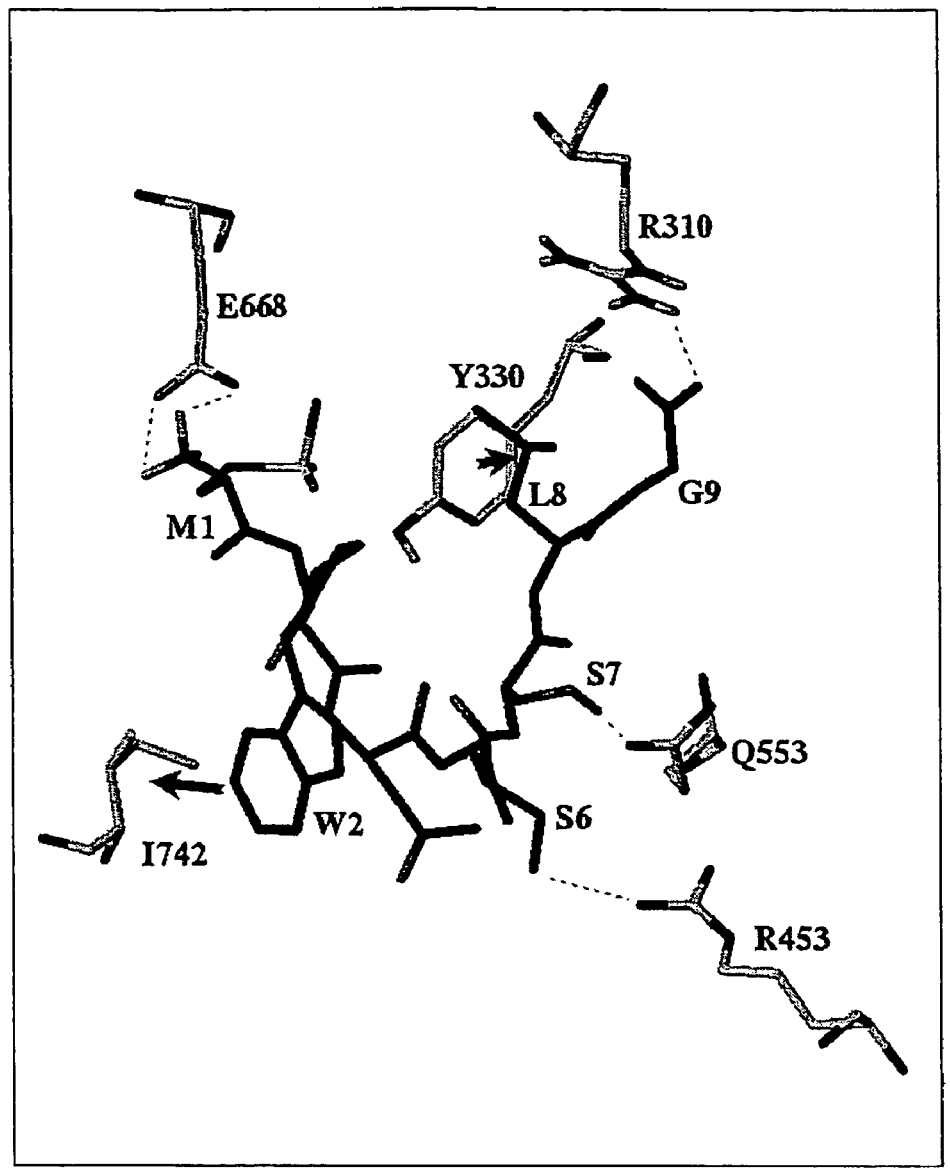
Figure 9:
Figure 10:
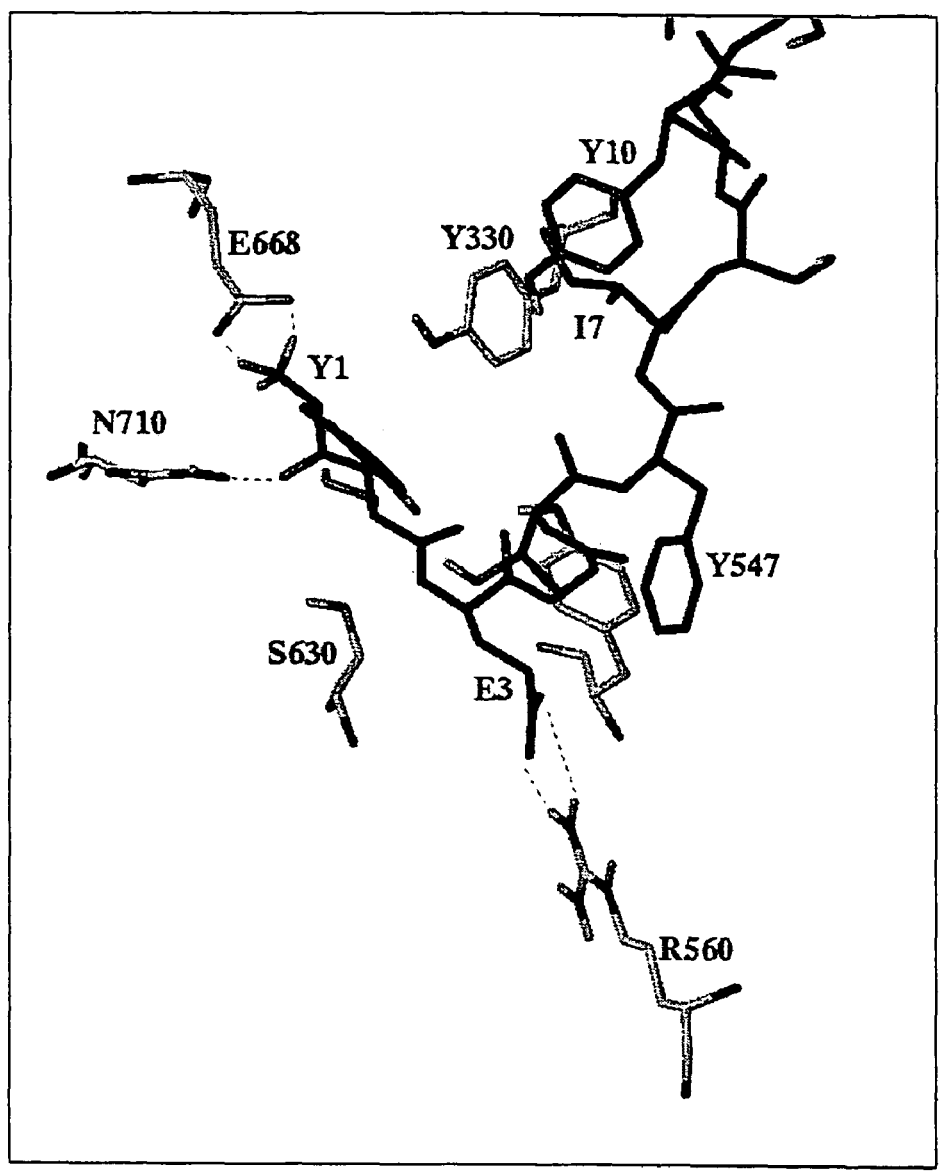
Figure 11:
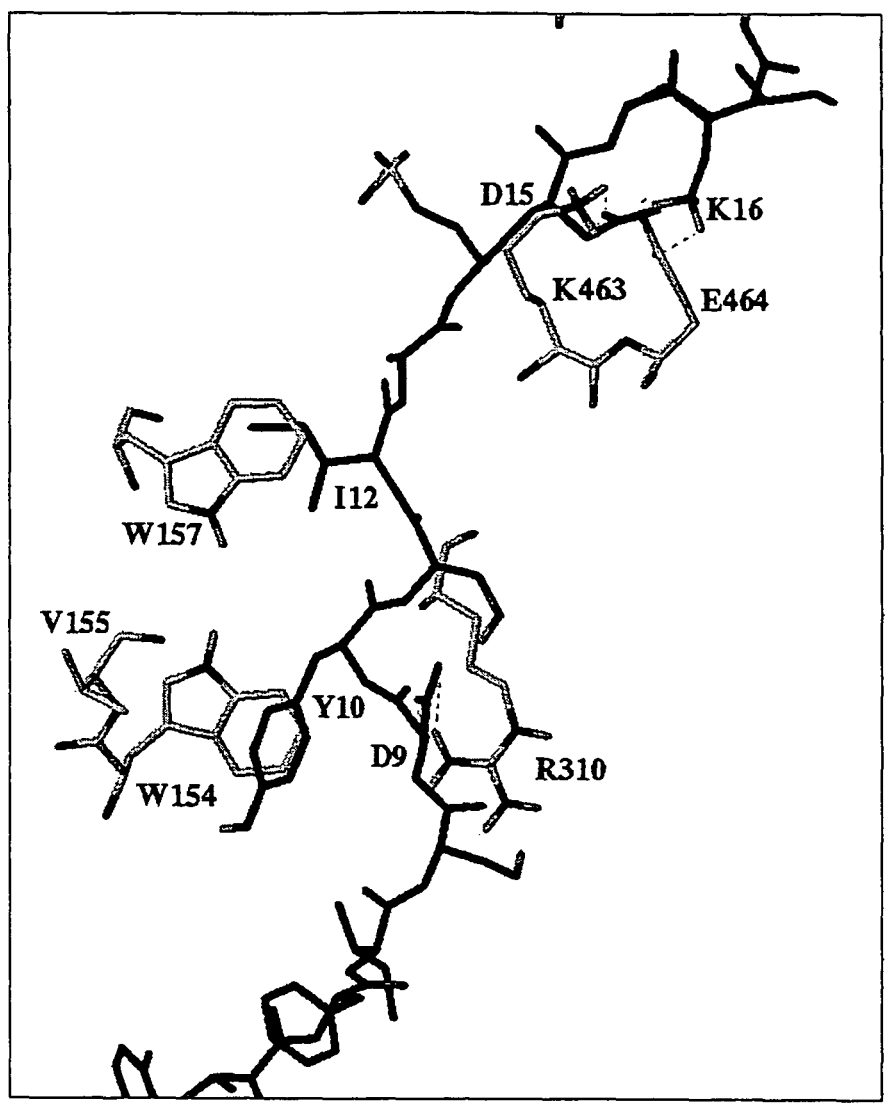
Figure 12:
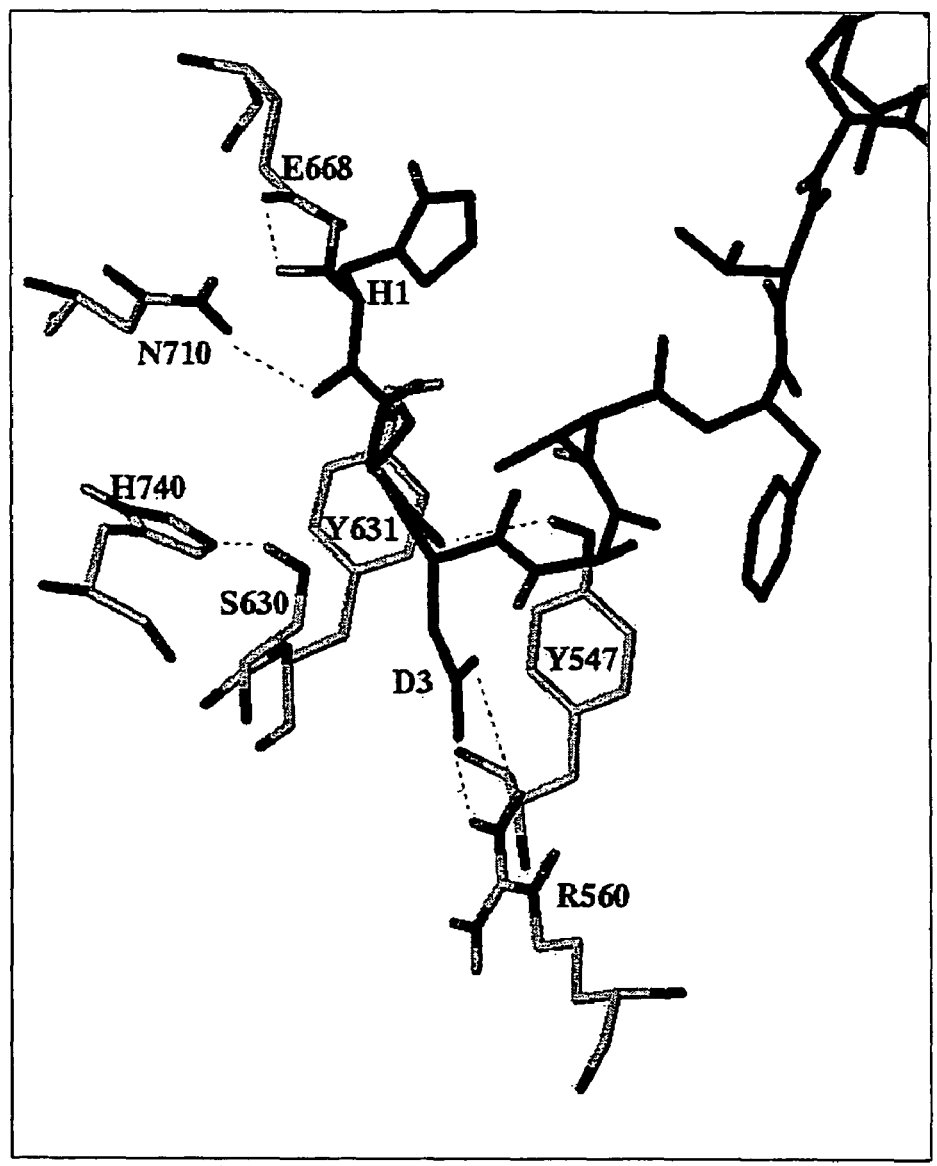
Figure 13:
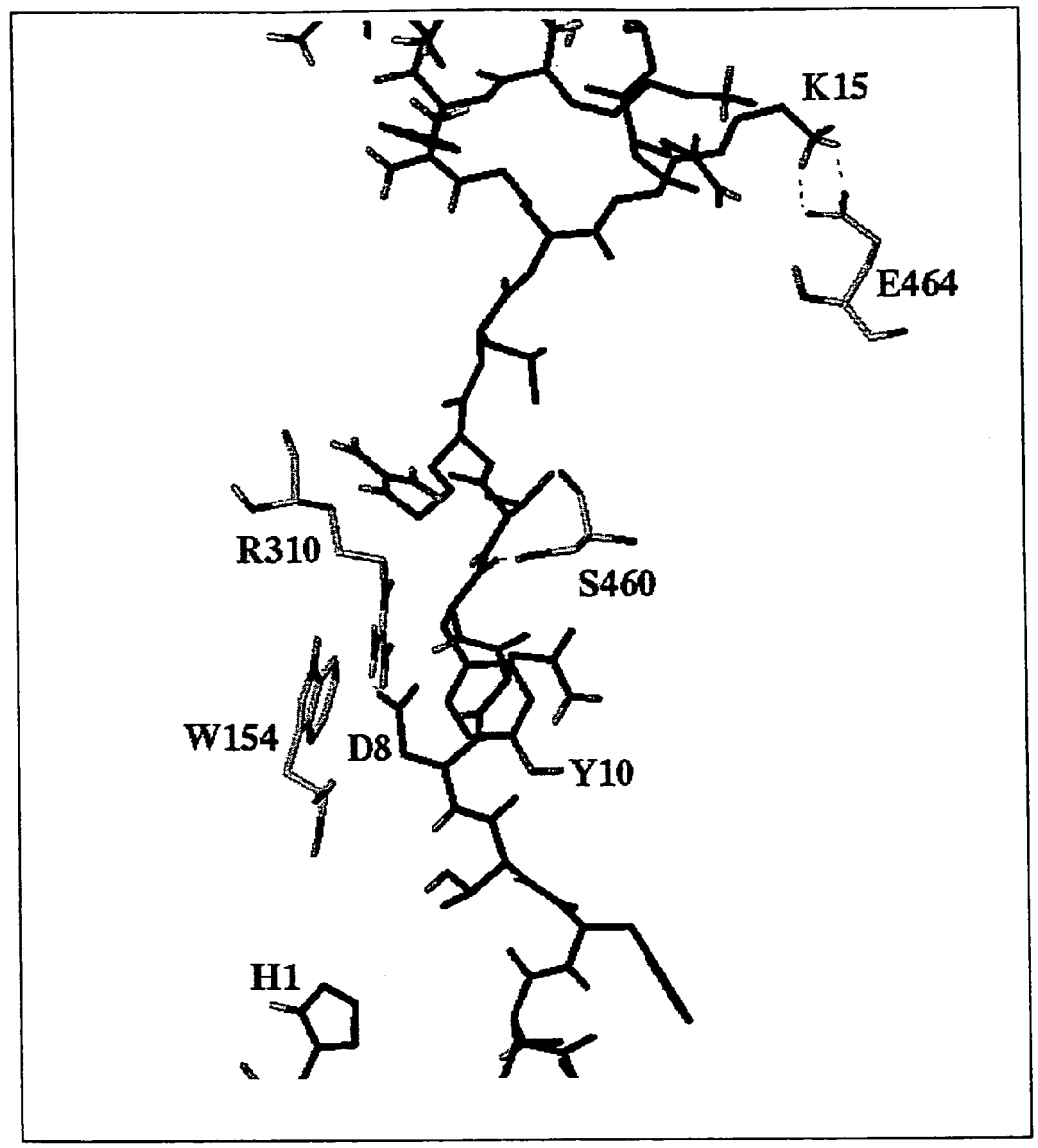
Figure 14:
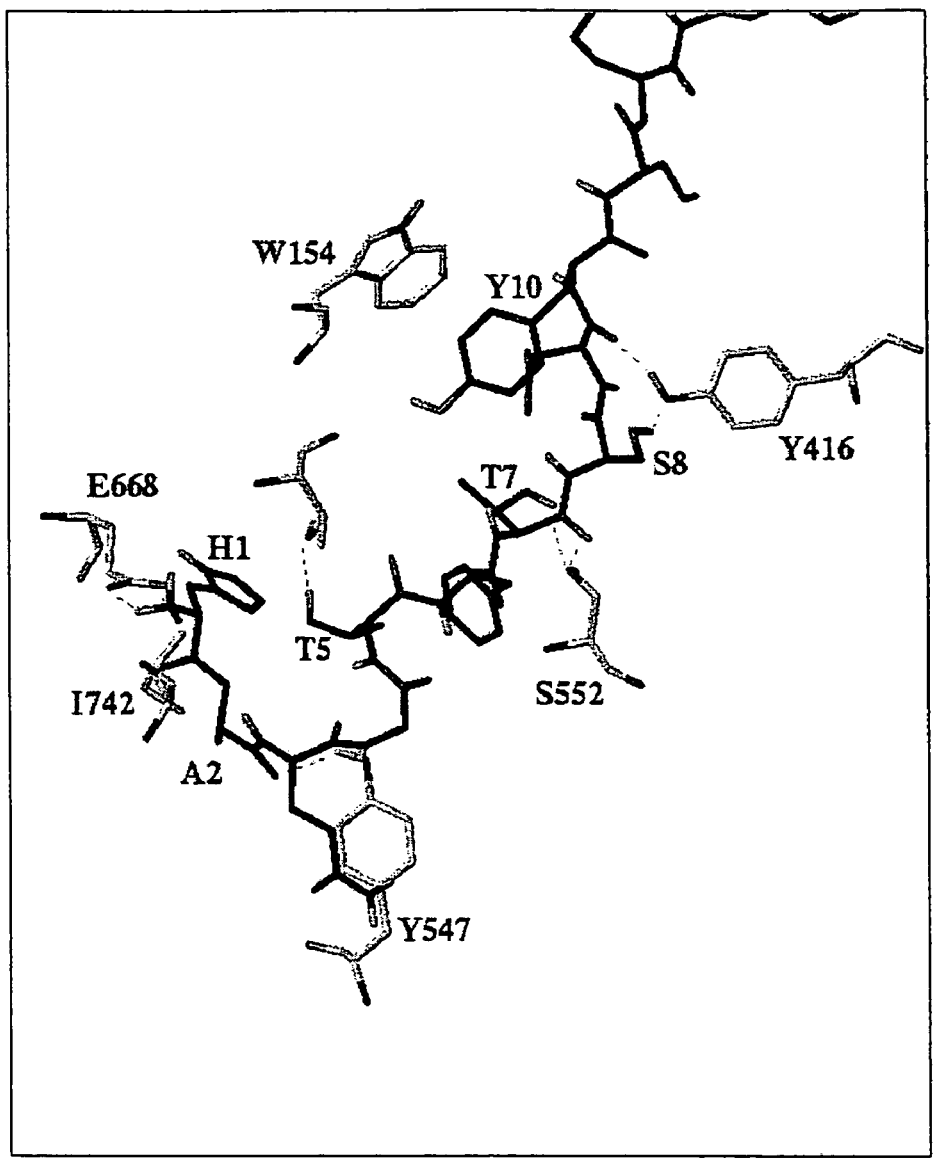
Figure 15:
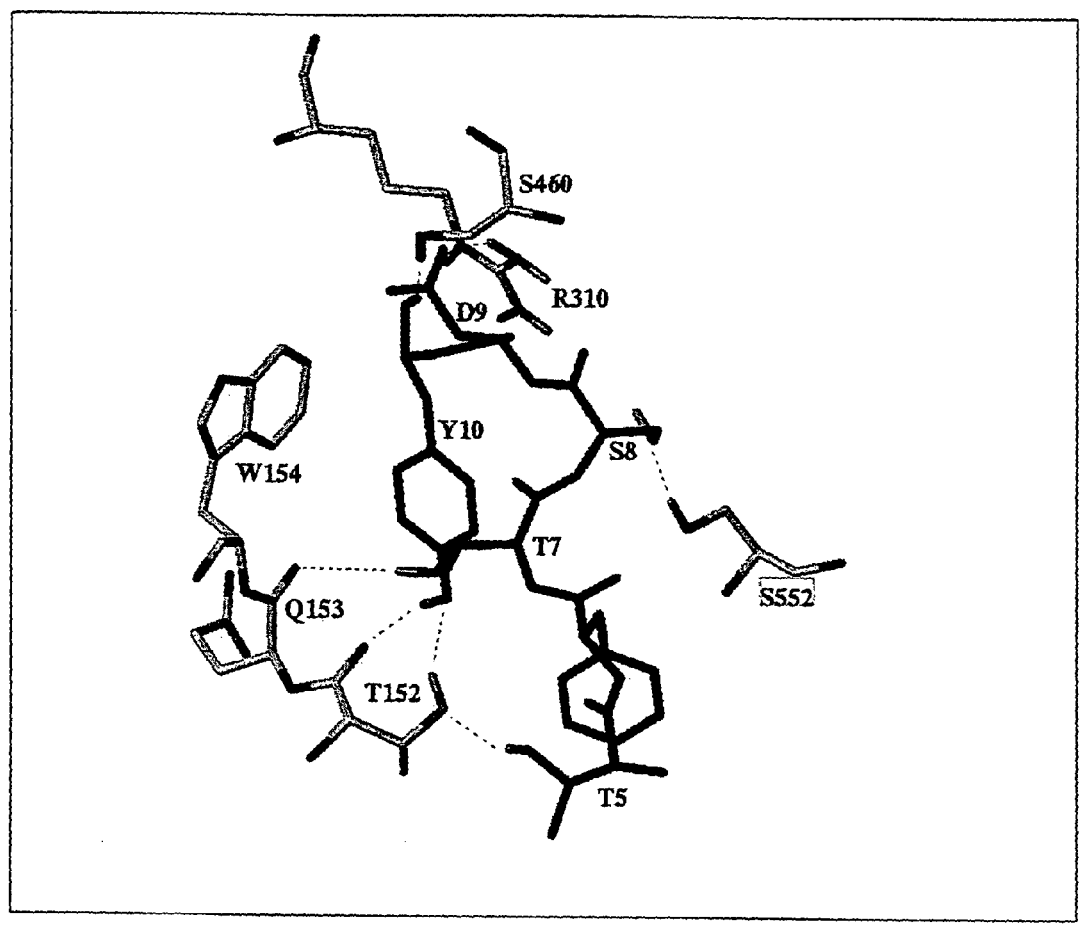
Figure 16:
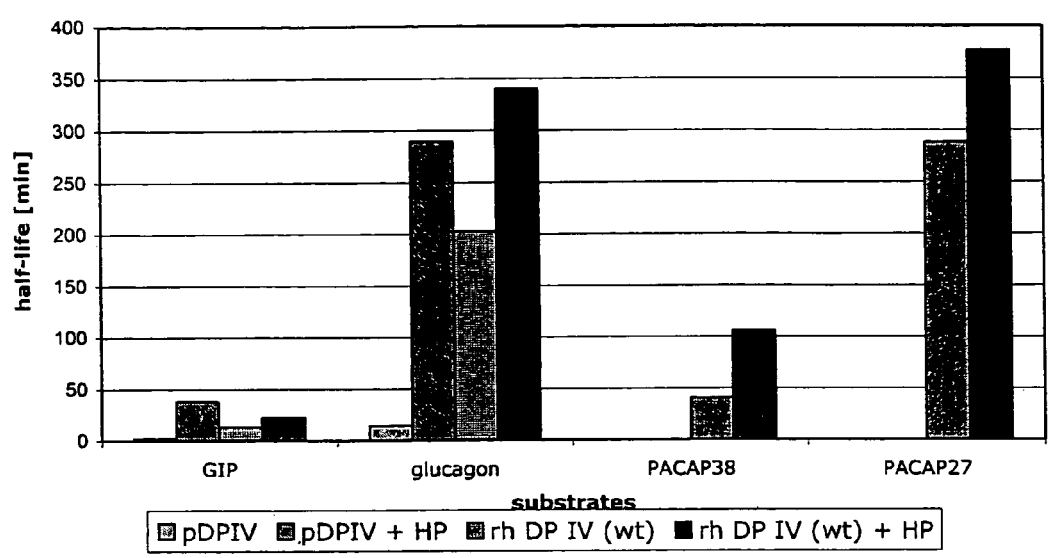
Figure 17:
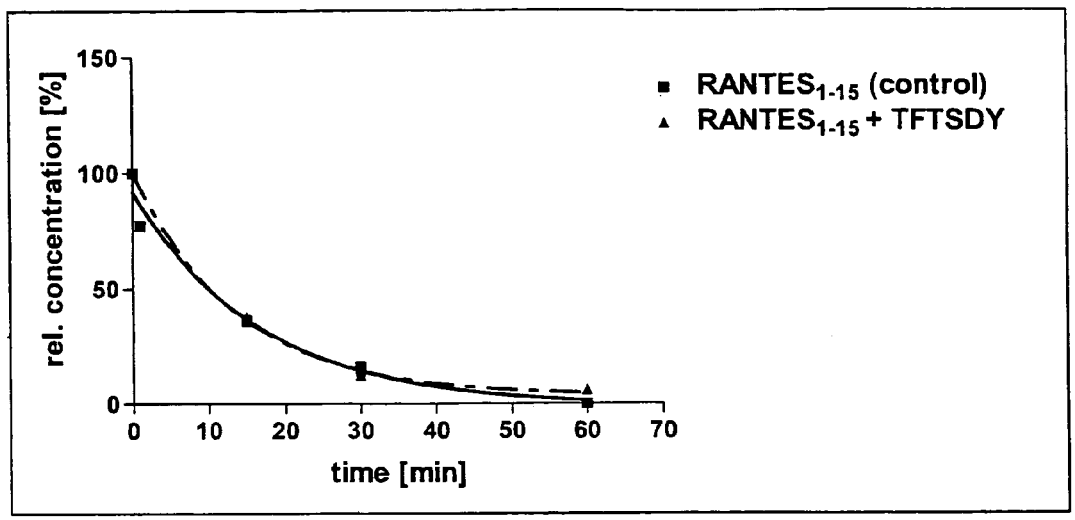
Figure 18:
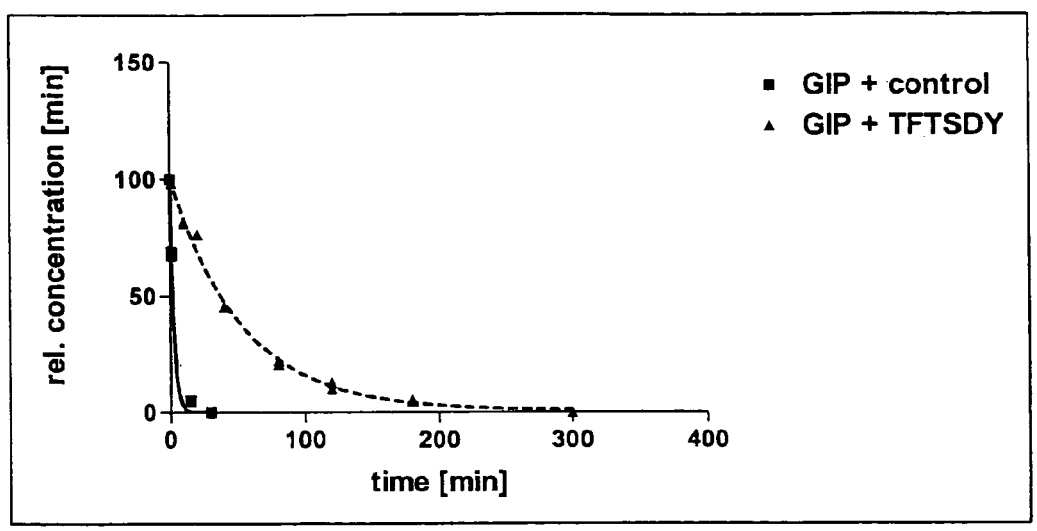
Figure 19:
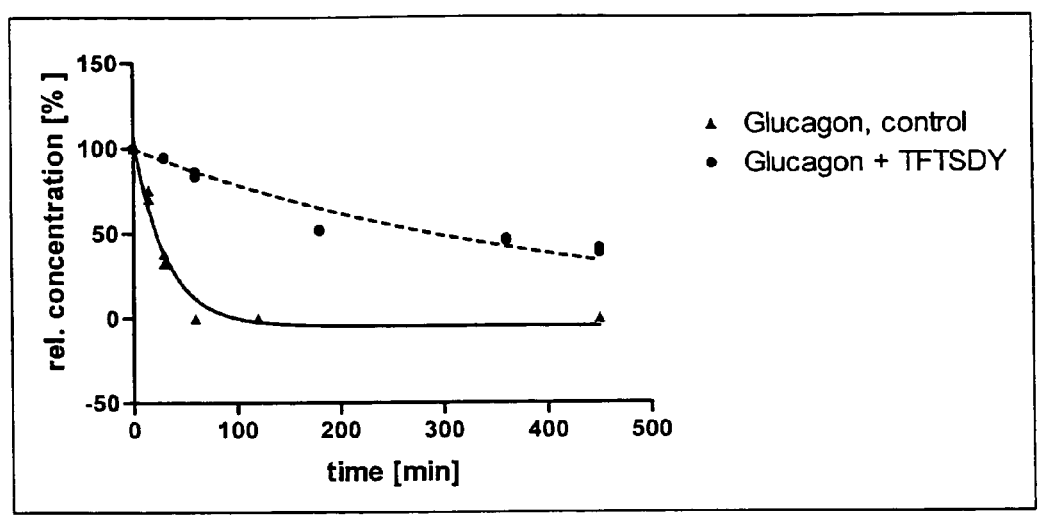
Figure 20:
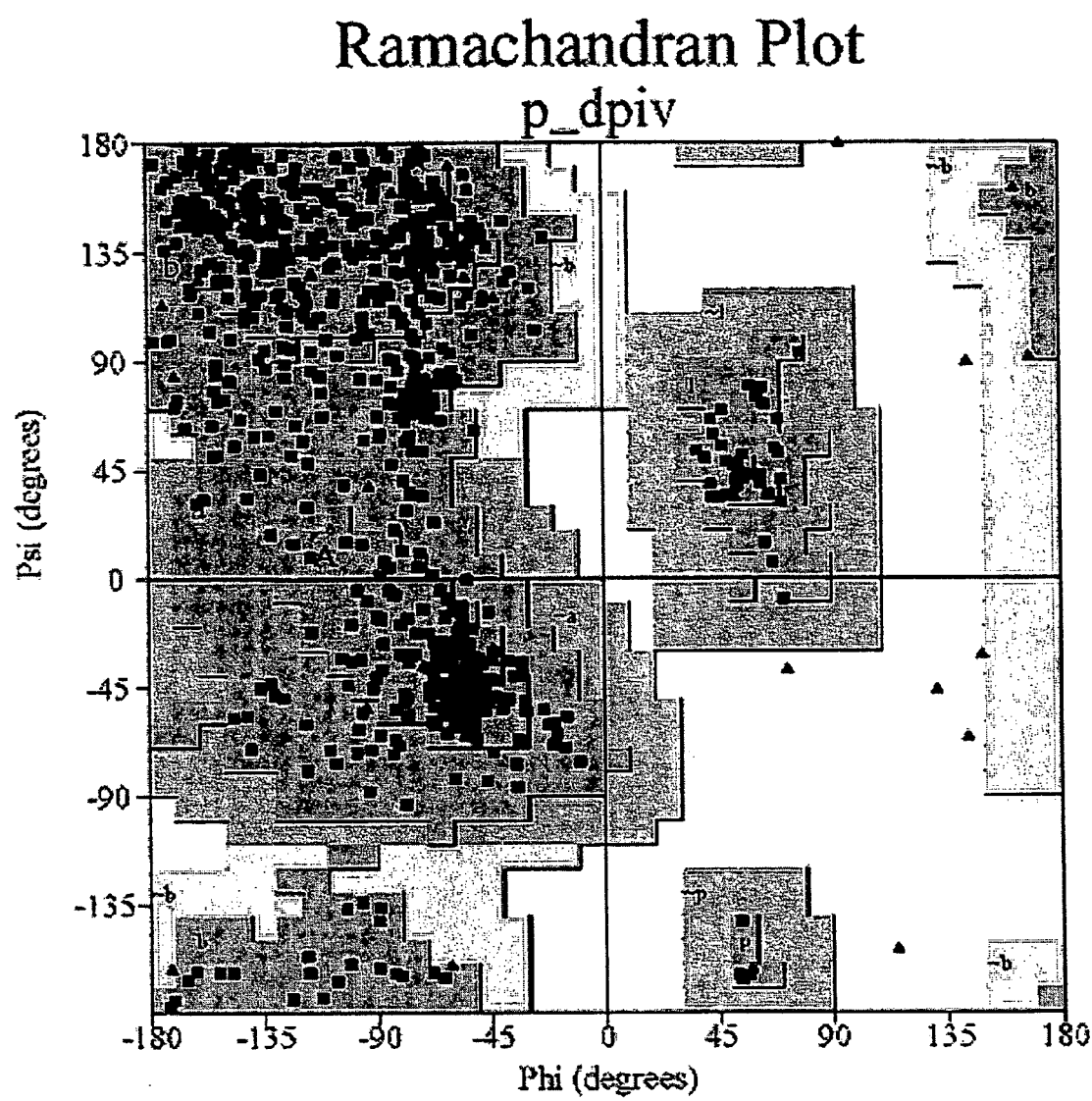
Figure 21A:
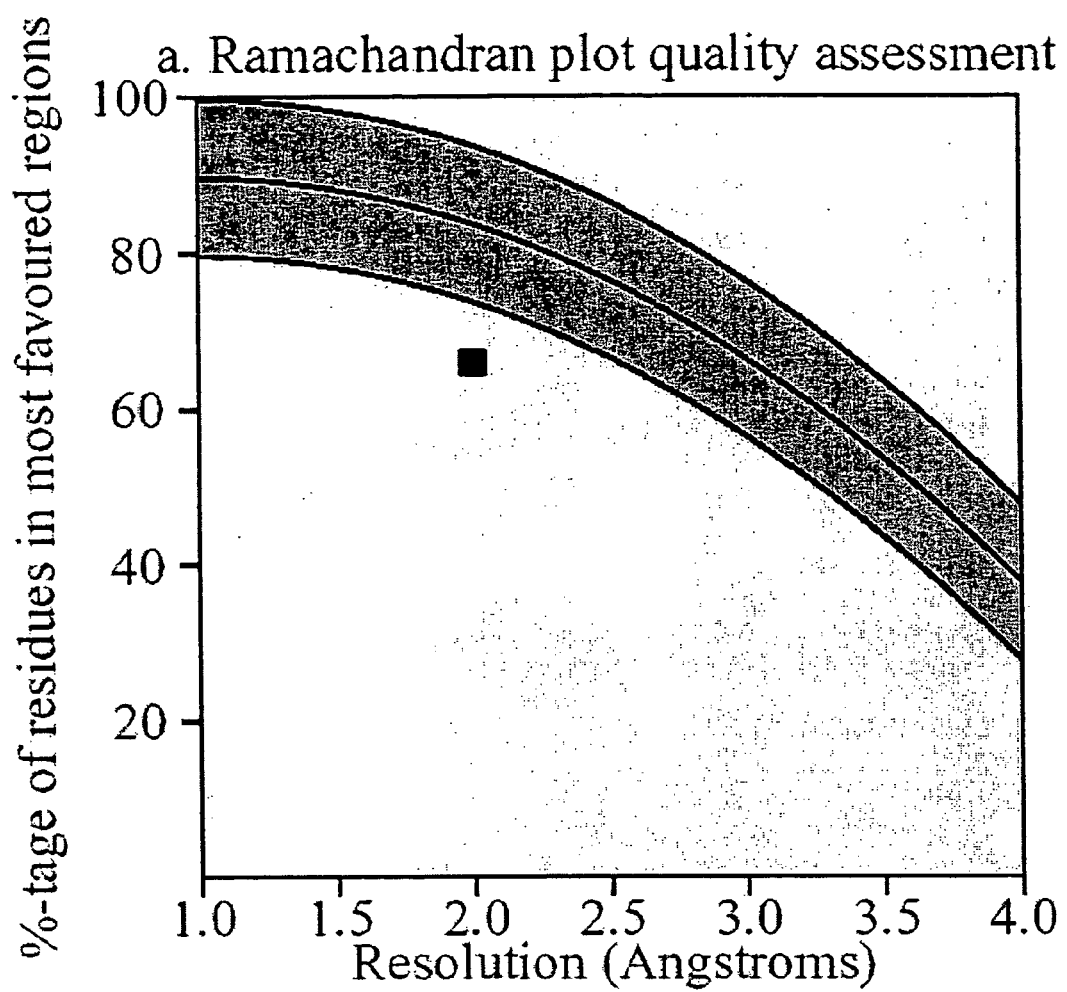
Figure 21B:
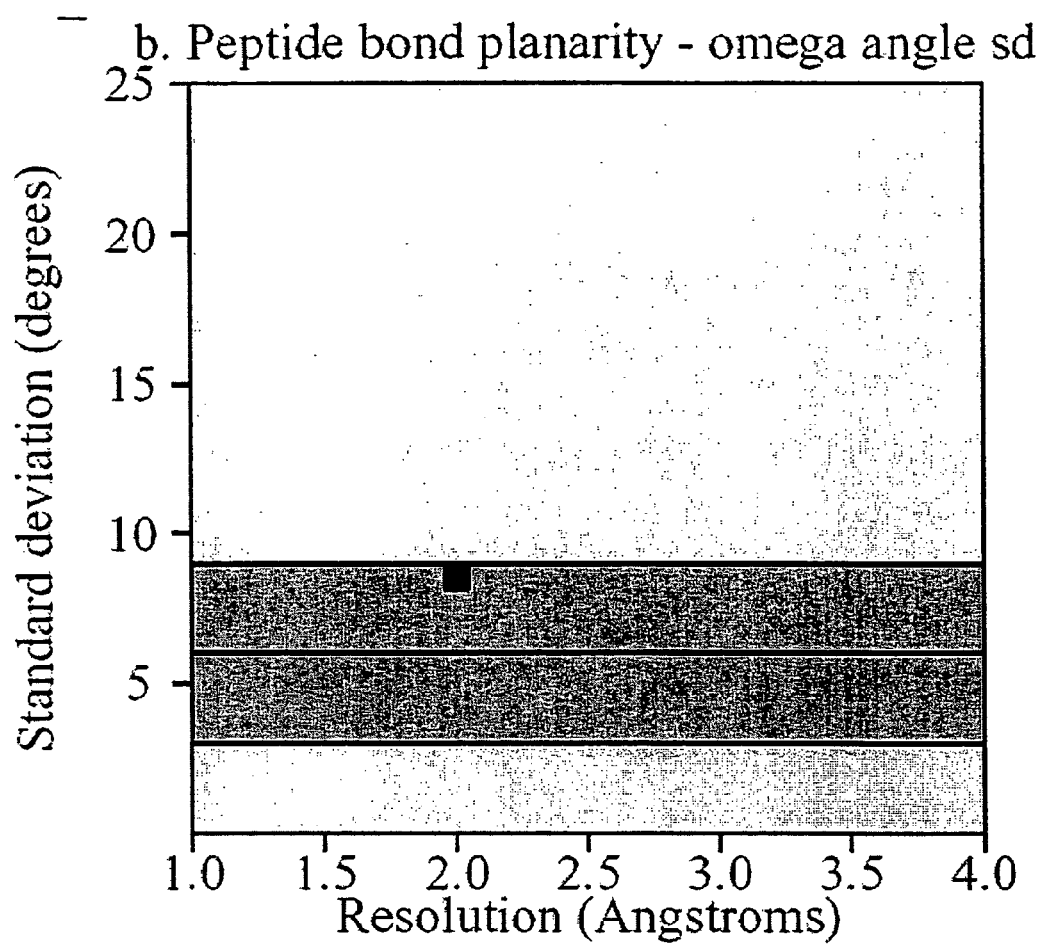
Figure 21C:
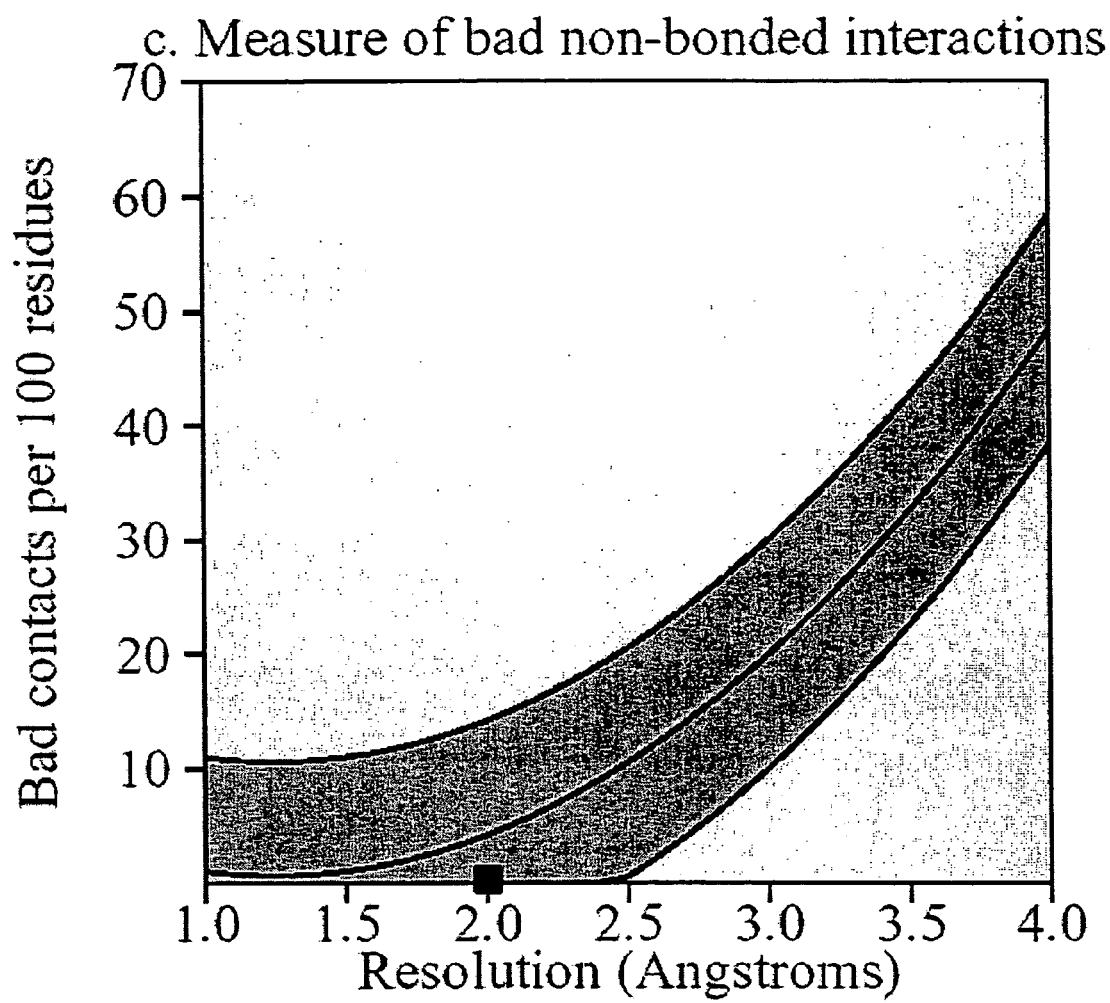
Figure 21D:
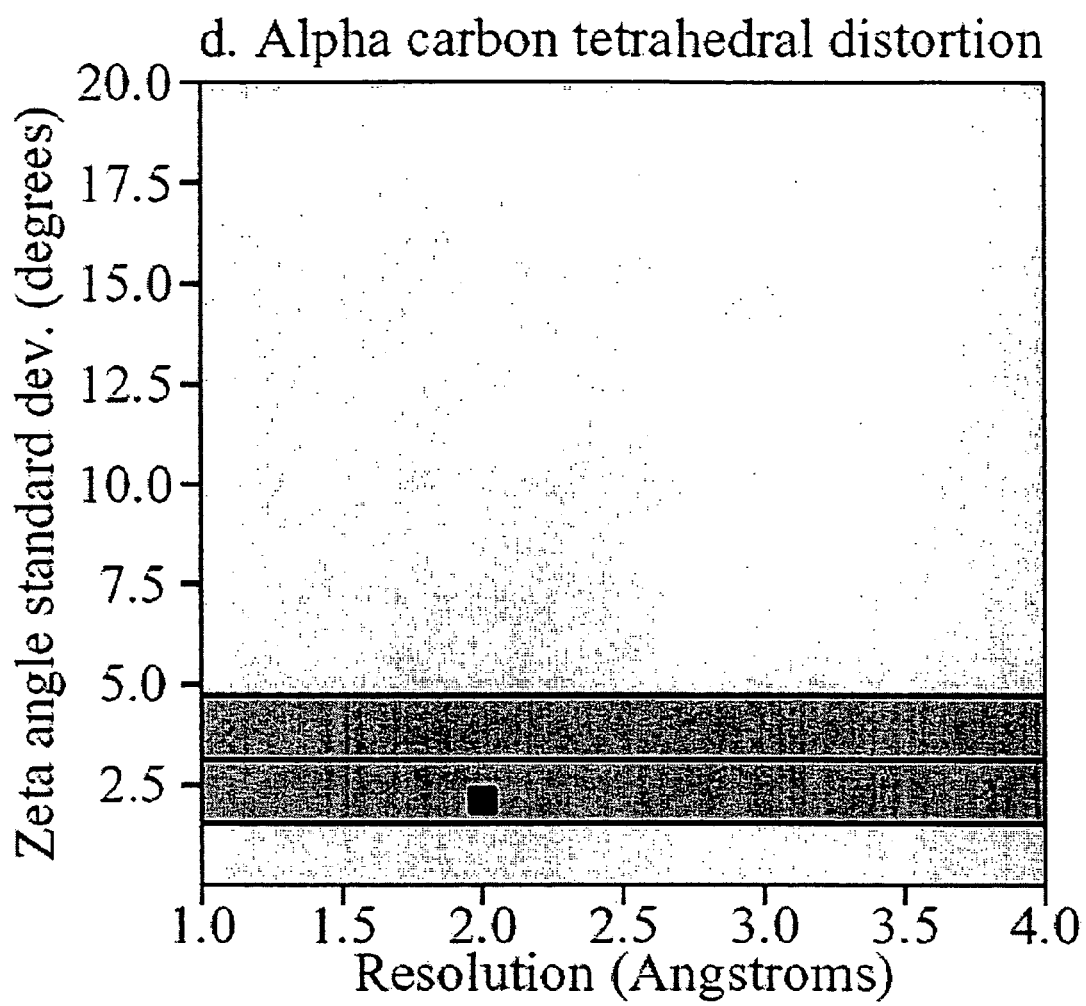
Figure 21E:
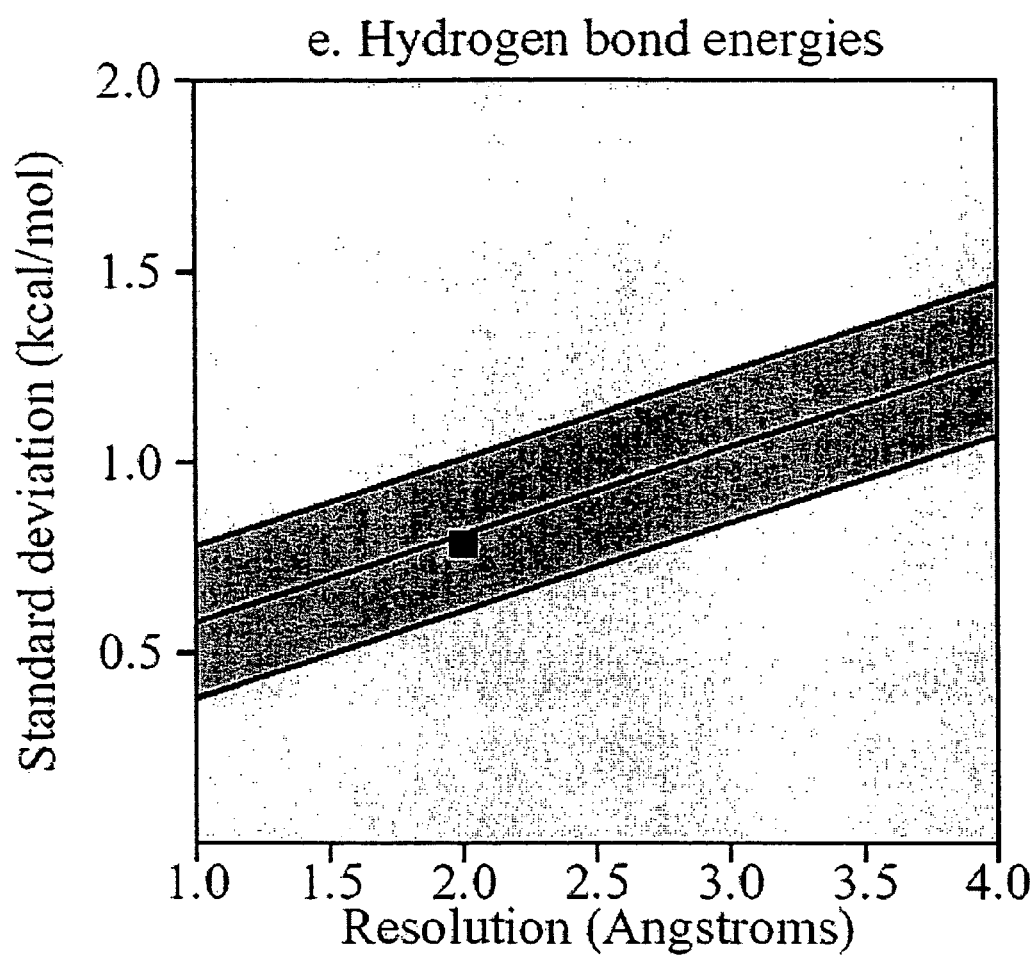
Figure 21F:
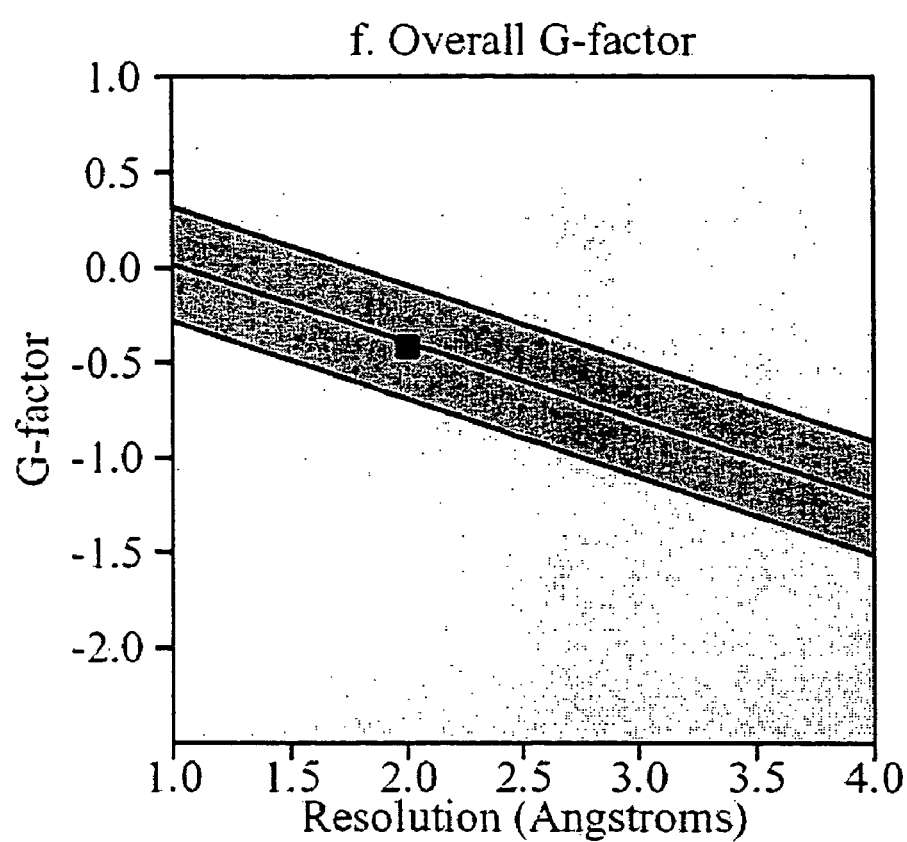
Figure 22A:
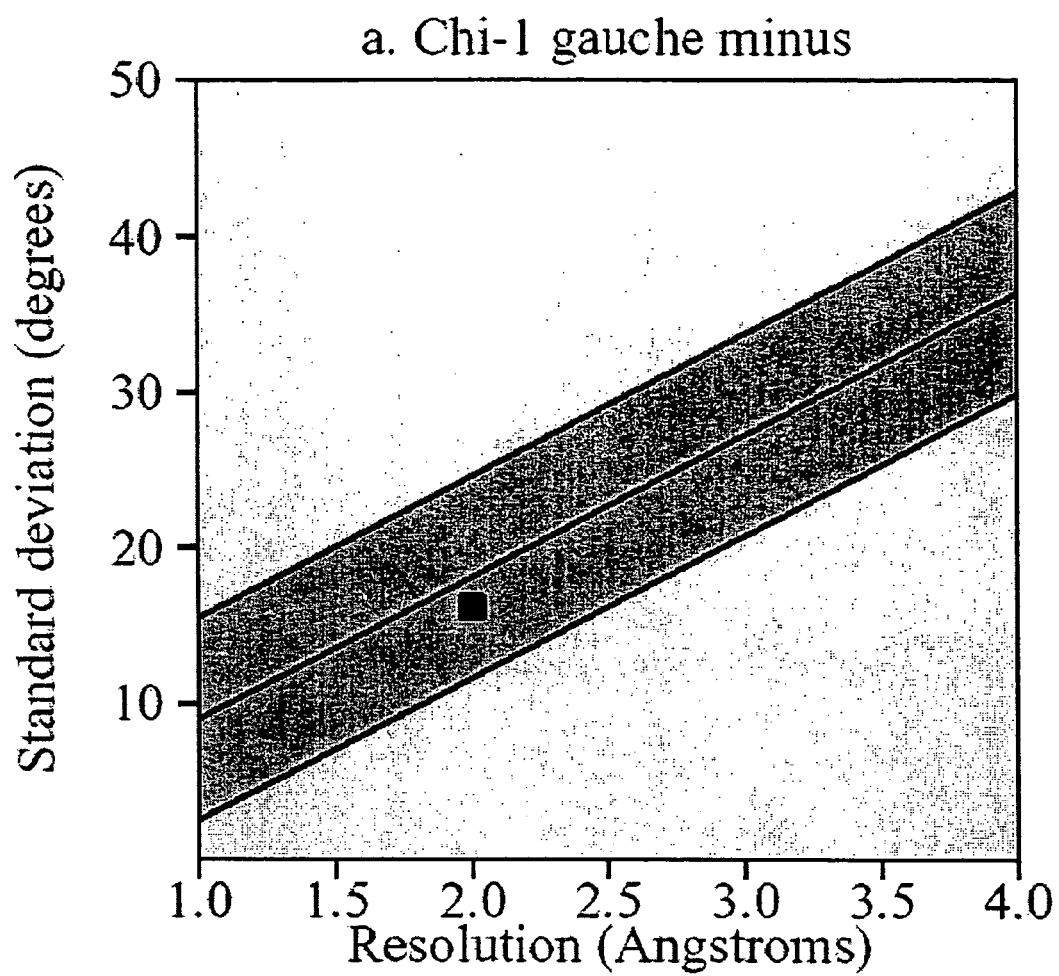
Figure 22B:
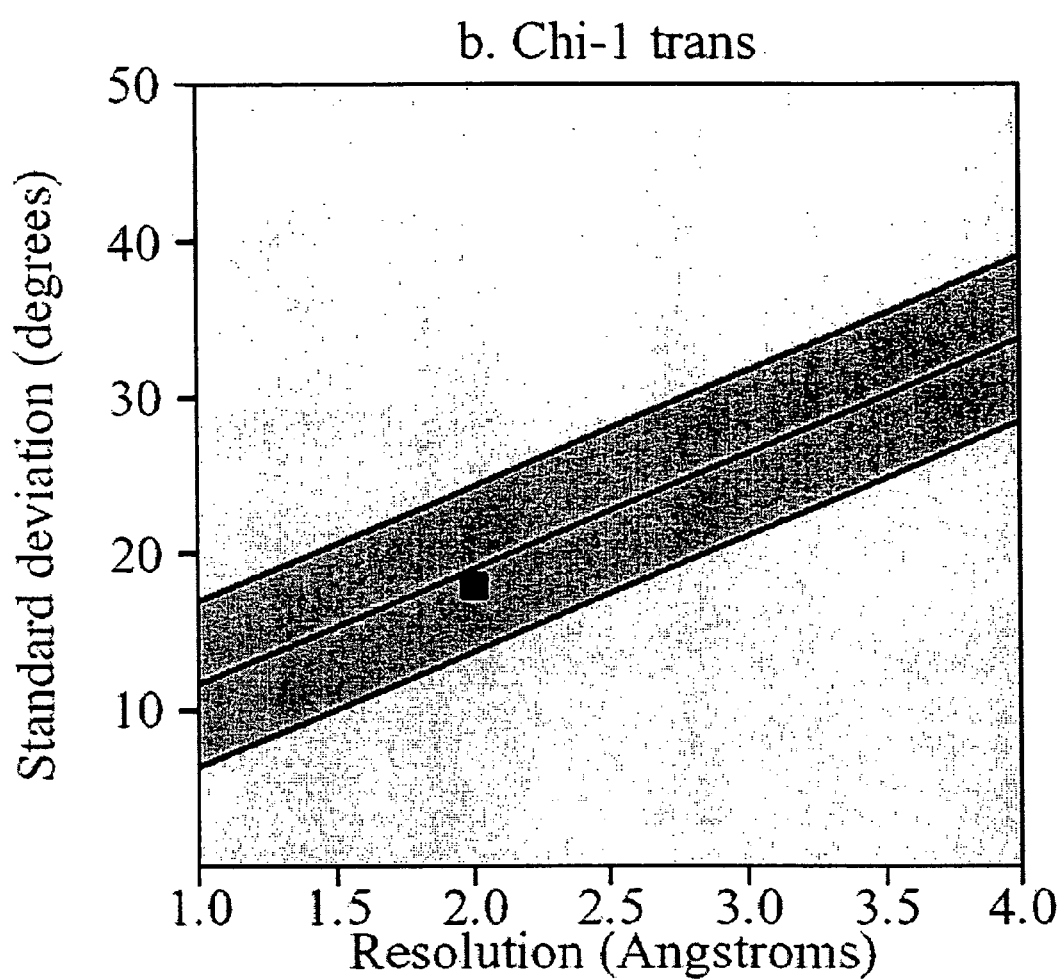
Figure 22C:
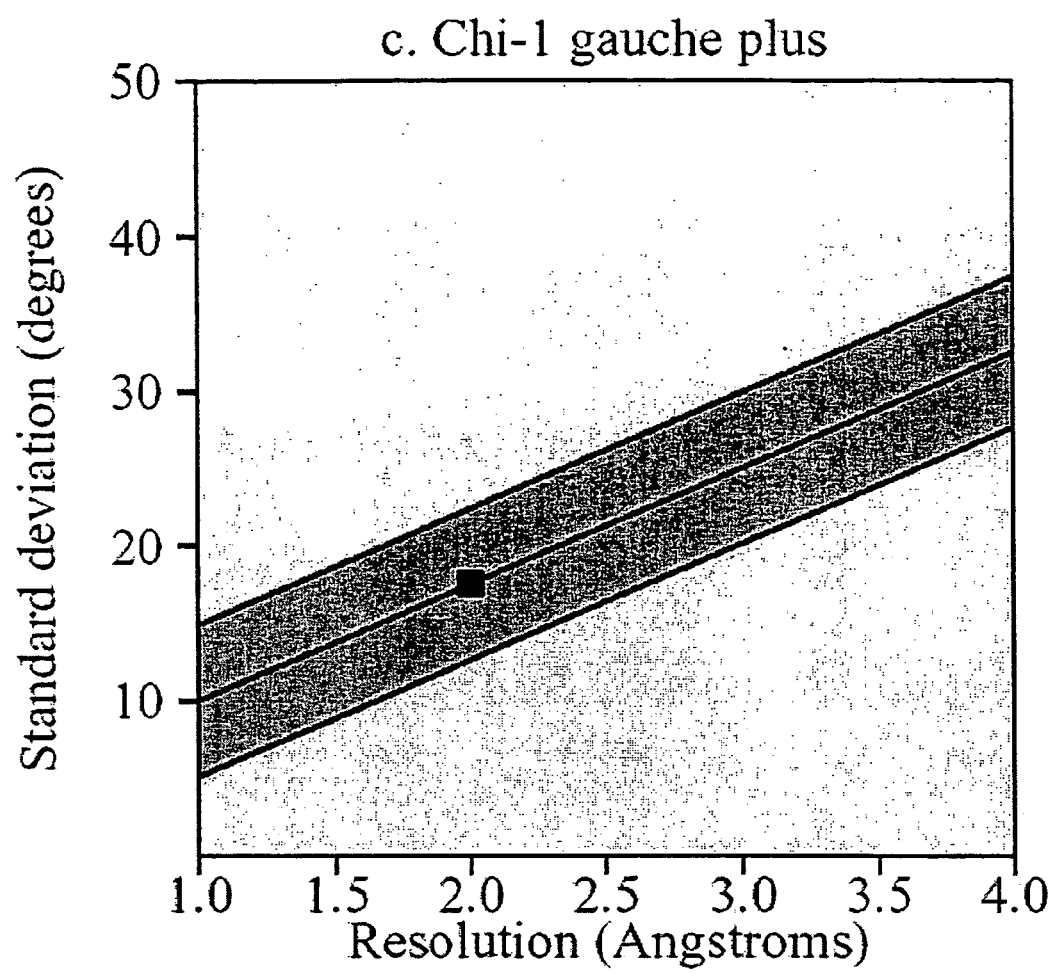
Figure 22D:
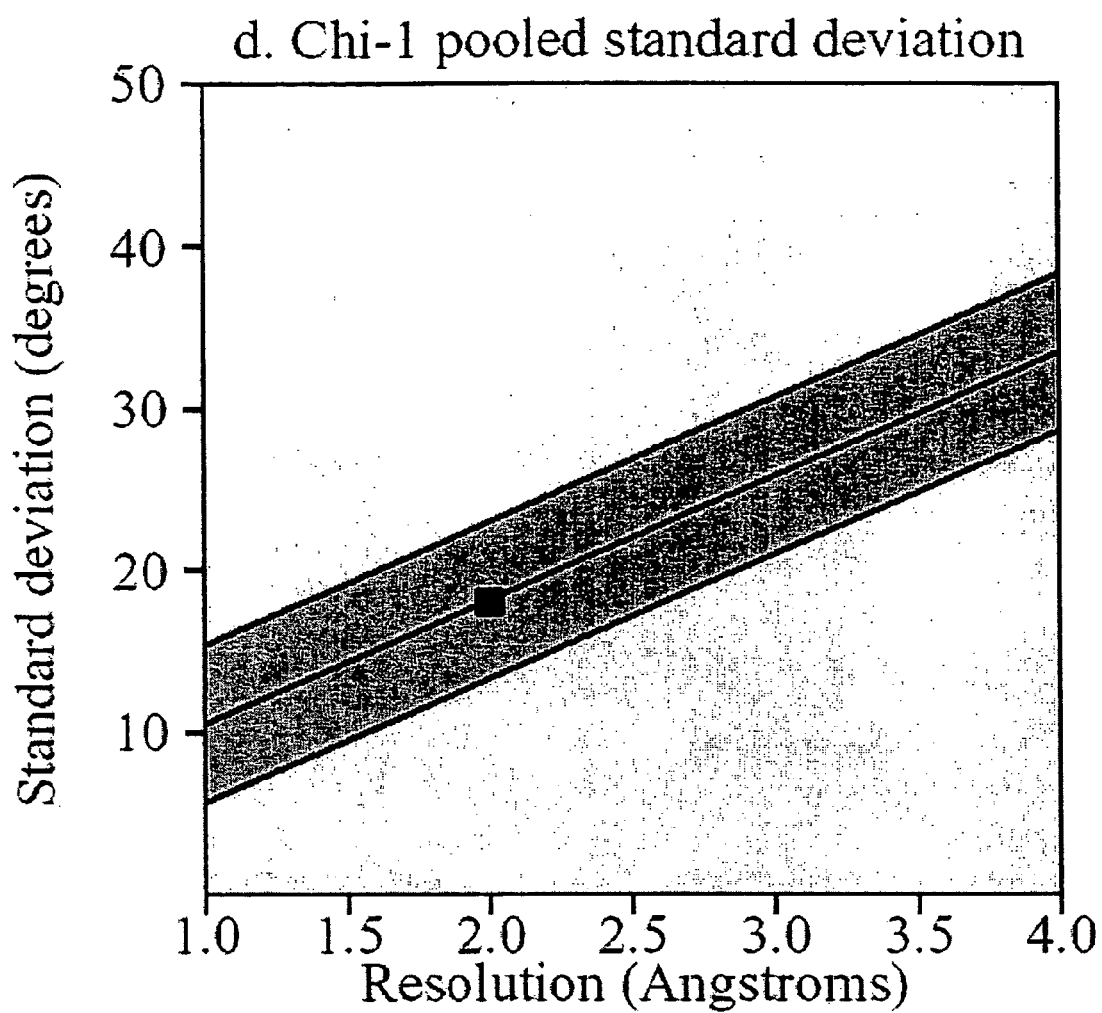
Figure 22E:
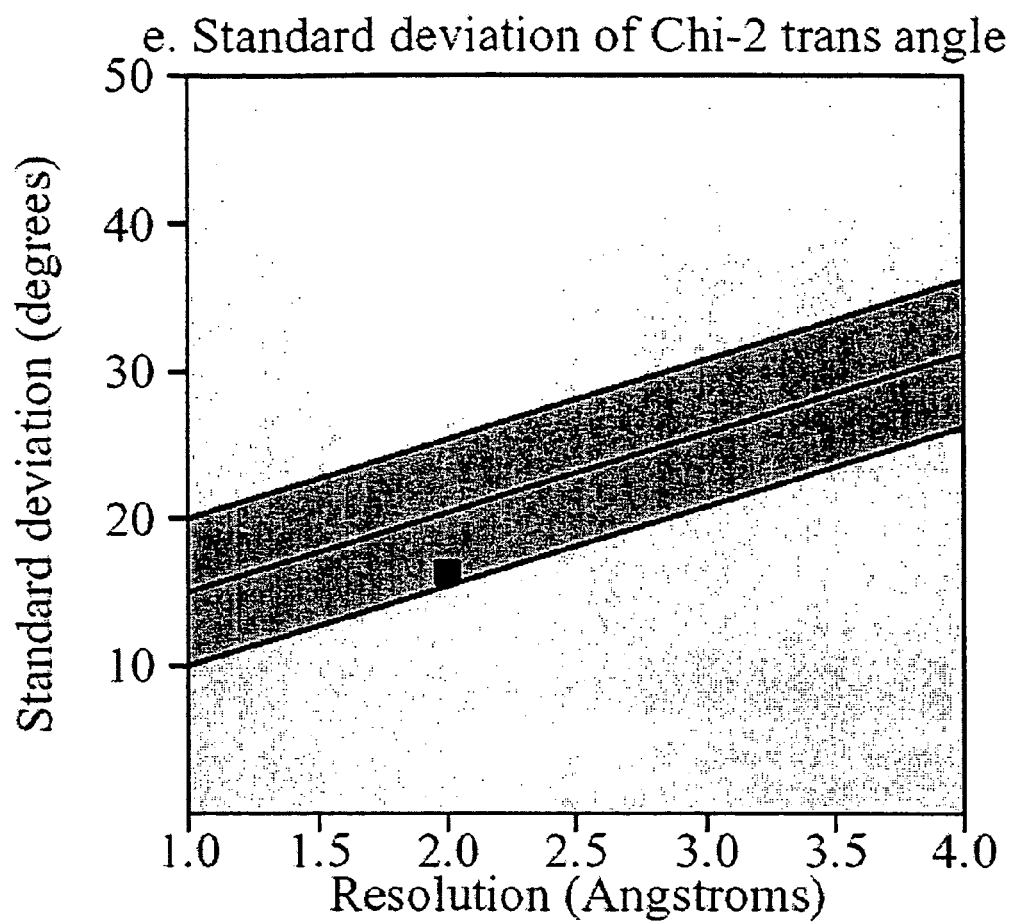

FIG. 3 shows the computer-assisted structure model of DP IV and the ADA-binding site (indicated by the arrows and amino acid residue numbers);

FIG. 4 shows the active site of DP IV docked with the active site DP IV-inhibitor isoleucyl pyrrolidine (Ile-Pyr) (dark gray);

FIG. 5 shows the interaction of Lys-Z-nitro-pyrrolidine with the active site of DP IV;

FIG. 6 shows the tetrahedral intermediate of Asp-Pro-pNA bound to DP IV;

FIG. 7 shows the interaction of the HIV-tat(1-9) protein with DP IV;

FIG. 8 shows the docking of the N-terminal nonapeptide of the tromboxane receptor;

FIG. 9 shows the 3D-structure model of the interaction between GIP (black thread) and human DP IV;

FIG. 10 shows the docking arrangement of GIP (black) to the active site of DP IV;

FIG. 11 shows the molecular dynamic simulation based model of the tertiary structure of GIP (middle part), bound to DP IV. Important amino acid residues from the enzyme are shown in light gray, those from GIP are shown in black, respectively;

FIG. 12 shows the docking of VIP (black) to the active site of DP IV;

FIG. 13 shows the docking of the C-terminal part of VIP to DP IV;

FIG. 14 shows the docking of glucagon (black) to the active site of DP IV;

FIG. 15 shows the molecular dynamic simulation based model of the hexapeptide TFTSDY, bound to the secondary binding site of DP IV. Important amino acid residues from the enzyme are light gray, those from the hexapeptide are marked in dark gray, respectively;

FIG. 16 shows the prolongation of the half-lifes of GIP, Glucagon, PACAP-27 and PACAP-38 by the hexapeptide TFTSDY in a DP IV (porcine and recombinant human) catalyzed peptide truncation test;

FIG. 17 shows the DP IV-catalyzed hydrolysis of RANTES1-15 with (black solid triangle or broken line) or without TFTSDY (black solid square or straight line);

FIG. 18 shows the DP IV-catalyzed hydrolysis of GIP with (black solid triangle) or without TFTSDY (black solid square);

FIG. 19 shows the DP IV-catalyzed hydrolysis of glucagon with (black solid circle) or without TFTSDY (black solid triangle);

FIG. 20 shows a plot of the distribution of the backbone dihedral angles of the complete model of porcine DP IV. All residues are in most favored and additional allowed regions. The plot statistics is as follows:

| | | |
|---|---:|---:|
| Residues in most favoured regions (A, B, L) | 457 | 66.0% |
| Residues in additional allowed regions (a, b, l, p) | 235 | 34.0% |
| Residues in generously allowed regions (~a, ~b, ~l, ~p) | 0 | 0.0% |
| Residues in disallowed regions | 0 | 0.0% |
| Number of non-glycine and non-proline residues | 692 | 100.0% |
| Number of end-residues (excl. Gly and Pro) | 2 | |
| Number of glycine residues (shown as triangles) | 44 | |
| Number of proline residues | 31 | |
| Total number of residues | 769 | |

FIG. 21 shows the analysis of the quality of the model of porcine DP IV with regard to some essential stereo-chemical parameters of the main chain. The plot statistics is as follows:

| Stereochemical parameter | No. of data points | Parameter value | Comparison Values Typical value | Band width | No. of band widths from mean | |
|---|---:|---:|---:|---:|---:|---|
| a. %-tage residues in A, B, L | 692 | 66.0 | 83.8 | 10.0 | −1.8 | WORSE |
| b. Omega angle standard deviation | 765 | 8.5 | 6.0 | 3.0 | 0.8 | Inside |
| c. Bad contacts/100 residues | 2 | 0.3 | 4.2 | 10.0 | −0.4 | Inside |
| d. Zeta angle standard deviation | 725 | 2.1 | 3.1 | 1.6 | −0.6 | Inside |
| e. H-bond energy standard deviation | 400 | 0.8 | 0.8 | 0.2 | −0.1 | Inside |
| f. Overall G-factor | 769 | −0.4 | −0.4 | 0.3 | −0.1 | Inside |

FIG. 22 shows the analysis of the quality of the model of porcine DP IV with regard to some essential stereo-chemical parameters of the side chains. The plot statistics is as follows:

| Stereochemical parameter | No. of data points | Parameter value | Comparison Values Typical value | Band width | No. of band widths from mean | |
|---|---:|---:|---:|---:|---:|---|
| a. Chi-1 gauche minus standard deviation | 156 | 16.2 | 18.1 | 6.5 | −0.3 | Inside |
| b. Chi-1 trans standard deviation | 218 | 17.9 | 19.0 | 5.3 | −0.2 | Inside |
| c. Chi-1 gauche plus standard deviation | 279 | 17.6 | 17.5 | 4.9 | 0.0 | Inside |
| d. Chi-1 pooled standard deviation | 653 | 18.0 | 18.2 | 4.8 | 0.0 | Inside |
| e. Chi-2 trans standard deviation | 144 | 16.3 | 20.4 | 5.0 | −0.8 | Inside |

Figure 23:
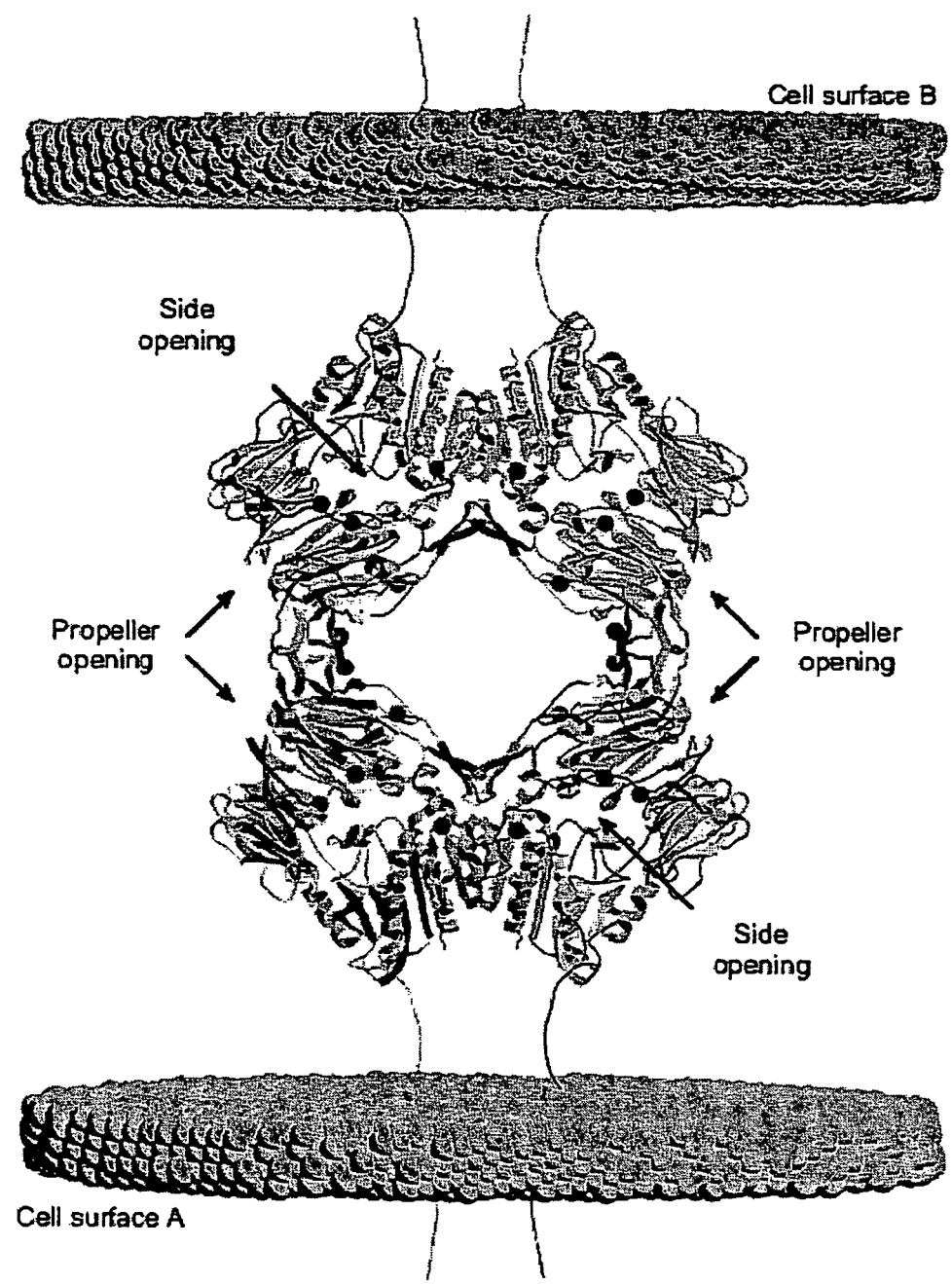

FIG. 23 shows soluble DP IV from prorcine kidney, which forms a 2-2-2 symmetric assembly as dimer of dimers. The view is along one two-fold axis. Potential glycosylation sites are indicated as grey spheres, black spheres are the sites modified in the crystal structure. The transmembrane helices and their orientation to the membrane were modeled to illustrate how tetramerization of DP IV can mediate cell-cell contacts. The figure was prepared by using the program MOLSCRIPT and RASTER3D.

Figure 24:
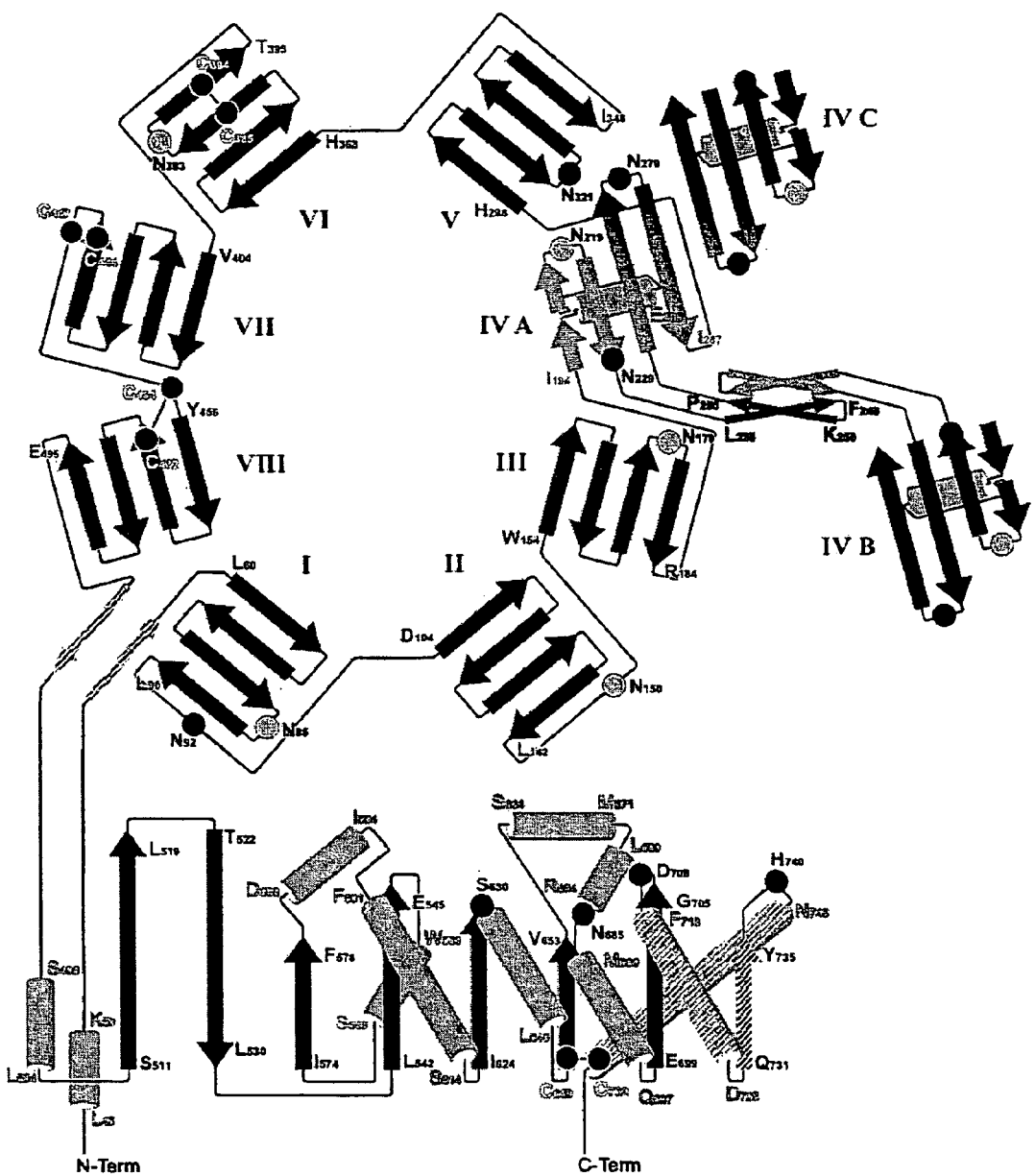

FIG. 24 shows a topology diagram illustrating the domain structure of porcine kidney DP IV. Blade IV of the propeller is involved in both the dimer contact (IV A-IV B: L235-P255, together with the highlighted C-terminal three secondary structure elements F713-C762) and the tetramerization of DP IV (IV A-IV C and IV B-IV C, not shown).

Figure 25:
Figure 25:
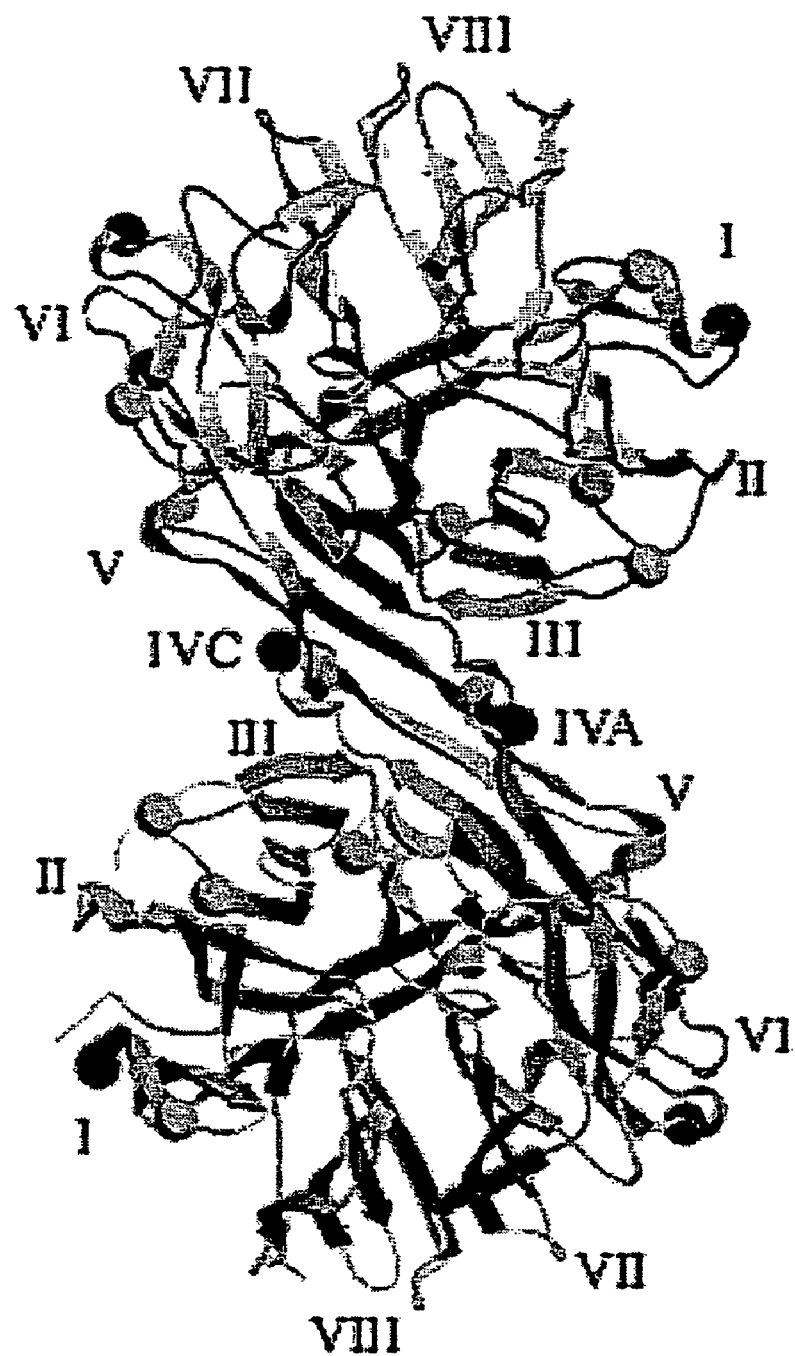

FIG. 25 shows oligomerization interfaces. (A) Detailed view perpendicular to the dimer two-fold axis. The experimental electron density after phase extension to 2.0 Å resolution is superimposed on key residues mediating the contact. (B) View along the two-fold axis on the tetramerization interface. Blades IV of each subunit align to form an eight-bladed antiparallel β sheet. The highlighted Leu294 and Val341 are involved in ADA binding. The figure was prepared using BOBSCRIPT, MOLSCRIPT and RASTER3D.

Figure 26:
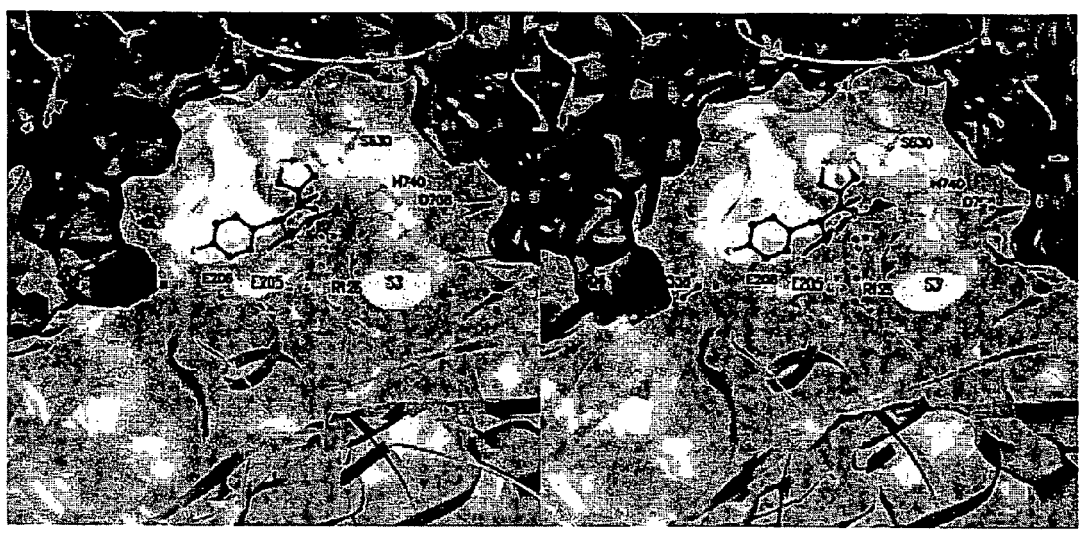
Figure 26:
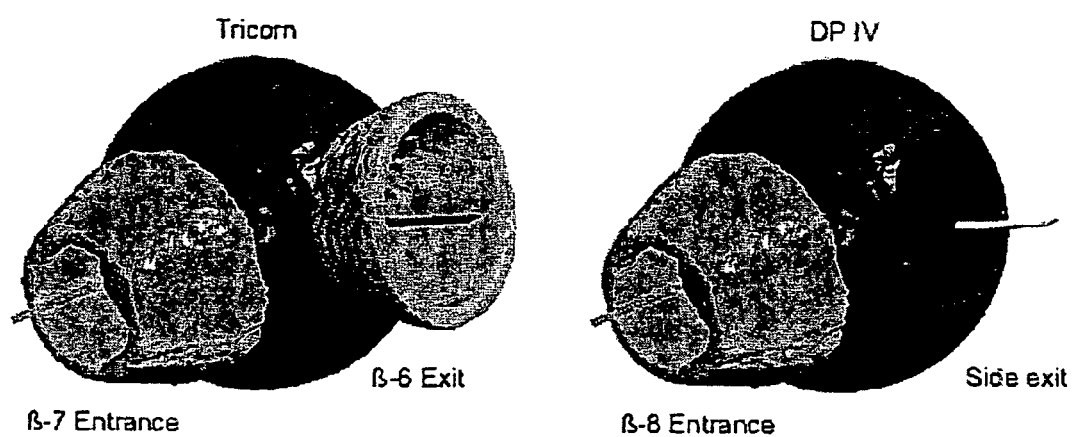

FIG. 26 shows substrate recognition by procine kidney DP IV. (A) The peptidomimetic active-site inhibitor p-Iodo-Phe-Pyr-CN is bound to active site. The accessible surface is indicated and cut-open (dark gray area at the top of the figure) for better visibility. (B) Schematic representation of the active site access in tricom and DP IV. The figure was prepared by using the programs MAIN, MOLSCRIPT, GRASP and RASTER3D.

Figure 27:
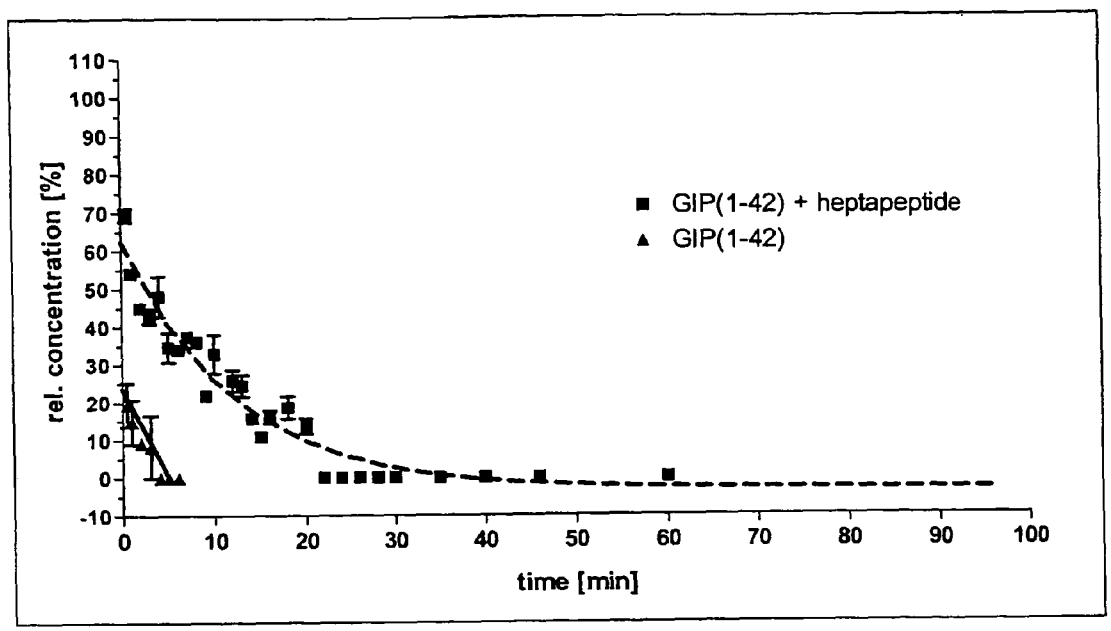

FIG. 27 shows the DP IV-catalyzed hydrolysis of $GIP_{1-42}$ with (black solid squares) or without the heptapeptide H-Ser-D-Glu-Thr-Gly-D-Val-D-Lys-D-Val-OH (black solid triangles).

DETAILED DESCRIPTION OF THE INVENTION

The inventors of the present application unexpectedly show, that the biodegradation of substrates, which bind to the same catalytic domain of DP IV, can be modulated very specifically.

One aspect of the invention is to identify the site in the DP IV protein, which is responsible for the modulation of the substrate specificity and selectivity of DP IV and DP IV-like enzymes and to provide new compounds, which regulate the substrate selectivity and/or activity of DP IV and DP IV-like enzymes and which are useful for the treatment of, for example, impaired glucose tolerance, glucosuria, lipid disorders, dyslipidemia, hyperlipidaemia, hypertriglyceridemia, hypercholesterolemia, low HDL levels, high LDL levels, metabolic acidosis, hyperglycemia, diabetes mellitus, diabetic neuropathy and nephropathy and of sequelae caused by diabetes mellitus in mammals, metabolism-related hypertension and cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, Syndrome X, ovarian hyperandrogenism (polycystic ovarian syndrome), growth hormone deficiency, neutropenia, tumor metastasis, benign prostatic hypertrophy, gingivitis, osteoporosis, and other conditions.

Usually, DP IV is inhibited by compounds mimicking the N-terminal dipeptide part of a DP IV-substrate. This leads to potent compounds which are inhibitors of DP IV and DP IV-like enzymes and inhibit at sufficient concentrations (e.g. 5×$K_i$-dose) the DP IV-catalyzed hydrolysis of small chromogenic or higher molecular weight peptide substrates. In the present invention it is demonstrated that compounds interacting with DP IV-binding sites far distant from the catalytic center are capable to differentiate the degradation of different substrates, e.g. peptide substrates, or even discriminate DP IV-catalyzed hydrolysis completely.

The substrate properties of the peptides of the growth hormone releasing factor (GRF) family against DP IV were examined.

The GRF family consists of the following peptide hormones:
Gastrin-releasing peptide (GRP)
Enterostatin
Peptide histidine methionine (PHM)
Cholecystokinin
Glucagon-like peptide-2 (GLP-2)
Glucose-dependent insulinotropic polypeptide (GIP)
Glucagon-like peptide-1 (GLP-1)
Growth-hormone releasing factor (GRF)
Pituitary-adenylate cyclase activating polypeptide (PACAP (27 und 38))
Vasoactive intestinale peptide (VIP)
Exendin-1
Exendin-2
Exendin-3
Exendin-4
Secretin
Glucagon In particular, the capability of purified DP IV from human, from porcine kidney, of recombinant human DP IV and the DP IV activity of the human serum to truncate the peptides of the GRF family were analyzed. The half-life of the peptides were determined using matrix-assisted laser desorption/ionization time-of-flight mass spectrometry (MALDI-TOF MS) whereas the kinetic constants $K_m$ and $k_{cat}/K_m$ were calculated using capillary zone electrophoresis. All peptides were hydrolyzed by porcine DP IV, recombinant human DP IV or DP IV activity of the human serum. The resulting $K_m$-values were independent from the amino acid in the $P_1$-position. That means that the binding of substrates to DP IV is not mainly affected by the $P_1$-residue rather than by secondary interactions between substrate and DP IV protein.

The same surprising phenomenon of different substrate properties was shown with GIP-fragments of different chain lengths. $V^2$GIP(1-6) and $G^2$GIP(1-6) were not hydrolyzed by DP IV. $V^2$GIP(1-30) and $G^2$GIP(1-30) were accepted as substrates and both $S^2$GIP(1-6) and $S^2$GIP(1-30) were truncated by DP IV (Table 2). These findings prove the existence of a secondary binding site in the DP IV protein, which is responsible for substrate recognition and which modulates the biodegradation of substrates and, therefore forms the basis for the management of substrate selectivity and specificity of DP IV and/or DP IV-like enzymes.

TABLE 2

Truncation half life of various bioactive peptides which are substrates for DP IV

| substance | half-life [min] |
|---|---|
| $GIP_{1-30}$ | 2.68 |
| $S^2GIP_{1-30}$ | 137.14 |
| $V^2GIP_{1-30}$ | 298.04 |
| $G^2GIP_{1-30}$ | 150.02 |
| $GIP_{1-6}$ | <7.5 |
| $S^2GIP_{1-6}$ | 79.04 |
| $V^2GIP_{1-6}$ | no degradation |
| $G^2GIP_{1-6}$ | no degradation |

The amino acid sequences of natural $GIP_{1-30}$ and $GIP_{1-6}$ are:

$GIP_{1-30}$:   YAEGTFISDYSIAMAKIHQQAFVNWLLAQK $GIP_{1-6}$:   YAEGTF

To identify the secondary binding site, a hexapeptide derived from a consensus sequence of the amino acid sequences of GRF-family peptides was synthesized and its influence on the substrate specificity of DP IV was measured. The selected consensus sequence corresponds to glucagon$_{5-10}$, comprising the amino acid sequence TFTSDY. As expected this peptide had only weak influence on the GP-4-Nitroanilide hydrolysis ($K_i$=0.71 mM).

In support of the results achieved with the GRF family peptides, the truncation half-lifes of GIP, GLP-1, NPY, glucagon or PACAP by DP IV were also changed after preincubation with 160 μM TFTSDY (Table 3). No differences could be detected between incubation of Rantes$_{1-15}$ and DP IV with or without the hexapeptide TFTSDY (Table 3). The latter finding shows that the peptide Rantes$_{1-15}$ is too short to reach the secondary binding site and therefore TFTSDY has no effect on its hydrolysis rate. The half-lives of GIP and glucagon in presence of DP IV were prolonged by TFTSDY, the strongest influence had TFTSDY on the DP IV-catalyzed truncation of glucagon.

Further, a modified variant of the hexapeptide TFTSDY, TFTDDY was synthesized, studied for docking in the DP IV 3D structural model and tested for its regulatory efficacy to modulate substrate specificity of DP IV.

TABLE 1

Inhibitory effect of TFTSDY on DP IV-catalyzed peptide truncation expressed in $K_i$-values

| peptide | $K_i$ [µM] | |
|---|---|---|
| | rec. human DP IV | procine DP IV |
| PACAP-27 | 26.7 | n.d. |
| PACAP-38 | 2.8 | n.d. |
| GIP | 14.0 | 65.9 |
| glucagon | 3.7 | 6.8 |
| RANTES$_{1-15}$ | n.d. | 12307.7 |
| GLP-1 | n.d. | 13.7 |
| NPY | n.d. | 17.2 | n.d.—not determined

The hexapeptides TFTSDY and TFTDDY were found to be instable in biological fluids, e.g. human serum or human plasma and/or they were rapidly degraded by proteolytic enzymes in the serum or plasma. Therefore, and in another embodiment of the present invention, a heptapeptide of the sequence H-Ser-D-Glu-Thr-Gly-D-Val-D-Lys-D-Val-OH was synthesized. This heptapeptide is not enzymatically degraded in human serum or plasma and is stable in these fluids. A stabilization of the heptapeptide was especially achieved by the incorporation of D-amino acids in the molecule. It was further shown to be very effective in improving the substrate specificity of DP IV compared to control experiments without the heptapeptide.

The existence of a secondary binding site was proven, e.g. using a set of dipeptide compounds, coupled to a chromogenic (p-nitroaniline, pNA) or fluorogenic (aminomethylcoumarine, AMC) group. The dipeptides His-Pro, His-Ala, His-Ser, His-Val, His-Gly, and His-Thr represent the first two amino acids from the N-terminus of the following peptide hormones: GIP, GLP-1, GLP-2, PACAP, VIP, PHM and glucagon. The peptide hormones GIP, GLP-1, GLP-2, PACAP, VIP, PHM and glucagon are substrates of DP IV. DP IV hydrolizes these peptide hormones and the respective N-terminal dipeptides are released. In contrast, the dipeptides are much slower released, when they are coupled to the chromogenic (p-nitroaniline, pNA) or fluorogenic (aminomethylcoumarine, AMC) group. Secondary interactions of the peptide hormones GIP, GLP-1, GLP-2, PACAP, VIP, PHM and glucagon far from the DP IV active site must exist as a prerequisite for substrate recognition. Data supporting the existence of a secondary binding site of DP IV are shown in table 4 below

TABLE 4

DP IV-catalyzed hydrolysis of His-Ser-, His-Gly and His-Val-dipeptides compared to the full-lenght substrates glucagon and NPY.

| Compound | $K_m$ [M] |
|---|---|
| His-Ser-AMC | $2.1 * 10^{-2}$ |
| Glucagon | $3.8 * 10^{-6}$ |
| His$^1$-Ser$^2$-NPY | $6.8 * 10^{-5}$ |
| His-Gly-AMC | $4.1 * 10^{-4}$ |
| [Gly]$^2$-glucagon | $2.2 * 10^{-5}$ |
| His-Val-AMC | $1.9 * 10^{-2}$ |

The Prolyl Oligopeptidase (POP) Based Computer-Generated Models of Human DP IV

Prolyl oligopeptidase (POP) based computer-generated models of human DP IV and porcine DP IV and the crystal structure of porcine DP IV were used according to the present invention to predict enzyme-substrate-interactions and to identify the interaction site in the DP IV protein structure.

Since the sequence homology between DP IV and the template POP is not very high, standard methods for homology modeling such as the application of COMPOSER gave only very crude preliminary models which needed a lot of manual modification and improvements. These improvements were made by inspection of the conformation and spatial position of each of the 766 amino acid residues with regard to forming sheets or helices and favored intra-residual interactions such as hydrogen bonds, salt bridges and hydrophobic interactions as well. All modifications made were examined by using PROCHECK, which allows the analysis of the stereochemical quality of the model (dihedral angles in favored areas of a Ramachandran Plot, see FIG. 1 for human DP IV and FIG. 20 for porcine DP IV), bond angles and bond length, hydrogen bonds (see FIG. 2 for human DP IV and FIGS. 21 and 22 for porcine DP IV), and by PROSA which analyzes its energy in comparison to native folded proteins. All these residues show that some residues are located in unfavorable areas but all belong to loop regions of the propeller domain which is not of essential importance for docking studies and predictions of new ligands.

In summary of this part, the model of DP IV used herein is in a state where the overall fold is correct and highly useful for the explanation of experimental results and to allow predictions of recommendations for positions of site directed mutagenesis, development of ligands based on the identified second binding site or selective ligands to bind at the closer active site.

In order to identify essential amino acids for the secondary interaction independently from the active site, site-directed mutageneses were performed using human DP IV cDNA. The mutation sites were: W629A and R560A. The characterization of these mutants showed that both mutations have no influence on the enzyme catalyzed hydrolysis of GP-4-nitroanilide and the kinetic parameters of short and/or low molecular weight inhibitors, which are directed to the active site of DP IV (see table 5). Another mutated enzyme variant, R310A, was expressed as inactive protein. This mutation resulted in the appearance of three DP IV fragments. Based on the computer generated model was shown that an intramolecular salt bridge is formed between R310 and D332 and that this intramolecular salt bridge is crucial for the formation and stabilization of the DP IV tertiary protein structure.

TABLE 5

Kinetic characterization of DP IV-catalyzed substrate hydrolysis by mutants of DP IV in the secondary binding site

| Mutation | Test compound | $K_m$ [M] | $K_i$ [M] | kcat [s$^{-1}$] | $k_{cat}/K_m$ [M$^{-1}$ * s$^{-1}$] |
|---|---|---|---|---|---|
| mu 15 DP IV | Gly-Ser-AMC | Not hydrolyzed | | | |
| mu 15 DP IV | Gly-Pro-AMC | 4.66E−05 | | 1.00E+06 | 2.15E+10 |
| mu 15 DP IV | V²GIP(1-4)* | | no inhibition | | |
| mu 15 DP IV | S²GIP(1-6)* | | no inhibition | | |
| mu 15 DP IV | Glucagon (1-14)* | | no inhibition | | |
| mu 15 DP IV | Leu-Thia-Fum* | | 6.81E−08 | | |
| mu 15 DP IV | TFTSDY* | | no inhibition | | |
| mu 15 DP IV | PACAP(1-38)* | | 3.67E−05 | | |
| mu 15 DP IV | Transp 01* | | 7.69E−08 | | |
| mu 15 DP IV | YAESTF amide* | | 1.14E−06 | | |
| mu 16 DP IV | Gly-Ser-AMC | Not hydrolyzed | | | |
| mu 16 DP IV | Gly-Pro-AMC | 5.02E−05 | | 1.44E+06 | 2.86E+10 |
| mu 16 DP IV | V²GIP(1-4)* | | no inhibition | | |
| mu 16 DP IV | S²GIP(1-6)* | | no inhibition | | |
| mu 16 DP IV | Glucagon (1-14)* | | no inhibition | | |
| mu 16 DP IV | PACAP(1-38)* | | 3.21E−05 | | |
| mu 16 DP IV | Transp 01* | | 8.55E−08 | | |
| mu 16 DP IV | YAESTF amide* | | 1.06E−06 | | |
| mu 16 DP IV | TFTSDY* | | no inhibition | | |
| mu 16 DP IV | Leu-Thia Fum* | | 6.57E−08 | | |
| rh wt DP IV | Gly-Ser-AMC | 4.4E−04 | | | |
| rh wt DP IV | Gly-Pro-AMC | 3.53E−05 | | 1.66E+06 | 4.7E+10 |
| rh wt DP IV | V²GIP(1-4)* | | no inhibition | | |
| rh wt DP IV | S²GIP(1-6)* | | no inhibition | | |
| rh wt DP IV | Glucagon (1-14)* | | no inhibition | | |
| rh wt DP IV | PACAP(1-27)* | 2.28E−04 | 1.13E−04 | | |
| rh wt DP IV | PACAP(1-38)* | | 3.83E−05 | | |
| rh wt DP IV | Transp 01* | | 5.08E−08 | | |
| rh wt DP IV | YAESTF amide* | | 3.51E−08 | | |
| rh wt DP IV | TFTSDY* | | no inhibition | | |
| rh wt DP IV | Leu-Thia Fum* | 4.26E−05 | 6.58E−08 | | |
| p wt DP IV | Leu-Thia-Fum* | 5.98E−05 | 7.29E−08 | | |
| p wt DP IV | PACAP(1-27)* | 1.22E−04 | 5.43E−05 | | |

*The Ki-values were determined in competition of the test compound to the standard substrate GP-4NA (see examples). No inhibition means that the compound doesn't influence the DP IV-catalyzed hydrolysis of the standard substrate GP-4NA.

Definitions in table 5:

| | |
|---|---|
| mu 15 | recombinant human DP IV, mutation R560A |
| mu 16 | recombinant human DP IV, mutation W629A |
| rh wt | recombinant human DP IV, wild type |
| p wt | porcine kidney DP IV, wild type |
| Transp 01 | RRLSYSRRRF-E-Thia |

In the present invention a region was identified in the DP IV-protein, which is responsible for the interaction with a hexapeptide, e.g. TFTSDY or TFTDDY, or more suitably, a degadation resistant heptapeptide, e.g. H-Ser-D-Glu-Thr-Gly-D-Val-D-Lys-D-Val-OH.

The most important amino acids for the formation of the secondary binding site on DP IV for the GRF family of peptide hormones were found to be but are not restricted to L90, E 91, T 152, W154, W157, R310, Y330, R318, Y416, S460, K463, E464 and R560.

The Crystal Structure of DP IV

In a further embodiment of the present invention, the sequence and 1.8 Å crystal structure of native DP IV prepared from porcine kidney were determined. The crystal structure reveals a 2-2-2 symmetric tetrameric assembly which depends on the natively glycosylated β-propeller blade IV. The crystal structure indicates that tetramerization of DP IV is a key mechanism to regulate its interaction with other components. Each subunit comprises two structural domains, the N-terminal eight-bladed β-propeller with open Velcro topology and the C-terminal α/β-hydrolase domain. Analogy with the structurally related POP and tricom protease suggests that substrates access the buried active site through the β-propeller tunnel while products leave the active site through a separate side exit. A dipeptide mimicking inhibitor complexed to the active site discloses key determinants for substrate recognition, including a Glu-Glu motif which distinguishes DP IV as an aminopeptidase and an oxyanion trap which binds and activates the P$_2$-carbonyl oxygen necessary for efficient post-proline cleavage.

Sequence of the Porcine DP IV

Sequence comparison of the porcine DP IV with the human and other mammalian DP IV-sequences reveals a very high degree of sequence conservation. In particular, there is not a single sequence insertion or deletion between the porcine and the human sequence. The overall sequence identity between these two species is 88%. (and 92% within the catalytic domain). Noteworthy, Ser339 in the porcine sequence substitutes for Cys339 in the human sequence, causing the absence of an extra disulfide bond (Cys328-Cys339) in human DP IV. In comparison to the human sequence the potential glycosylation site at Asn520 is lost because of an Asn-His exchange. On the other hand there is an additional potential glycosylation site at Asn179 which is not found in the human sequence. Interestingly, the glycosylation site at Asn279 is found at Asn281 in the human sequence.

Recently, the structure of human DP IV was published (PDB entry code 1N1M) (Rasmussen H. B., Branner, S., Wiberg, F. C., Wagtmann, N. (2002) http://www.nature.com/naturestructuralbiology, published online 16 Dec. 2002.) The model of porcine DP IV according to the present invention was refined by using the program CNS with current R-values of 21.7% (working set) and 24.9% (test set) and deviations from ideality of 0.008 Å (bond length) and 1.4 degree (angle deviation).

Overall Structure and Subunit Assembly

The monomer comprises an N-terminal β-propeller domain (Arg54-Asn497) followed by the catalytic domain Gln508-Pro766. Notably, the crystal structure reveals a dimer of DP IV dimers in the crystallographic unit cell obeying a 222 symmetry with all axes intersecting, FIG. 23. The by far more extensive dimer contact is predominantly mediated by residues of the catalytic domain with a contact area of 2270 Å$^2$ versus the dimer-to-tetramer interface of 2×570 Å$^2$= 1140 Å$^2$. The dimer interface is dominated by hydrophobic interactions, with a central and well shielded aromatic stacking involving Trp734 and Phe713 of both monomers. The hydrophobic contacts are complemented by polar interactions such as Asp729 with His754 and His757, FIG. 25A. Notably, the Gln731(Oε1)-Gln731(Nε2) contact resembles a subtle (atomic) break of the exact two-fold symmetry within the dimer. The residues critical to the dimerization are strictly conserved throughout all species.

The dimer-dimer interface has a more hydrophilic character. In its center, the strands Asn279-Gln286 of each DP IV-dimer form an antiparallel β-sheet, thus extending propeller blade IV to an eight-stranded antiparallel sheet, FIG. 25 B. An additional contribution to the tetrameric assembly in our crystals arises from the outer strands of blade V. The residues contributing to the dimer-dimer contact are similar over different species, albeit especially in rodents not strictly identical. More importantly, there are no insertions or deletions in the outer β strands of blade IV with a contact area of 570 Å$^2$ per monomer. Significantly, Asn279 is located at the tetramerization interface and is glycosylated (FIGS. 23, 25 B). Thus, glycosylation of Asn279 might provide one missing regulatory link which was proposed to control the assembly of a 900 kDa oligomer (Lambeir, A. M., Pereira, J. F. D., Chacon, P., Vermeulen, G., Heremans, K., Devreese, B., VanBeeumen, J., Demeester, I. & Scharpe, S. (1997) Biochim. Biophys. Acta 1340, 215-226.).

Subdomain Structure

The β-propeller. The N-terminal β-propeller domain contains eight blades with four antiparallel strands each. Typically for β propeller structures, the first and the last blade of a β-propeller is clamped together either covalently by disulfide bond formation (four-bladed β-propellers) or by strand exchange between the first and last blade (five to eight-bladed propellers). So far there are three exceptions to this closed propeller topology rule, namely the seven bladed β-propeller of POP (Fülöp, V., Böcskei, Z. & Polgár, L. (1998) Cell 94, 161-170.), the seven and the six bladed propellers of the tricom protease (Brandstetter, H., Kim, J.-S., Groll, M. & Huber, R. (2001) Nature 414, 466-469.), and the five bladed propeller of α-L-arabinase 43A (Nurizzo, D., Turkenburg, J. P., Charnock, S. J., Roberts, S. M., Dodson, E. J., McKie, V. A., Taylor, E. J., Gilbert, H. J. & Davies, G. J. (2002) Nature Struct. Biol. 9, 665-668.). The β8-propeller of DP IV can also be classified as an open Velcro-type topology, because no segment C-terminal to blade VIII interacts with the first propeller blade. Interestingly, however, the interaction of the first strand within blade I is limited to Thr59-Ile63 while its N-terminal extension Phe53-Tyr58 tightens up the propeller structure by interacting with the immediate C-terminal extension to the fourth strand of blade VIII (Glu499-Met503). A similar, yet shorter, external clamp has been described for the β7-propeller of the tricorn protease (Brandstetter, H., Kim, J.-S., Groll, M. & Huber, R. (2001) Nature 414, 466-469.).

With the exception of Cys649-Cys762 all disulfide bonds are located in the β propeller domain where they form intrablade stabilizing crosslinks exclusively, FIG. 24. Cys339 in the human sequence is replaced by Ser339 in the porcine sequence which causes the absence of the disulfide bond connecting strand 3 and 4 of blade V (Cys328-Cys339 in human DP IV), although the backbone conformation of the strands would readily allow a disulfide bond to be formed. Similarly, all glycosylation sites but Asn685 are located on the β-propeller. Five of in total 10 potential glycosylation sites cluster at the top surface side oriented away from the catalytic domain. Four are positioned on the loops connecting strand 3 and 4 of blade I (Asn85), III (Asn179), IV (Asn279) and VI (Asn393), one on the loop connecting strand 1 and 2 of blade IV (Asn219), FIGS. 23, 24. Intriguingly, out of these five potential glycosylation sites only Asn279 is actually posttranslationally modified which is involved in the tetramerization of DP IV. Further glycosylation sites are located on blade I (Asn92 at the end of strand 4), blade IV (Asn229 close to the tetramerization motif), blade V (Asn321 on the loop connecting strand 2 and 3), FIGS. 23, 24. Asn150 on the exit strand of blade II is not actually modified in the crystals. The shape of the DP IV-β8-propeller is asymmetric where blades VI, VII, VIII, I, and blades II, III, IV, V form more compact subdomains, respectively (FIGS. 23, 25 B). The structural division of the β-propeller fits physico-chemical data which indicated a three domain organization of DP IV (Lambeir, A. M., Pereira, J. F. D., Chacon, P., Vermeulen, G., Heremans, K., Devreese, B., VanBeeumen, J., Demeester, I. & Scharpe, S. (1997) Biochim. Biophys. Acta 1340, 215-226.). The ellipsoidal tunnel through the propeller is continuously open. At the solvent exposed opening, its diameter measures 9 Å and 15 Å from blade IV to VIII and from blade II to VI, respectively. The tunnel widens towards the catalytic domain with opening diameters of 15 Å and 25 Å between the same pairs of propeller blades. By its dimensions, the tunnel allows for direct passage of an extended peptide, but not for a folded α-helix.

Only few solvent molecules are visible in the tunnel, most remarkable a sulfate is bound to the oxyanion pocket formed by the amide nitrogens of Glu361 and Ile407 and Nε2 of His363.

The Catalytic domain. The catalytic domain is located at the C-terminus of DP IV and spans residues Gln509 to Pro766. It adopts a typical α/β-hydrolase fold with a central 8 stranded β sheet, where only the second strand Thr522-Pro531 deviates from the otherwise parallel strand polarity, FIG. 23. The β-sheet exerts a significant twist of more than 90 degrees, in line with observations on related α/β-hydrolases.

Within the catalytic domain a single disulfide bond Cys649-Cys762 crosslinks the C-terminal helix Met746-Ser764 with the sixth strand of the β-sheet (Lys648-Ala654), thus stabilizing its tertiary arrangement. Helix Met746-Ser764, together with helix Gln714-Asp725 and strand Asp729-Thr736 from the C-terminal region, constitutes the central dimerization motif which is further stabilized through an interaction contributed by the oligomerization blade IV of the β-propeller.

The β-sheet is sandwiched by several α-helices, including helix Tyr631-Ala642 immediately succeeding the catalytic Ser630. Ser630 is embedded in the surrounding secondary structure framework where it participates both in the preceding strand 4 (Arg623-Trp629) as well as in the following helix Tyr631-Ala642. This causes a strained backbone conformation of the active site Ser630. The high energy conformation of Ser630 is reflected by its dihedral angles (φ, ψ)=(61.4,−115.7) and presumably provides a reservoir needed for catalysis (Goettig, P., Groll, M., Kim, J.-S., Huber, R. & Brandstetter, H. (2002) *EMBO J.* 21, 5343-5352.).

Active site and substrate recognition. The sequential and three-dimensional arrangement of the catalytic residues Ser630, His740, Asp708 corresponds to that of related α/β-hydrolases. The oxyanion hole is formed by the amide Tyr631 and the hydroxyl Oη of Tyr547 and serves to recognize and activate the carbonyl oxygen of the $P_1$-residue. It is occupied by a water molecule in the uninhibited structure. To detail the exact mechanism of substrate recognition, the structure of a dipeptid mimetic, the iodinated Phe-cyanopyrrolidide inhibitor in complex with DP IV was determined (FIG. 26 A). The active site nucleophile, the hydroxyl residue of Ser630, forms a covalent bond with the scissile carbonyl carbon of the cyanopyrrolidine of the inhibitor. The bending of the linkage (FIG. 26 A) indicates the formation of a stable carbaminic acid adduct. The pyrrolidine ring is accommodated by a hydrophobic pocket formed by side chains of Tyr666, Tyr662, Val711, Val656 and Trp659. While this environment is almost perfectly suited for the imino acid proline as $P_1$-residue, the hydroxyl Oη of Tyr662 would be correctly positioned to interact with the normal amide nitrogen of an amino acid in $P_1$. The inhibitor also unambiguously maps the $S_2$-site. The $P_2$-carbonyl oxygen gets trapped in an electrostatic sink formed by the side chains of Arg125 and Asn710. Glu205 and Glu206, and to a lesser extent the carbonyl oxygen of Glu205, interact with the free amino terminus of the $P_2$-residue, thus determining the dipeptidyl "amino"-peptidase activity of the enzyme. It is, therefore, the β-propeller which provides essential determinants for $P_2$-recognition, namely Arg125, which is positioned on the hairpin loop between strands 2 and 3 of blade II and Glu205-Glu206, positioned on a short helical insertion within strand 1 of the β propeller blade IV. Ample space is available to accommodate voluminous side chains such as Tyr or Trp in $P_2$, FIG. 26 A. In our inhibitor the phenyl ring of the $P_2$-residue is iodated rather than hydroxylated. It forms an ionic interaction with Arg358, FIG. 26 A.

Substrate access to and product egress from the active site. The β-propeller domain covers the active site and thereby restricts the substrate access to it. There are two possible routes to the active site, namely through the tunnel of the β-propeller and through a side opening. Similar as the propeller tunnel, the shape of the side entrance is oval with dimensions of 15 Å and 22 Å. The side opening to the active site is generated by the kinked blade arrangement of blade I and II, FIG. 23. In POP, blades I and II are arranged more regularly and there is no side opening to the active site chamber. The distance from the protein surface to the active site measures 20 Å and 37 Å through the side opening and the propeller tunnel, respectively. From its dimensions, both routes give active site access to unfolded peptidic substrates, but the side entrance is significantly shorter and less winded. Once the substrate has been cleaved, two products have to leave the active site chamber. Clearly, the product exit route differs from the entrance to the active site.

Based on the crystal structure model new functional characteristics of DP IV were identified and are part of the present invention. These new features of DP IV are:

Oligomerization of membrane-bound and soluble DP IV. Tetramerization on the cell surface involves, for geometric reasons, a membrane bound and a soluble DP IV dimer pair or dimers located on the surface of two different cells, as illustrated on FIG. 23. DP IV is known as a cell-cell communication molecule. Thus, the way DP IV is involved in mediating such cell-cell contacts may be by tetramerization of two homodimers present on the surface of interacting cells. Alternatively, soluble dimers can assemble to form a homotetramer, as observed in the crystal structure described above. The tetramer assembles to enclose a large cavity. Since tetramerization of DP IV depends on the correctly glycosylated propeller blade IV, glycosylation could function as a quality control unit.

Dimerization is mediated by the three C-terminal secondary structure elements positioned on the catalytic domain, and a finger like insertion motif within strand 2 and 3 of propeller blade IV. Furthermore, DP IV is known to form heterodimers with fibroblast activation protein α (FAPα, seprase). Like DP IV (FAPβ), FAPα lacks an N-terminal extension as found in POP. Moreover, the essential elements of the DP IV-dimerization motif are also present in FAPα, including the extension of strand 2 and 3 of propeller blade IV.

Functional role of oligomerization. The crystal structure shows that dimerization is not required to complete the active site architecture of DP IV, as for example in the case of tricorn (Brandstetter, H., Kim, J.-S., Groll, M. & Huber, R. (2001) *Nature* 414, 466-469.). Instead, dimerization and tetramerization will affect interaction with other components, including proteolytic substrates and ADA and mediate cell-cell contacts. Moreover, dimerization of DP IV is likely to enhance the receptor-ligand affinity by bivalent interaction. Finally, it is likely that dimerization is critical for signal transduction into the cell.

Substrate preference and catalytic mechanism. The hydrophobic $S_1$-pocket visualizes that proline is perfectly suited as a $P_1$-residue, although it will also fit other small uncharged residues such as alanine or serine. Interestingly, the $S_1$-site implements a mechanism to adapt to both imino and amino acids in $P_1$-position. The hydroxyl Oη of Tyr662 is able to form a hydrogen bond with the $P_1$-amide nitrogen and thus optimally presents the substrate for catalysis. By contrast, the proper orientation of proline in $P_1$-position is achieved by its side chain interaction in addition to the binding to the oxyanion pocket. In this situation, the hydroxyl of Tyr662 can slightly reorient to form a hydrogen bond with the side chain Oδ1 of Asn710, FIG. 26 A. The recognition of the $P_2$-residue is dictated by main chain interactions with two prominent anchor sites, namely Glu205-Glu206 which form a twin-single salt bridge with the free amino terminus of the $P_2$-residue; and Arg125 together with Nε2 of Asn710 which stabilize and activate the $P_2$-carbonyl oxygen. The Glu205-Glu206 motif is highly conserved in the DP IV gene family and it has been shown by site directed mutagenesis to be essential for enzymatic activity. The role of the $P_1$ oxyanion hole in activating the substrate's scissile bond is well established for all proteases. In the case of DP IV as a post-proline processing enzyme an additional requirement has to be met to achieve efficient catalysis. Proline containing peptides can adopt in solution also cis-peptide bond as well as trans-peptide bond conformation. However, as highlighted by the inhibitor used in this invention, only a peptide in trans-conformation is able to productively bind to the active site.

β-propeller architecture: The tunnel through the eight-bladed β-propeller widens from the surface towards the active site of DP IV.

Substrate access to and product egress from the active site. Two openings of similar diameter, but differing length, give access to the active site. The situation in DP IV is most closely resembled by the tricorn protease where a seven-bladed and six-bladed β-propeller provide a separate entrance to and exit from the active site, respectively. Tricom protease is a serine protease with low but significant structural homology to the family of c/-hydrolases. This similarity suggests that the β8-propeller provides substrate access to and the side opening product release from the DP IV active site. This tricom-derived model is able to explain the high substrate selectivity critical for DP IV-function to activate or inactivate regulatory peptides. Passage through the β-propeller tunnel requires the substrates to unfold thereby providing their "finger print" to DP IV. Once the amino terminus of the peptide approaches the active site, it is still held in place by its C-terminus interacting with the β-propeller which then contributes to conformationally activate the substrate for cleavage. After the nucleophilic attack the acyl enzyme intermediate forms, while the primed product is directly released through the side exit.

Interaction with other components. DP IV binds adenosine deaminase (ADA) to the T-cell surface, thereby preventing the cell from adenosine mediated inhibition of proliferation. DP IV-ADA complex formation is presumably hydrophobically driven, as the complex dissociates at very low ionic strength. By using site-directed mutagenesis, Leu294 and Val341 were identified as two ADA binding sites (Abbott, C. A., McCaughan, G. W., Levy, M. T., Church, W. B. & Gorrell, M. D. (1999) *Eur. J Biochem.* 226, 798-810.). Leu294 and Val341 are positioned at the outer strand of the tetramerization blade IV and blade V, respectively. Therefore, ADA-binding will interfere with tetramerization. Similarly, the glycosylation of Asn279 (Asn281 in the human sequence) is likely to influence ADA-binding. This teaches that tetramerization of DP IV and proper glycosylation of Asn279 serve as major control mechanism for ADA-binding DP IV as a target for drug design. The inhibitor structure used to establish the crystal structure of DP IV in the present invention identified important recognition elements at DP IV's active site and represents an excellent starting point for rational design of active site directed inhibitors. However, DP IV's involvement in a great variety of physiological processes poses a high challenge to avoid unwanted side effects for any DP IV drug development program. Ideally, it is possible now to target a particular DP IV substrate rather than the complete DP IV activity. Active site directed DP IV inhibitors, however, will interfere with the complete DP IV proteolytic activity and might even interfere with structurally related members of the α-β hydrolase family. Non-active site directed inhibition strategies depict a solution to this problem. The sulfate bound to the oxyanion pocket within the β propeller tunnel formed by the amide nitrogens of Glu361 and Ile407 and Nε2 of His363, as indicated in FIG. 26 A, identified an excellent target point for the development of inhibitors that block substrate passage through the β propeller tunnel.

In the peptides, proteins and mutants shown, each encoded residue where appropriate is represented by a one-letter or a three-letter designation, corresponding to the trivial name of the amino acid, in accordance with usual practice. Examples of usual definitions are given in the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |

-continued

| Amino Acid | One-Letter Symbol | Three-Letter Symbol |
|---|---|---|
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Selenocysteine | | Sec |

In a preferred embodiment of the present invention, a secondary binding site in the DP IV protein and/or DP IV-like enzymes is identified. More preferred, the existence of this secondary binding site can be used to influence the selectivity of the DP IV-catalyzed biodegradation of DP IV-substrates, e.g. alanine (GIP), proline (GRP) or serine (glucagon) substrates, dependent on the amino acid residue in the P1 position and dependent on the tertiary structure of the DP IV-substrates. Preferred DP IV-substrates, the biodegradation whereof shall be regulated according to the invention with compounds, which bind to the secondary binding site, are serine substrates.

The regulation of the biodegradation of DP IV-substrates due to compounds, which bind to the secondary binding site, is further dependent on the chain length of the substrates. Preferably, DP IV-substrates have a chain length of more than 5 amino acid residues, more preferably more than 10 amino acid residues. Most preferred are substrates with more than 15 amino acid residues up to 70 amino acid residues.

Currently known substrates of DP IV are:

Xaa-Pro Peptides
Tyr-melanostatin
Endomorphin-2
Enterostatin
β-Casomorphin
Trypsinogen pro-peptide
Bradykinin
Substance P
Corticotropin-like intermediate lobe peptide
Gastrin-releasing peptide
Neuropeptide Y
Peptide YY
Aprotinin
RANTES
GCP-2
SDF-1α
SDF-1β
MDC
MCP-1
MCP-2
MCP-3
Eotaxin
IP-10
Insulin-like growth factor-I
Pro-colipase
Interleukin-2
Interleukin-1β

α$_1$-Microglobulin
Prolactin
Trypsinogen
Chorionic gonadotropin

Xaa-Ala Peptides
PHM
GRH-(1-29)
GRH-(1-44)
GLP-1
GLP-2
Gastric inhibitory peptide
Orexin B Xaa-Ser Peptides
Orexin A In the most preferred embodiment of the present invention, compounds for the modulation of DP IV-catalyzed biodegradation of DP IV-substrates are provided, which compounds bind to the secondary binding site of DP IV or DP IV-like enzymes. Such compounds are e.g. selected from the compounds of the formulas a)-d):

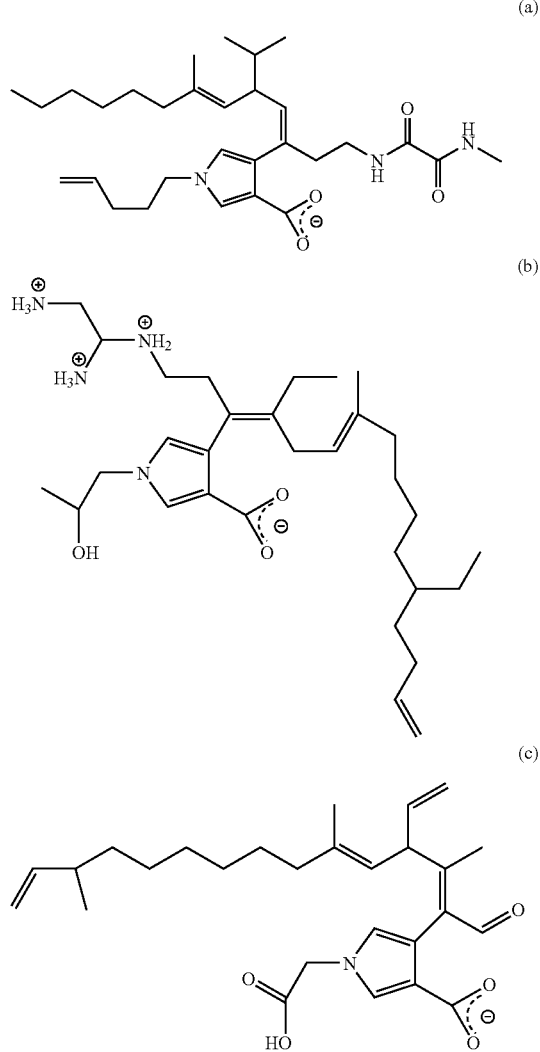

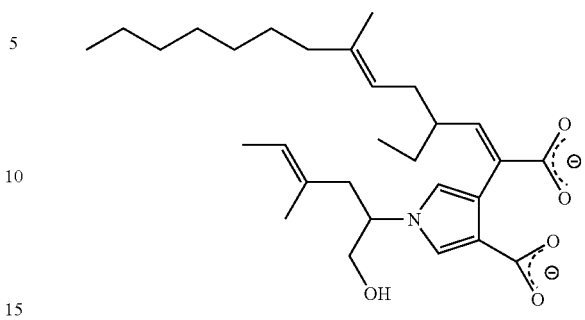

Furthermore, the present invention provides agents, which bind to both the active site and the secondary binding site of DP IV and DP IV-like enzymes and thereby simultaneously modulate the enzyme activity and substrate specificity of DP IV or DP IV-like enzymes.

DP IV is present in a wide variety of mammalian organs and tissues e.g. the intestinal brush-border (Gutschmidt S. et al., "In situ"—measurements of protein contents in the brush border region along rat jejunal villi and their correlations with four enzyme activities. Histochemistry 1981, 72 (3), 467-79), exocrine epithelia, hepatocytes, renal tubuli, endothelia, myofibroblasts (Feller A. C. et al., A monoclonal antibody detecting dipeptidylpeptidase IV in human tissue. Virchows Arch. A. Pathol. Anat. Histopathol. 1986; 409 (2):263-73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151-61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435-52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486-96), the serum high molecular weight form of DP IV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714-21). It is also a goal of the present invention to minimize possible side effects of currently available DP IV-inhibitors by the control and management of the DP IV substrate specificity for the selective treatment of a DP IV mediated disease.

In another preferred embodiment of the present invention, all molecular forms, homologues and epitopes of proteins showing DP IV or DP IV-like enzyme activity, from all mammalian tissues and organs, also of those, which are undiscovered yet, are intended to be embraced by the scope of this invention.

Among the rare group of proline-specific proteases, DP IV was originally believed to be the only membrane-bound enzyme specific for proline as the penultimate residue at the amino-terminus of the polypeptide chain. However, other molecules, even structurally non-homologous with the DP IV but bearing corresponding enzyme activity, have been identified. DP IV-like enzymes, which are identified so far, are e.g.

fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), DPL1 (DPX, DP6), DPP 9 and DPL2 (DPP 10) are described in the review articles by Sedo & Malik (Sedo & Malik, Dipeptidyl peptidase IV-like molecules: homologous proteins or homologous activities? Biochimica et Biophysica Acta 2001, 36506: 1-10) and Abbott & Gorrell (Abbott, C. A. & Gorrell, M. D., The family of CD26/DP IV and related ectopeptidases. In: Langner & Ansorge (ed.), Ectopeptidases. Kluwer Academic/Plenum Publishers, New York, 2002, pp. 171-195), and in Qi, S.Y., Cloning and characterization of dipeptidyl peptidase 10, a new member of an emerging subgroup of serine proteases.

Another preferred embodiment of the present invention comprises screening methods for agents which bind to the secondary binding site and/or modulate the selectivity and/or the activity of DP IV and/or DP IV-like enzymes. An agent according to the invention preferably binds to at least one secondary binding site of the DP IV or DP IV-like enzyme proteins.

The screening method for agents of the secondary binding site comprises the following steps:
a) Contacting at least one of that effectors with DP IV and/or a DP IV-like enzyme, preferably under conditions which permit binding there between;
b) Adding a substrate of DP IV and/or DP IV-like enzymes to said DP IV and/or DP IV-like enzyme;
c) Monitoring the biodegradation of the substrate and/or measuring the residual DP IV and/or DP IV-like enzyme activity;
d) Correlating changes in the biodegradation and/or enzyme activity with the binding of said effectors to DP IV and/or DP IV-like enzymes; and
e) Identification of selectivity and/or activity modifying effectors.

The agents selected by the above described screening method can work by regulating (increasing or decreasing) the biodegradation of at least one substrate of DP IV or the DP IV-like enzyme, preferably by the prolongation of the half-life of such substrate, most preferably by the inhibition of the biodegradation of such substrate.

Conditions, under which binding between compounds and DP IV or DP IV-like enzymes are permitted, are described, e. g. in example 2.

DP IV or DP IV-like enzymes as used in the screening method described above mean purified DP IV or DP IV-like enzymes from mammals, selected from but not restricted to human, monkey, mouse, rat etc., or DP IV or DP IV-like enzyme containing cells and cell lines from mammals, selected from but not restricted to human, monkey, mouse, rat etc., or DP IV or DP IV-like enzyme containing cell extracts or body liquids e.g. liver extracts, blood plasma samples, blood serum samples, brain extracts etc., from such mammals.

Preferably, an agent increases the selectivity and/or activity of DP IV or DP IV-like enzymes towards substrates by at least about 10, preferably about 50, more preferably about 75, 90 or 100% relative to the absence of the agent. More preferably, an agent increases the selectivity and/or activity of DP IV or DP IV-like enzymes towards specific substrates by at least about 10, preferably about 50, more preferably about 75, 90 or 100% and prolongs the half live of the substrates in the serum or in the plasma of a mammal at least about 1fold, preferably about 2fold, more preferably about 3fold, 4fold or higher relative to the absence of the agent. Most preferably, an agent increases the selectivity and/or activity of DP IV or DP IV-like enzymes in such a way that the half live of at least one substrate in the serum or in the plasma of a mammal is increased at least about 1fold, preferably about 2fold, more preferably about 3fold, 4fold or higher, most preferably complete inhibition of the degradation of such a substrate is achieved, relative to the absence of the agent.

It is also preferred according to the invention that the agents modulate the interaction between DP IV or DP IV-like enzymes and binding proteins thereof. Binding proteins are proteins that bind other proteins in a non-covalent manner and thereby modulate their activity or serve as carriers of these proteins. Binding proteins of DP IV (CD26) identified so far include adenosine deaminase, two proteins of HIV, transactivator protein (tat) and the gp120 envelope protein, CD45, a membrane located tyrosine phosphatase, extracellular matrix proteins, such as collagen and fibronectin, plasminogen and streptokinase, mannose 6-phosphat/insulin-like growth factor II receptor, the isoform NH3 of the $Na^+/H^+$ exchanger from renal microvilli membranes and the thromboxane A2 receptor.

Especially preferred are compounds or agents that prevent and/or inhibit the interaction between DP IV and/or DP IV-like enzymes and binding proteins of these enzymes.

According to another embodiment of the present invention, the selectivity and/or activity modifying effectors block the product release site of DP IV and/or DP IV-like enzymes.

Further preferred are selectivity and/or activity modifying effectors, which prevent the tetramerization of DP IV and/or DP IV-like enzymes at the cell surface between a soluble DP IV dimer pair or dimers located on the surface of two different cells in a mammal.

Agents (also called compounds herein) can be pharmacological agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods in the art. If desired, agents can be obtained using any of the numerous combinatorial library methods known in the art, including but not limited to, biological libraries, spatially addressable parallel solid phase or solution phase libraries, synthetic library methods requiring deconvolution, the "one-bead-one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.*, 12, 145, 1997.

Methods for the synthesis of molecular libraries are well known in the art (see, for example, De Witt et al., Proc. Natl. Acad. Sci. USA 90, 6909, 1993; Erb et al. Proc. Natl. Acad. Sci. USA 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. ed. engl. 33, 2061; Gallop et al., J. Med. Chem. 37, 1233, 1994). Libraries of compounds can be present in solution (see, e.g. Houghten, Bio Techniques 13, 412421, 1992) or on beads (Lam, nature 354, 824, 1991) chips (Fodor, Nature 364, 555556, 1993) bacteria or spores (Ladner, U.S. Pat. No. 5,223,409), plasmids (Cull et al., Proc. Natl. Acad. Sci. USA 89, 198651869, 1992), or phage (Scott & Smith, Science 249, 386390, 1990; Devlin, Science 249, 404406, 1990); Cwirla et la., Proc. Natl. Acad. Sci. 97, 63786382, 1990; Felici, J. Mol. Biol. 222, 301310, 1991; and Ladner, U.S. Pat. No. 5,223,409).

High Throughput Screening

Agents can be screened for the ability to bind to DP IV or DP IV-like enzymes or to affect DP IV or DP IV-like enzyme activity using high throughput screening. Using high throughput screening, many discrete compounds can be tested in parallel so that large numbers of agents can be quickly screened. The most widely established techniques utilize 96-well microtiter plates. The well of the microtiter plates typically require assay volumes that range from 50 to 500 µl. In addition to the plates, many instruments, materials, pipettors, robotics, plate washers, and plate readers are commercially available to fit the 96-well format.

Alternatively, "Free format assays", or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. USA 19, 161418 (1994).

Another example of a free format assay is described by Chelsky, "Strategies for Screening Combinatorial Libraries: Novel and Traditional Approaches," reported at the First Annual conference of The Society for Biomolecular Screening in Philadelphia, Pa. (Nov. 710, 1995). Chelsky placed a simple homogenous enzyme assay for carbonic anhydrase inside an agarose gel such that the enzyme in the gel would cause a color change throughout the gel. Thereafter, beads carrying combinatorial compounds were partially released by UV LIGHT. Compounds that inhibited the enzyme were observed as local zones of inhibition having less color change.

Yet another example is described by Salomon et al., Molecular Diversity 2, 5763 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the agent is preferably a small molecule which binds to and occupies, the secondary binding site of DP IV or DP IV-like enzymes, such that normal biological activity is changed or prevented. Examples of such small molecules include, but are not limited to, small peptides or peptide like molecules.

In binding assays, either the agent of DP IV or the DP IV-like enzyme can comprise a detectable label, such as a fluorescent, radioisotopic, chemiluminescent, or the enzyme is labeled, such as horseradish peroxidase, alkaline phosphatase, or luciferase. Detection of an agent, which is bound to DP IV or the DP IV-like enzyme can then be accomplished, for example, by direct counting of radioemission, by scintillation counting, or by determining conversion of an appropriate substrate to a detectable product.

Alternatively, binding of an agent to DP IV or a DP IV-like enzyme can be determined without labelling either of the interactants. For example, a microphysiometer can be used to detect binding of an agent with DP IV or a DP IV-like enzyme. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between an agent and DP IV or a DP IV-like enzyme (McConnel et al., Science 257, 19061912, 1992).

Determining the ability of an agent to bind to DP IV or a DP IV-like enzyme also can be accomplished using a technology such as real-time Biomolecular Interaction Analysis (BIA) (Sjolander & Urbaniczky, Anal. Chem. 63, 23382345, 1991, and Szabo et al., Curr. Opin. Struct. Biol. 5, 699705, 1995) BIA is a technology for studying biospecific interactions in real time, without labelling any of the interactants (e.g. BIA-core™). Changes in the optical phenomenon surface plasmon resonance (SPR) can be used as an indication of real-time reactions between biological molecules.

In yet another aspect of the invention, DP IV or a DP IV-like enzyme can be used as a "bait protein" in a two hybrid assay or three-hybrid assay (see, e.g. U.S. Pat. No. 5,283,317; Zervos et al., Cell 72, 223232, 1993; Madura 920924, 193; Iwabuchi et al., Oncogene 8, 16931696, 1993; and Brent WO94/10300), to identify other proteins which bind to or interact with the DP IV or the DP IV-like enzyme and modulate its activity.

The two hybrid system is based on the modular nature of most transcription factors, which consist of separable DNA binding and activation domains. Briefly, the assay utilizes two different DNA constructs. For example, in one construct, a polynucleotide encoding DP IV or a DP IV-like enzyme can be fused to a polynucleotide encoding the DNA binding domain of a known transcription factor (e.g. GAL4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein dependent complex, the DNA binding and activation domains of the transcription factor are brought into close proximity. This proximity allows transcription of a reporter gene (e.g. LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the dipeptidyl-peptidase IV-like enzyme polypeptide.

It may be desirable to immobilize either the DP IV or DP IV-like enzyme or the agent to facilitate separation of bound from unbound forms of one or both of the interactants, as-well-as to accommodate automation of the assay. Thus, either DP IV or the DP IV-like enzyme or the agent can be bound to a solid support. Suitable solid supports include, but are not limited to, glass or plastic slices, tissue culture plates, microtiter wells, tubes, silicon chips, or particles such as beads (including, but not limited to latex, polysterene, or glass beads). Any method known in the art can be used to attach DP IV or the DP IV-like enzyme or agent to a solid support, including use of covalent and non-covalent linkages, passive absorption, or pairs of binding moieties attached respectively to the polypeptide or agent and the solid support. Agents are preferably bound to the solid support in an array, so that the location of individual test compounds can be tracked. Binding of a test compound to a DP IV or a DP IV-like enzyme can be accomplished in any vessel suitable for containing the reactants. Examples of such vessels include microtiter plates, test tubes, and microcentrifuge tubes.

In one embodiment, the DP IV or DP IV-like enzyme is a fusion protein comprising a domain that allows the DP IV or DP IV-like enzyme to be bound to a solid support. For example, glutathione-S-transferase fusion proteins can be absorbed onto glutathione sepharose beads (Sigma Chemical, St. Louis, Mo.) or glutathione derivatized microtiter plates, which are then combined with the agent and the non-absorbed DP IV or DP IV-like enzyme; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins on a solid support also can be used in the screening assays of the invention. For example, either DP IV or a DP IV-like enzyme or an agent can be immobilized utilizing conjugation of biotin and streptavidin. Biotinylated DP IV or DP IV-like enzymes or agents can be prepared from biotin-NHS-(N-hydroxysuccinimide) using techniques well known in the art (e.g. biotinylation kit, Pierce Chemicals, Rockford, Ill.) and immobilized in the wells of streptavidin-coated 96 well plates (Pierce chemical). Alternatively, antibodies which specifically bind to DP IV, a DP IV-like enzyme or an agent, but which do not interfere with a desired binding site, such as secondary binding site or the active site of DP IV or the DP IV-like enzyme, can be derivatized to the wells of the plate. Unbound targets or proteins can be trapped in the wells by antibody conjugation.

Examples for commercial available antibodies against DP IV or CD26 are for instance:

| Company | Clone | Species (antigen) | Application | Host |
|---|---|---|---|---|
| Coulter | Ta1 | human | IF, FACS | Mouse |
|  | Ba5 | human | FACS |  |
| Biozol | TA59 (Endogen) | human | ICH* |  |
| Pharmingen | M-A216 | human | IF, FACS | Mouse |
| Biotrend | 13.4 | rat | ICH, IF | Mouse |
|  | M-T099 | human | ICH, IF | Mouse |
|  | 134-2C2 | human | IF, FACS | Mouse |
|  | LT-27 | human | IF, FACS | Mouse |
| Biozol | MRCOX-61 | rat | FC | Mouse |
| Biozol | 236.3 | rat | IF, IPrep, IHstaining | Mouse |
| Research Diagnostics | 202.36 | human | IF | Mouse |
| Research Diagnostics | 134-2C2 | human | T-cell signaling, HIV infection | Mouse |

Methods for detecting such complexes, in addition to those described above for the GST-immobilized complexes, include immunodetection of complexes using antibodies which specifically bind to DP IV or DP IV-like enzymes or the agent, enzyme linked assays which rely on detecting an activity of the DP IV or the DP IV-like enzyme, and SDS gel electrophoresis under non-reducing conditions.

Screening for agents which bind to DP IV or a DP IV-like enzyme also can be carried out in an intact cell. Any cell which comprises DP IV or a DP IV-like enzyme can be used in a cell-based assay system. DP IV or a DP IV-like enzyme can be naturally occurring in the cell or can be introduced using techniques such as those described above. Binding of the agents to DP IV or a DP IV-like enzyme is determined as described above.

Enzyme Assays

Agents can be tested for the ability to increase or decrease the activity of a mamalien DP IV or DP IV-like enzyme. DP IV activity can be measured, for example, as described in U.S. Pat. No. 5,601,986 and, specific for the present invention, in examples 1 to 3.

Further on, a screening method for the identification and determination of one or more secondary binding sites on DP IV and/or DP IV-like enzymes is provided.

The screening method for secondary binding site(s) of DP IV and/or DP IV-like enzymes comprises the following steps:
 a) Providing two or more different substrates, each having an amino acid sequence, which binds to DP IV and/or DP IV-like enzymes and aligning the amino acid sequences of said substrates;
 b) Identifying at least one consensus sequence amongst said substrate amino acid sequences;
 c) Synthesizing a peptide having said consensus sequence;
 d) Contacting said synthesized peptide with DP IV and/or a DP IV-like enzyme;
 e) Adding a substrate of DP IV and/or a DP IV-like enzyme to the DP IV and/or DP IV-like enzyme;
 f) Monitoring the biodegradation of the substrate and/or measuring the residual DP IV and/or DP IV-like enzyme activity; and
 g) Correlating changes in said biodegradation and/or enzyme activity with the presence of a secondary binding site capable of modulating the substrate specificity of DP IV and/or DP IV-like enzymes.

Consensus sequences are highly conserved sequence segments. Preferred according to the invention are consensus sequences with the length of 3 to 20 amino acids, more preferred of 5 to 12 amino acids, most preferred 5 to 7 amino acids.

In another illustrative embodiment of the present invention, the agents, which bind to the secondary binding site, e.g. obtained or selected by the screening method described herein, can be used alone or in combination with DP IV-inhibitors for the treatment of any type of DP IV mediated disorders, selected but not restricted to, impaired glucose tolerance, glucosuria, lipid disorders, dyslipidemia, hyperlipidaemia, hypertriglyceridemia, hypercholesterolemia, low HDL levels, high LDL levels, metabolic acidosis, hyperglycemia, diabetes mellitus, diabetic neuropathy and nephropathy and of sequelae caused by diabetes mellitus in mammals, metabolism-related hypertension and cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, Syndrome X, ovarian hyperandrogenism (polycystic ovarian syndrome), growth hormone deficiency, neutropenia, tumor metastasis, benign prostatic hypertrophy, gingivitis, osteoporosis, and other conditions.

Agents such as N-(N'-substituted glycyl)-2-cyanopyrrolidines, L-threo-isoleucyl thiazolidine (P32/98), L-allo-isoleucyl thiazolidine, L-threo-isoleucyl pyrrolidine, and L-allo-isoleucyl pyrrolidine have been developed which inhibit the enzymatic activity of DP IV and are described in U.S. Pat. No. 6,001,155, WO 99/61431, WO 99/67278, WO 99/67279, DE 198 34 591, WO 97/40832, DE 196 16 486 C 2, WO 98/19998, WO 00/07617, WO 99/38501, and WO 99/46272.

Further examples of low molecular weight dipeptidyl peptidase IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, amino-acyl-borono-prolyl-inhibitors and cyclopropyl-fused pyrrolidines. Inhibitors of dipeptidyl peptidase IV are described in U.S. Pat. Nos. 6,380,398, 6,011,155; 6,107,317; 6,110,949; 6,124,305; 6,172,081; and WO 95/15309, WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, WO 02/04610, WO 02/051836, WO 02/068420, WO 02/076450; WO 02/083128, WO 02/38541, WO 03/000180, WO 03/000181, WO 03/000250, WO 03/002530, WO 03/002531, WO 03/002553, WO 03/002593, WO 03/004496, WO 03/004498, WO 03/024965, WO 03/024942, WO 03/035067, WO 03/037327, WO 03/035057, WO 03/045977, WO 03/055881, WO 03/68748, WO 03/68757, WO 03/057666, WO 03057144, WO 03/040174 and WO 03/033524, the teachings of which are herein incorporated by reference in their entirety concerning these inhibitors, their uses, definition and their production. The goal of these agents is to inhibit DP IV, and by doing so, to relieve effectively any type of DP IV-mediated disease. The inventors of the present invention have surprisingly found that such agents can be advantageously employed for an entirely different therapeutic purpose, then previously known by those skilled in the art.

Preferred for the use in combination with agents binding to the secondary binding site of DP IV or DP IV-like enzymes are DP IV-inhibitors such as valine pyrrolidide (Novo Nordisk), NVP-DPP728A (1-[[[2-[{5-cyanopyridin-2-yl}amino]ethyl]amino]acetyl]-2-cyano-(S)-pyrrolidine) (Novartis) as disclosed by Hughes et al., Biochemistry, 38 (36), 11597-11603, 1999, LAF-237 (1-[(3-hydroxy-adamant-1-ylamino)-acetyl]-pyrrolidine-2(S)-carbonitrile); disclosed by Hughes et al., Meeting of the American Diabetes Association 2002, Abstract no. 272 or (Novartis), TSL-225 (tryptophyl-1,2,3,4-tetrahydroisoquinoline-3-carboxylic acid), disclosed by Yamada et. al., Bioorg. & Med. Chem. Lett. 8 (1998), 1537-1540, 2-cyanopyrrolidides and 4-cyanopyrrolidides as disclosed by Asworth et al., Bioorg. & Med. Chem. Lett., 6, No. 22, pp 1163-1166 and 2745-2748 (1996), FE-999011, disclosed by Sudre et al., Diabetes 51 (5), pp 1461-1469 (2002) (Ferring) and the compounds disclosed in WO 01/34594 (Guilford), employing dosages as set out in the above references.

In one especially illustrative embodiment, the present invention relates to the use of agents, which bind to the secondary binding site(s) of DP IV or DP IV-like enzymes in combination with dipeptide-like compounds and compounds analogous to dipeptide compounds that are formed from an amino acid and a thiazolidine or pyrrolidine group, and salts thereof, referred to hereinafter as dipeptide-like compounds. Preferably the amino acid and the thiazolidine or pyrrolidine group are bonded with an amide bond.

Especially suitable for that purpose according to the invention are dipeptide-like compounds in which the amino acid is preferably selected from a natural amino acid, such as, for example, leucine, valine, glutamine, glutamic acid, proline, isoleucine, asparagines and aspartic acid.

The dipeptide-like compounds used according to the invention exhibit at a concentration (of dipeptide compounds) of 10 μM, a reduction in the activity of plasma dipeptidyl peptidase IV or DP IV-analogous enzyme activities of at least 10%, especially of at least 40%. Frequently a reduction in activity of at least 60% or at least 70% is also required. Preferred agents may also exhibit a reduction in activity of a maximum of 20% or 30%.

Preferred compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine of formulas 1 and 2:

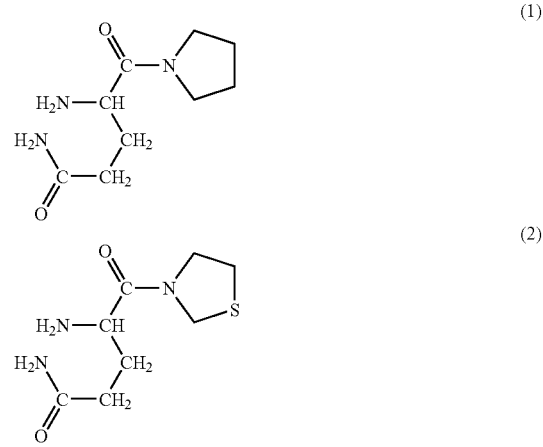

Further preferred compounds are given in Table 6.

The salts of the dipeptide-like compounds can be present in a molar ratio of dipeptide (-analogous) component to salt component of 1:1 or 2:1. Such a salt is, for example, (Ile-Thia)$_2$ fumaric acid.

TABLE 6

Structures of further preferred dipeptide compounds
DP IV-inhibitor

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine In another preferred embodiment, the present invention provides the use of agents binding to the secondary binding site(s) of DP IV or DP IV-like enzymes in combination with substrate-like peptide compounds of formula 3 useful for competitive modulation of dipeptidyl peptidase IV catalysis:

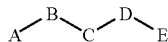 (3)

wherein

A, B, C, D and E are independently any amino acid moieties including proteinogenic amino acids, non-proteinogenic amino acids, L-amino acids and D-amino acids and wherein E and/or D may be absent.

Further conditions regarding formula (3):

A is an amino acid except a D-amino acid,

B is an amino acid selected from Pro, Ala, Ser, Gly, Hyp, acetidine-(2)-carboxylic acid and pipecolic acid, C is any amino acid except Pro, Hyp, acetidine-(2)-carboxylic acid, pipecolic acid and except N-alkylated amino acids, e.g. N-methyl valine and sarcosine, D is any amino acid or missing, and E is any amino acid or missing, or:

C is any amino acid except Pro, Hyp, acetidine-(2)-carboxylic acid, pipecolic acid, except N-alkylated amino acids, e.g. N-methyl valine and sarcosine, and except a D-amino-acid;

D is any amino acid selected from Pro, Ala, Ser, Gly, Hyp, acetidine-(2)-carboxylic acid and pipecolic acid, and E is any amino acid except Pro, Hyp, acetidine-(2)-carboxylic acid, pipecolic acid and except N-alkylated amino acids, e.g. N-methyl valine and sarcosine.

Examples of amino acids which can be used in the present invention are: L and D-amino acids, N-methyl-amino-acids; allo- and threo-forms of Ile and Thr, which can, e.g. be α-, β- or ω-amino acids, whereof α-amino acids are preferred.

Examples of amino acids throughout the claims and the description are: aspartic acid (Asp), glutamic acid (Glu), arginine (Arg), lysine (Lys), histidine (His), glycine (Gly), serine (Ser) and cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-amino octanoic acid (Aoa), azetidine-(2)-carboxylic acid (Ace), pipecolic acid (Pip), 3-amino propionic, 4-amino butyric and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), Acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-Amino-4-cyanobutyric acid (Cba), cycloalkane-carboxylic acids.

Examples of ω-amino acids are e.g.: 5-Ara (aminoraleric acid), 6-Ahx (aminohexanoic acid), 8-Aoc (aminooctanoic aicd), 9-Anc (aminovanoic aicd), 10-Adc (aminodecanoic acid), 11-Aun (aminoundecanoic acid), 12-Ado (aminododecanoic acid).

Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal), (2-Nal), 4-aminophenylalanin (Phe(4-$NH_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-$Cl_2$)), 3-fluorophenylalanine (Phe(3-F)), 4-fluorophenylalanine (Phe(4-F)), 3,4-fluorophenylalanine (Phe(3, 4-$F_2$)), pentafluorophenylalanine (Phe($F_5$)), 4-guanidinophenylalanine (Phe(4-guanidino)), homophenylalanine (hPhe), 3-jodophenylalanine (Phe(3-J)), 4 jodophenylalanine (Phe(4-J)), 4-methylphenylalanine (Phe(4-Me)), 4-nitrophenylalanine (Phe-4-$NO_2$)), biphenylalanine (Bip), 4-phosphonomehtylphenylalanine (Pmp), cyclohexyglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-$J_2$)), d-methyl-tyrosine (Tyr(Me)), 3-$NO_2$-tyrosine (Tyr(3-$NO_2$)), phosphotyrosine (Tyr($PO_3H_2$)), alkylglycine, 1-aminoindane-1-carboxy acid, 2-aminoindane-2-carboxy acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly($NH_2$)), diaminobutyric acid (Dab), 1,3-dihydro-2H-isoinole-carboxylic acid (Disc), homocylcohexylalanin (hCha), homophenylalanin (hPhe oder Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha).

Other amino acid substitutions for those encoded in the genetic code can also be included in peptide compounds within the scope of the invention and can be classified within this general scheme.

Proteinogenic amino acids are defined as natural protein-derived α-amino acids. Non-proteinogenic amino acids are defined as all other amino acids, which are not building blocks of common natural proteins.

The resulting peptides may be synthesized as the free C-terminal acid or as the C-terminal amide form. The free acid peptides or the amides may be varied by side chain modifications. Such side chain modifications include for instance, but are not restricted to, homoserine formation, pyroglutamic acid formation, disulphide bond formation, deamidation of asparagine or glutamine residues, methylation, t-butylation, t-butyloxycarbonylation, 4-methylbenzylation, thioanysilation, thiocresylation, benzyloxymethylation, 4-nitrophenylation, benzyloxycarbonylation, 2-nitrobencoylation, 2-nitrosulphenylation, 4-toluenesulphonylation, pentafluorophenylation, diphenylmethylation, 2-chlorobenzyloxycarbonylation, 2,4,5-trichlorophenylation, 2-bromobenzyloxycarbonylation, 9-fluorenylmethyloxycarbonylation, triphenylmethylation, 2,2,5,7,8,-pentamethylchroman-6-sulphonylation, hydroxylation, oxidation of methionine, formylation, acetylation, anisylation, benzylation, bencoylation, trifluoroacetylation, carboxylation of aspartic acid or glutamic acid, phosphorylation, sulphation, cysteinylation, glycolysation with pentoses, deoxyhexoses, hexosamines, hexoses or N-acetylhexosamines, farnesylation, myristolysation, biotinylation, palmitoylation, stearoylation, geranylgeranylation, glutathionylation, 5'-adenosylation, ADP-ribosylation, modification with N-glycolylneuraminic acid, N-acetylneuraminic acid, pyridoxal phosphate, lipoic acid, 4'-phosphopantetheine, or N-hydroxysuccinimide.

In the compounds of formula (3), the amino acid moieties A, B, C, D, and E are respectively attached to the adjacent moiety by amide bonds in a usual manner according to standard nomenclature so that the amino-terminus (N-terminus) of the amino acids (peptide) is drawn on the left and the carboxyl-terminus of the amino acids (peptide) is drawn on the right. (C-terminus).

Until the present invention by Applicants, known peptide substrates of the proline-specific serine protease dipeptidyl peptidase IV in vitro are the tripeptides Diprotin A (Ile-Pro-Ile), Diprotin B (Val-Pro-Leu) and Diprotin C (Val-Pro-Ile). Applicants have unexpectedly discovered that the compounds disclosed herein above and below act as substrates of dipeptidyl peptidase IV in vivo in a mammal and, in pharmacological doses, improve insulin sensitivity and islet signaling and alleviate pathological abnormalities of the metabolism of mammals such as glucosuria, hyperlipidaemia, metabolic acidosis and diabetes mellitus by competitive catalysis.

Preferred peptide compounds are listed in table 7.

TABLE 7

Examples of peptide substrates

| Peptide | Mass (calc.) | Mass (exp.)[1] [M+H$^+$] |
|---|---|---|
| 2-Amino octanoic acid-Pro-Ile | 369.5 | 370.2 |
| Abu-Pro-Ile | 313.4 | 314.0 |
| Aib-Pro-Ile | 313.4 | 314.0 |
| Aze-Pro-Ile | 311.4 | 312.4 |
| Cha-Pro-Ile | 381.52 | 382.0 |
| Ile-Hyp-Ile | 356.45 | 358.2 |
| Ile-Pro-allo-Ile | 341.4 | 342.0 |
| Ile-Pro-t-butyl-Gly | 341.47 | 342.36 |
| Ile-Pro-Val | 327.43 | 328.5 |
| Nle-Pro-Ile | 341.45 | 342.2 |
| Nva-Pro-Ile | 327.43 | 328.2 |
| Orn-Pro-Ile | 342.42 | 343.1 |
| Phe-Pro-Ile | 375.47 | 376.2 |
| Phg-Pro-Ile | 361.44 | 362.2 |
| Pip-Pro-Ile | 338.56 | 340.0 |
| Ser(Bzl)-Pro-Ile | 405.49 | 406.0 |
| Ser(P)-Pro-Ile | 395.37 | 396.0 |
| Ser-Pro-Ile | 315.37 | 316.3 |
| t-butyl-Gly-Pro-D-Val | 327.4 | 328.6 |
| t-butyl-Gly-Pro-Gly | 285.4 | 286.3 |
| t-butyl-Gly-Pro-Ile | 341.47 | 342.1 |
| t-butyl-Gly-Pro-Ile-amide | 340.47 | 341.3 |
| t-butyl-Gly-Pro-t-butyl-Gly | 341.24 | 342.5 |
| t-butyl-Gly-Pro-Val | 327.4 | 328.4 |
| Thr-Pro-Ile | 329.4 | 330.0 |
| Tic-Pro-Ile | 387.46 | 388.0 |
| Trp-Pro-Ile | 414.51 | 415.2 |
| Tyr(P)-Pro-Ile | 471.47 | 472.3 |
| Tyr-Pro-allo-Ile | 391.5 | 392.0 |
| Val-Pro-allo-Ile | 327.4 | 328.5 |
| Val-Pro-t-butyl-Gly | 327.4 | 328.15 |
| Val-Pro-Val | 313.4 | 314.0 |

[1][M+H$^+$] were determined by Electrospray mass spectrometry in positive ionization mode.

t-butyl-Gly is defined as:

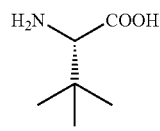

Ser(Bzl) and Ser(P) are defined as benzyl-serine and phosphoryl-serine, respectively. Tyr(P) is defined as phosphoryl-tyrosine.

Further preferred compounds, which can be used according to the present invention in combination with agents binding to the secondary binding site(s) of DP IV or DP IV-like enzymes, are peptidylketones of formula 4:

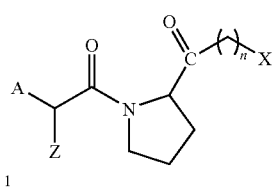

(4)

n = 0, 1 and pharmaceutically acceptable salts thereof, wherein:
A is selected from the following structures:

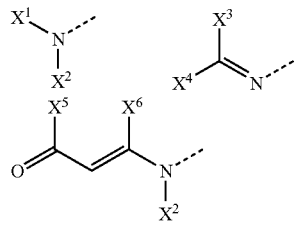

wherein
X$^1$ is H or an acyl or oxycarbonyl group including an amino acid residue, N-protected amino acid residue, a peptide residue or a N-protected peptide residue, X$^2$ is H, —(CH)$_m$—NH—C$_5$H$_3$N—Y with m=2-4 or —C$_5$H$_3$N—Y (a divalent pyridyl residue) and Y is selected from H, Br, Cl, I, NO$_2$ or CN, X$^3$ is H or selected from an alkyl-, alkoxy-, halogen-, nitro-, cyano- or carboxy-substituted phenyl or from an alkyl-, alkoxy-, halogen-, nitro-, cyano- or carboxy-substituted pyridyl residue, X$^4$ is H or selected from an alkyl-, alkoxy-, halogen-, nitro-, cyano- or carboxy-substituted phenyl or from an alkyl-, alkoxy-, halogen-, nitro-, cyano- or carboxy-substituted pyridyl residue, X$^5$ is H or an alkyl, alkoxy or phenyl residue,
X$^6$ is H or an alkyl residue,
for n=1
X is selected from: H, OR$^2$, SR$^2$, NR$^2$R$^3$, N$^+$R$^2$R$^3$R$^4$, wherein:
R$^2$ stands for acyl residues, which are optionally substituted with alkyl, cycloalkyl, aryl or heteroaryl residues, or for amino acid residues or peptidic residues, or alkyl residues, which are optionally substituted with alkyl, cycloalkyl, aryl or heteroaryl residues, R³ stands for alkyl or acyl residues, wherein R² and R³ may be part of a saturated or unsaturated carbocyclic or heterocyclic ring, R⁴ stands for alkyl residues, wherein R² and R⁴ or R³ and R⁴ may be part of a saturated or unsaturated carbocyclic or heterocyclic ring, for n=0

X is selected from:

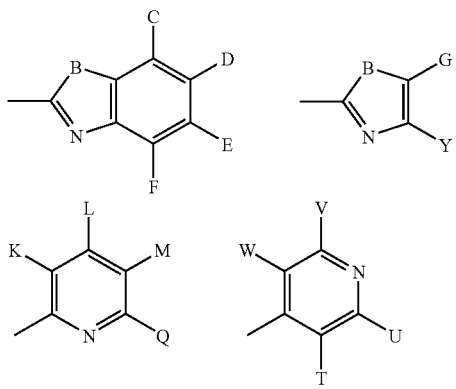

wherein

B stands for: O, S or NR⁵, wherein R⁵ is H, alkyl or acyl,

C, D, E, F, G, Y, K, L, M, Q, T, U, V and W are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In preferred compounds of formula 4, A is

wherein

X¹ is H or an acyl or oxycarbonyl group including an amino acid residue, N-acylated amino acid residue, a peptide residue from di- to pentapeptides, preferably a dipeptide residue, or a N-protected peptide residue from di- to pentapeptides, preferably a N-protected dipeptide residue X² is H, —(CH)$_m$—NH—$C_5H_3N$—Y with m=2-4 or —$C_5H_3N$—Y (a divalent pyridyl residue) and Y is selected from H, Br, Cl, I, $NO_2$ or CN, for n=1

X is preferably selected from: H, OR², SR², NR²R³, wherein:

R² stands for acyl residues, which are optionally substituted with alkyl, cycloalkyl, aryl or heteroaryl residues, or for amino acid residues or peptidic residues, or alkyl residues, which are optionally substituted with alkyl, cycloalkyl, aryl or heteroaryl residues, R³ stands for alkyl or acyl residues, wherein R² and R³ may be part of a saturated or unsaturated carbocyclic or heterocyclic ring, for n=0

X is preferably selected from:

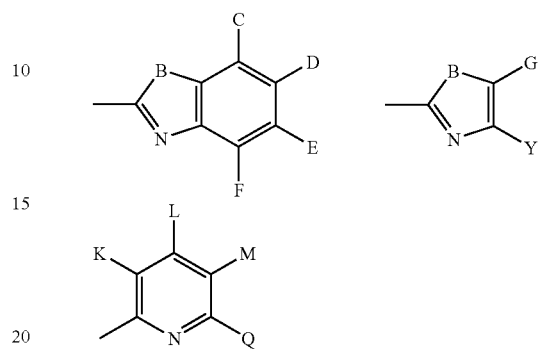

wherein

B stands for: O, S or NR⁵, wherein R⁵ is H, alkyl or acyl,

C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In more preferred compounds of formula 4, A is

wherein

X¹ is H or an acyl or oxycarbonyl group including an amino acid residue, N-acylated amino acid residue or a peptide residue from di- to pentapeptides, preferably a dipeptide residue, or a N-protected peptide residue from di- to pentapeptides, preferably a N-protected dipeptide residue for n=1, X is preferably selected from: H, OR², SR², wherein:

R² stands for acyl residues, which are optionally substituted with alkyl or aryl residues, for n=0

X is preferably selected from:

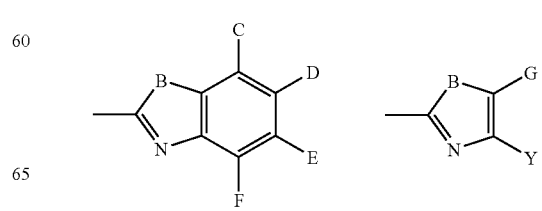

-continued

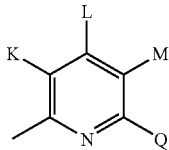

wherein

B stands for: O, S or $NR^5$, wherein $R^5$ is H, alkyl or acyl, C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In most preferred compounds of formula 4, A is

wherein $X^1$ is H or an acyl or oxycarbonyl group including an amino acid residue, N-acylated amino acid residue or a dipeptide residue, containing a Pro or Ala in the penultimate position, or a N-protected dipeptide residue containing a Pro or Ala in the penultimate position, for n=1, X is H, for n=0

X is preferably selected from:

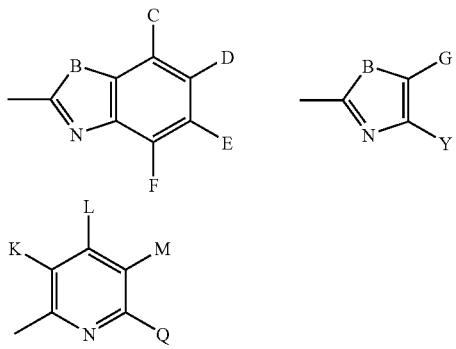

wherein

B stands for: O or S, most preferably for S

C, D, E, F, G, Y, K, L, M, Q, are H and

Z is selected from H, or a branched or straight chain alkyl residue from $C_3$-$C_5$, a branched or straight chain alkenyl residue from $C_2$-$C_9$, a cycloalkyl residue from $C_5$-$C_7$, a cycloalkenyl residue from $C_5$-$C_7$, an aryl or heteroaryl residue, or a side chain selected from all side chains of all natural amino acids or derivatives thereof.

Most preferred for Z is H.

According to a preferred embodiment the acyl groups are $C_1$-$C_6$-acyl groups.

According to a further preferred embodiment the alk(yl) groups are $C_1$-$C_6$-alk(yl) groups, which may be branched or unbranched.

According to a still further preferred embodiment the alkoxy groups are $C_1$-$C_6$-alkoxy groups.

According to yet another preferred embodiment the aryl residues are $C_5$-$C_{12}$ aryl residues that have optionally fused rings.

According to a still further preferred embodiment the cycloalkyl residues (carbocycles) are $C_3$-$C_8$-cycloalkyl residues.

According to another preferred embodiment the heteroaryl residues are $C_4$-$C_{11}$ aryl residues that have optionally fused rings and, in at least one ring, additionally from 1 to 4 preferably 1 or 2 hetero atoms, such as O, N and/or S.

According to a further preferred embodiment peptide residues are corresponding residues containing from 2 to 50 amino acids.

According to another preferred embodiment the heterocyclic residues are $C_2$-$C_7$-cycloalkyl radicals that additionally have from 1 to 4, preferably 1 or 2 hetero atoms, such as O, N and/or S.

According to a still further preferred embodiment the carboxy groups are $C_1$-$C_6$ carboxy groups, which may be branched or unbranched.

According to yet another preferred embodiment the oxycarbonyl groups are groups of the formula —O—$(CH_2)_{1-6}$COOH.

The amino acids can be any natural or synthetic amino acid, preferably natural alpha amino acids.

Preferred compounds of formula (4) are 2-Methylcarbonyl-1-N-[(L)-Alanyl-(L)-Valinyl]-(2S)-pyrrolidine hydrobromide; 2-Methyl)carbonyl-1-N-[(L)-Valinyl-(L)-Prolyl-(L)-Valinyl]-(2S)-pyrrolidine hydrobromide; 2-[(Acetyl-oxy-methyl)carbonyl]-1-N-[(L)-Alanyl-(L)-Valinyl]-(2S)-pyrrolidine hydrobromide; 2-[Benzoyl-oxy-methyl)carbonyl]-1-N-[{(L)-Alanyl}-(L)-Valinyl]-(2S)-pyrrolidine hydrobromide; 2-{[(2,6-Dichlorbenzyl)thiomethyl]carbonyl}-1-N-[{(L)-Alanyl}-(L)-Valinyl]-(2S)-pyrrolidine; 2-[Benzoy-loxy-methyl)carbonyl]-1-N-[Glycyl-(L)-Valinyl]-(2S)-pyrrolidine hydrobromide; 2-[([1,3]-thiazole-2-yl)carbonyl]-1-N-[{(L)-Alanyl}-(L)-Valinyl]-(2S)-pyrrolidine trifluoracetat; 2-[(benzothiazole-2-yl)carbonyl]-1-N-[N-{(L)-Alanyl}-(L)-Valinyl]-(2S)-pyrrolidin trifluoracetat; 2-[(-benzothiazole-2-yl)carbonyl]-1-N-[{(L)-Alanyl}-Glycyl]-(2S)-pyrrolidine trifluoracetat; 2-[(pyridin-2-yl)carbonyl]-1-N-[N-{(L)-Alanyl}-(L)-Valinyl]-(2S)-pyrrolidine trifluoracetat.

Further, according to the present invention compounds of formula (5) including all stereoisomers and pharmaceutical acceptable salts thereof can be used in combination with agents binding to the secondary binding site(s) of DP IV or DP IV-like enzymes:

$$B—(CH—R^1)_n—C(=X^2)-D \quad (5)$$

wherein n is 0 or 1, $R^1$ stands for H, $C_1$-$C_9$ branched or straight chain alkyl, preferably H, n-butan-2-yl, n-prop-2-yl or isobutyl, $C_2$-$C_9$ branched or straight chain alkenyl, $C_3$-$C_8$ cycloalkyl, preferably cyclohexyl, $C_5$-$C_7$ cycloalkenyl, aryl, heteroaryl or a side chain of a natural amino acid or mimetics thereof, $X^2$ stands for O, $NR^6$, $N^+(R^7)_2$, or S, B is selected from the following groups:

$$X^5\text{-}N(R^5)\text{-}$$

$$Z\text{-}C(W)=N\text{-}$$

$$W^1\text{-}C(O)\text{-}C=C(Z^1)\text{-}N(R^5)\text{-}$$

$$R^3,R^4\text{-tetrahydroisoquinoline-NH}$$

$$R^3,R^4\text{-decahydroisoquinoline-NH}$$

where $X^5$ is H or an acyl or oxycarbonyl group including amino acids, $R^5$ is H, $C_1$-$C_9$ branched or straight chain alkyl, preferably H, n-butan-2-yl, n-prop-2-yl or isobutyl, $C_2$-$C_9$ branched or straight chain alkenyl, $C_3$-$C_8$ cycloalkyl, preferably cyclohexyl, 3-hydroxyadamant-1-yl, $C_5$-$C_7$ cycloalkenyl, aryl, heteroaryl or a side chain of a natural amino acid or derivatives thereof, or a group of the formula —$(CH)_m$—NH—$C_5H_3N$—Y where m is an integer of 2-4, —$C_5H_3N$—Y is a divalent pyridyl moiety and Y is a hydrogen atom, a halogen atom, a nitro group or a cyano group, $R^6$, $R^7$ $R^8$ and $R^9$ are independently selected from H, optionally substituted $C_1$-$C_9$ branched or straight chain alkyl, preferably an optionally substituted $C_2$-$C_5$ branched or straight chain alkyl; or optionally substituted $C_2$-$C_9$ branched or straight chain alkenyl, preferably an $C_2$-$C_5$ branched or straight chain alkenyl; or optionally substituted $C_3$-$C_8$ cycloalkyl, preferably an optionally substituted $C_4$-$C_7$ cycloalkyl; or an optionally substituted $C_5$-$C_7$ cycloalkenyl, or an optionally substituted aryl residue, Z is selected from H, pyridyl or optionally substituted phenyl, optionally substituted alkyl groups, alkoxy groups, halogens, nitro, cyano and carboxy groups, W is selected from H, pyridyl or optionally substituted phenyl, optionally substituted alkyl groups, alkoxy groups, halogens, nitro, cyano and carboxy groups, $W^1$ is H or optionally substituted alkyl, alkoxy or optionally substituted phenyl, and $Z^1$ is H, or optionally substituted alkyl, $R^3$ and $R^4$ are independently H, hydroxy, alkyl, alkoxy, aralkoxy, nitro, cyano or halogen, D is an optionally substituted compound of the formula $$(X^8)_{0-1}\text{-}X^9\text{-}X^{10}\text{-}X^{11}\text{-}X^{12}$$

which can be saturated, or can have one, two or three double bonds, wherein $X^8$ to $X^{11}$ are independently CH, N, $N^+(R^7)$, or $CR^8$, if unsaturated, or $X^8$ to $X^{11}$ are independently $CH_2$, NH, $NH^+(R^7)$, O, or S if saturated, $X^{12}$ is CHA, NA, $CH_2$, NH, $NH^+$(R or $CHR^8$, if saturated or $X^{12}$ is CA, $NA^+$, CH, N, $N^+(R^7)$, or $CR^8$, if unsaturated and A is H or an isoster of a carboxylic acid such as CN, $SO_3H$, CONOH, $PO_3R^5R^6$, a tetrazole, an amide, an ester or an acid anhydride.

Throughout the application, D contains preferably at most two, further preferred at most one hetero atom in the ring.

According to preferred embodiments of the present invention, D stands for optionally substituted $C_4$-$C_7$ cycloalkyl, preferably $C_4$-$C_6$ cycloalkyl, optionally substituted $C_4$-$C_7$ cycloalkenyl, or optionally substituted (hetero)cycloalkyl of the formulae $$X^9\text{-}X^{10}\text{-}X^{11}\text{-}X^{12}$$

wherein the residues are as defined above, or $$X^9=X^{10}\text{-}X^{11}\text{-}X^{12}$$

that is, a five-membered ring containing one or two double bonds in the ring, wherein the residues are as defined above, or $$X^9\text{-}X^{10}\text{-}X^{11}\text{-}X^{12}$$ (six-membered ring)

wherein the residues are as defined above, or $$X^8\text{-}X^9\text{-}X^{10}\text{-}X^{11}\text{-}X^{12}$$

wherein the residues are as defined above,
or

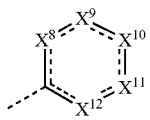

that is a six-membered ring containing one or two double bonds in the ring, wherein the residues are as defined above,
or

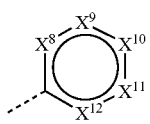

wherein the residues are as defined above.

According to a preferred embodiment, B has the following formula:

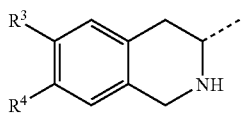

wherein the residues are as defined above.

According to another preferred embodiment, B has the following formula:

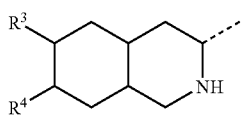

wherein the residues are as defined above.

Preferred compounds according to formula (5) are
1-cyclopentyl-3-methyl-1-oxo-2-pentanaminium chloride,
1-cyclopentyl-3-methyl-1-oxo-2-butanaminium chloride,
1-cyclopentyl-3,3-dimethyl-1-oxo-2-butanaminium chloride,
1-cyclohexyl-3,3-dimethyl-1-oxo-2-butanaminium chloride,
3-(cyclopentylcarbonyl)-1,2,3,4-tetrahydroisoquinolinium chloride, and N-(2-cyclopentyl-2-oxoethyl)cyclohexanaminium chloride.

Because of the wide distribution of the protein in the body and the wide variety of mechanisms involving DP IV, DP IV-activity and DP IV-related proteins, systemic therapy (enteral or parenteral administration) with DP IV-inhibitors can result in a series of undesirable side-effects.

The problem to be solved was moreover, to provide compounds that can be used, in combination with agents binding to the secondary binding site(s) of DP IV or DP IV-like enzymes, for targeted influencing of locally limited patho-physiological and physiological processes. The problem of the invention especially consists in obtaining locally limited and highly specific inhibition of DP IV or DP IV-analogous activity for the purpose of targeted intervention in the regulation of the activity of locally active substrates.

This problem is solved according to the invention by the use compounds of the general formula (6) in combination with agents binding to the secondary binding site(s) of DP IV or DP IV-like enzymes:

wherein
A is an amino acid having at least one functional group in the side chain,
B is a chemical compound covalently bound to at least one functional group of the side chain of A,
C is a thiazolidine, pyrrolidine, cyanopyrrolidine, hydroxyproline, dehydroproline or piperidine group amide-bonded to A.

In accordance with a preferred embodiment of the invention, pharmaceutical compositions are used comprising at least one compound of the general formula (6) and at least one customary adjuvant appropriate for the site of action.

Preferably A is an α-amino acid, especially a natural α-amino acid having one, two or more functional groups in the side chain, preferably threonine, tyrosine, serine, arginine, lysine, aspartic acid, glutamic acid or cysteine.

Preferably B is an oligopeptide having a chain length of up to 20 amino acids, a polyethylene glycol having a molar mass of up to 20 000 g/mol, an optionally substituted organic amine, amide, alcohol, acid or aromatic compound having from 8 to 50 C atoms.

Despite an extended side chain function, the compounds of formula (6) can still bind to the active centre of the enzyme dipeptidyl peptidase IV and analogous enzymes but are no longer actively transported by the peptide transporter PepT1. The resulting reduced or greatly restricted transportability of the compounds according to the invention leads to local or site directed inhibition of DP IV and DP IV-like enzyme activity.

By extending/expanding the side chain modifications, for example beyond a number of seven carbon atoms, it is accordingly possible to obtain a dramatic reduction in transportability. With increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

Preferred compounds of formula (6) are compounds, wherein the oligopeptides have chain lengths of from 3 to 15, especially from 4 to 10, amino acids, and/or the polyethylene glycols have molar masses of at least 250 g/mol, preferably of at least 1500 g/mol and up to 15 000 g/mol, and/or the optionally substituted organic amines, amides, alcohols, acids or aromatic 20 compounds have at least 12 C atoms and preferably up to 30 C atoms.

The compounds of the present invention can be converted into and used as acid addition salts, especially pharmaceutically acceptable acid addition salts. The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methane-sulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of formulas (1) to (6) are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The present invention further includes within its scope prodrugs of the compounds of formulas (1) to (6). In general, such prodrugs will be functional derivatives of the compounds which are readily convertible in vivo into the desired therapeutically active compound. Thus, in these cases, the present invention shall encompass the treatment of the various disorders described with prodrug versions of one or more of the claimed compounds, which convert to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113 and DE 198 28 114, which are fully incorporated herein by reference.

Where the compounds or prodrugs according to this invention have at least one chiral center, they may accordingly exist as enantiomers. Where the compounds or prodrugs possess two or more chiral centers, they may additionally exist as diastereomers. It is to be understood that all such isomers and mixtures thereof are encompassed within the scope of the present invention. Furthermore, some of the crystalline forms of the compounds or prodrugs may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

A further preferred embodiment of the present invention comprises compounds capable of binding to the secondary binding site of DP IV or DP IV-like enzymes according to any one of the embodiments of the present invention
   in combination with acarbose, or
   in combination with metformin; or
   in combination with acarbose and metformin.

In a further preferred embodiment, the compounds capable of binding to the secondary binding site of DP IV and/or DP IV-like enzymes of the present invention, can be used in combination with at least one antidiabetic agent selected from the group consisting of:
   insulin sensitizers selected from the group consisting of
     PPAR agonists,
     biguanides, and
     protein tyrosin phosphatase-1B (PTP-1B) inhibitors;
   insulin and insulin mimetics;
   sulfonylureas and other insulin secretagogues;
   α-glucosidase inhibitors, e.g. acarbose;
   glucagon receptor agonists;
   GLP-1; GLP-1 mimetics, and GLP-1 receptor agonists;
   GLP-2; GLP-2 mimetics, and GLP-2 receptor agonists, e.g. ALX-600 (teduglutide from NPS Allelix Corp.);
   exendin-4 and exendin-4 mimetics, e.g. exenatide (AC-2993, synthetic exendin-4 from Amylin/Eli Lilly);
   GIP, GIP mimetics, and GIP receptor agonists;
   PACAP, PACAP mimetics, and PACAP receptor 3 agonists;
   PYY, PYY mimetics, PYY receptor agonists, and PYY receptor antagonists,
   cholesterol lowering agents selected from the group consisting of
     HMG-CoA reductase inhibitors,
     sequestrants,
     nicotinyl alkohol, nicotinic acid and salts thereof,
     PPARα agonists,
     PPARγ agonists,
     PPARα/γ dual agonists,
     inhibitors of cholesterol absorption,
     acyl CoA:cholesterol acyltransferase inhibitors, and
     antioxidants;
   PPARδ agonists;
   antiobesity compounds;
   an ileal bile acid transporter inhibitor; and
   anti-inflammatory agents.

A further preferred embodiment of the present invention comprises compounds capable of binding to the secondary binding site of DP IV or DP IV-like enzymes according to any one of the embodiments of the present invention mentioned above
   in combination with a gene therapeutic expression system for GLP-1 comprising a viral vector comprising
     (a) a polynucleotide sequence encoding GLP-1 (gluacogen like peptide-1); and
     (b) a polynucleotide sequence encoding a signal sequence upstream of (a); and
     (c) a polyadenylation signal downstream of (a); and
     (d) a polynucleotide sequence encoding a proteolytic cleavage site located between the polynucleotide sequence encoding GLP-1 and the polynucleotide sequence encoding the signal sequence; and
     (e) wherein the expression of GLP-1 underlies a constitutive promoter or is controlled by a regulatable promotor;
     (f) wherein, optionally, the viral vector comprises a polynucleotide sequence encoding GIP (glucose dependent insulinotropic peptide);
     (g) wherein, optionally, the viral vector is encompassed by a mammalian cell.

and/or
   in combination with a gene therapeutic expression system for GIP comprising a viral vector comprising
     (a) a polynucleotide sequence encoding GIP (glucose dependent insulinotropic peptide); and
     (b) a polynucleotide sequence encoding a signal sequence upstream of (a); and
     (c) a polyadenylation signal downstream of (a); and
     (d) a polynucleotide sequence encoding a proteolytic cleavage site located between the polynucleotide sequence encoding GIP and the polynucleotide sequence encoding the signal sequence; and
     (e) wherein the expression of GIP underlies a constitutive promoter or is controlled by a regulatable promotor;

(f) wherein, optionally, the viral vector comprises a polynucleotide sequence encoding GLP-1 (glucagon like peptide 1);

(g) wherein, optionally, the viral vector is encompassed by a mammalian cell.

A further preferred embodiment of the present invention comprises the compounds capable of binding to the secondary binding site of DP IV or DP IV-like enzymes in combination with a gene therapeutic expression system for GLP-1 and/or GIP according to any one of the embodiments of the present invention mentioned above wherein
the signal sequence upstream of the gene of interest (GLP-1; GIP) is the murine immunoglobulin κ signal sequence or the glia monster exendin signal sequence; and/or
the polyadenylation signal downstream of the gene of interest (GLP-1; GIP) is derived from simian viraus 40 (SV 40); and/or
the proteolytic cleavage site is cleaved by furin preotease; and/or
the gene delivery vector for expression the gene of interest is an adenoviral, retroviral, leniviral, adeno associated viral vector; and /or
the constitutive promoter is a cytomegalovirus (CMV) promotor, or a Rous sarcoma long-terminal repeat (LTR) sequence, and the SV 40 early gene promoter; and the inducible promoter is the Tet-On™/Tet-Off™ system available from Clontech; and/or
the mammalian cell is a primate or rodent cell, preferably a human cell, more preferably a human hepatocyte.

In a further illustrative embodiment, the present invention provides formulations for agents binding to the secondary binding site of DP IV or DP IV-like enzymes allone or in combination with DP IV-inhibitors, e.g. the compounds of formulas (1) to (6), and their corresponding pharmaceutically acceptable prodrugs and acid addition salt forms, in pharmaceutical compositions.

7

To prepare the pharmaceutical compositions of this invention, one or more compounds capable of binding to the secondary binding site and/or DP IV-inhibitors or salts thereof of the invention can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using conventional methods known from the art.

The method of treating conditions modulated by the dipeptidyl peptidase IV or dipeptidyl peptidase IV-like enzymes described in the present invention may also b e carried out using a pharmaceutical composition comprising any compound or any combination of the compounds as defined herein and a pharmaceutically acceptable carrier. The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, -polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

EXAMPLES

Example 1

Determination of the Half-life ($t_{1/2}$)

Matrix-assisted laser-desorption ionization time of flight mass spectrometry (MALDI-TOF MS) experiments were carried out at 30° C. at pH 7.6 in 0.1 M Tris/HCl (Sigma-Aldrich, Deisenhofen, Germany) buffer with 25 µM peptide solution. The degradation fate of peptides was measured by monitoring the signal intensity of the pseudomolecular ion peaks of parent peptides and N-terminal shorted peptides versus time when incubated with 40 mU procine DP IV, recombinant human DP IV or serum DP IV activity. The enzyme was preincubated with hexapeptide TFTSDY or TFT-DDY or the heptapeptide H-Ser-D-Glu-Thr-Gly-D-Val-D-Lys-D-Val-OH (15 min, 30° C., 0,016M, 1:1 with DP IV, the concentration of the hexapeptide or the heptapeptide in the reaction mixture was 160 µM). As control served the preincubation of DP IV with 0.01M Tris-buffer (Sigma-Aldrich, Deisenhofen, Germany). The mass spectrometer employed was a Hewlett-Packard G2025 model with a linear time of flight analyzer; samples (4 µL) were mixed 1:1 v/v with matrix (44 mg diammonium-hydrogen-citrate and 30 mg 2',6'-dihydroxyacetophenone in 1 ml aqueous solution containing 50% acetonitrile and 0.05% trifluoroacetic acid; Sigma-Aldrich), transferred to a probe tip and immediately evaporated using the Hewlett-Packard G2024A (Hewlett-Packard, Waldbronn, Germany) sample preparation vacuum chamber. 250 single laser-shot spectra were accumulated. This method of monitoring biodegradation has been validated and allows the general comparison of half-degradation times ($t_{1/2}$) under various conditions.

The $t_{1/2}$-calculation followed this procedure:

The height of the substrate peak was measured and set as 100% at time=0. During the reaction course the sum of substrate and product peak height were set as 100% and the percentage of the remaining substrate peak (also expressed as relative concentration) was determined. Diagrammed relative substrate concentration versus time $t_{1/2}$ can be calculated based on first order exponential decay reaction course.

$$A \xrightarrow{k_1} B$$

$$v = -\frac{d[A]}{d[t]} = k_1 * [A]$$

$$-\int_{A_0}^{A_1} \frac{d[A]}{[A]} = \int_{t_0}^{t} k_1 dt$$

$$[A] = [A]_0 e^{-k_1 t}$$

$$k_1 = \frac{\ln 2}{t_{1/2}}$$

Legend:
A substrate (bioactive peptide)
B product (N-terminal truncated bioactive peptide)
$K_i$ first order rate constant
$K_m$ Michaelis-Menten-constant
$v_i$ initial rate of the reaction
$V_{max}$ maximal rate of the reaction
[S] substrate concentration Example 2

Determination of $K_i$

In order to measure the inhibition constant $K_i$ a photometric assay was used The peptides were measured as competitors of the standard substrate GP-4-Nitroanilide. Three different substrate concentrations (0.4 mM to 0.05 mM) were combined with 8 different competitor concentrations (0.5 mM to 2 µM). The reaction was started by addition of 3.5 nM DP IV. Experiments were carried out under standard conditions: 30° C. in pH 7.6 40 mM HEPES (Sigma-Aldrich) buffer. Nitroaniline production was monitored using a HTS 7000+ microplate reader (PerkinElmer, Überlingen, Germany). The $K_i$-values were calculated via non-linear regression using the enzyme kinetic program Grafit 4.016 (Erithacus Ltd, UK).

For a reversible competitive inhibition is to assumed:

$$v_i = \frac{V_{max} * K_m}{[S] + K_m\left(1 + \frac{[I]}{K_i}\right)}$$

Legend.
[I] inhibitor concentration
$K_i$ inhibition constant

Example 3

MALDI-TOF Approach

In order to investigate directly the influence of the test compounds TFTSDY, TFTDDY and H-Ser-D-Glu-Thr-Gly-D-Val-D-Lys-D-Val-OH on the DP IV-catalyzed peptide hydrolysis the MALDI-TOF assay was used.

As described before (determination of $t_{1/2}$) DP IV and the test compounds were preincubated and the reaction was started by adding the enzyme/hexapeptide mixture to substrate/buffer mix. The control reaction mixture consisted of buffer, enzyme and substrate. From the curves of the first order exponential the initial rate ($v_i$) for the control and the reversible inhibited reaction was calculated.

For the uninfluenced reaction the Michaelis-Menten-equation was used.

$V_i$ was calculated from plotting the relative substrate concentration versus time.

$K_m$ is given, also the substrate concentration.

$$v_i = \frac{V_{max} * K_m}{K_m + [S]}$$

For the reversible inhibited reaction the following reaction was used to calculate $K_i$:

$$v_i = \frac{V_{max} * K_m}{[S] + K_m\left(1 + \frac{[I]}{k_i}\right)}$$

Example 4

Determination of $K_m$

Experiments were carried out with a capillary zone electrophoresis apparatus (MDQ, Beckmann, München, Germany).

The reaction mixture contained 50 µl Gly-Gly (100 mM as standard), 50 µM substrate solved in 0.01 M sodium phosphat buffer (pH 7.6) and 10 µl DP IV (40 mU/ml) stored at 30° C. Six substrate concentrations varying from 1 µM to 60 µM were measured. As running buffer 0.1 M sodium phosphat buffer, pH 2.5 was used. A sample from the reaction mixture was injected with 0.5 psi over 5 s at predefined time points.

Separation was carried out in a capillary with 50 µM inner diameter and 20 cm effective length. The following separation parameters were used:
Separation voltage: 16 kV
Separation time: 12 min
Separation temperature: 25° C.
Detection wave length: 200 nm The maximal rate was calculated by plotting product concentration versus time. The $K_m$-value was calculated transferring the data in the Michaelis-Menten-equation (GraFit 4.0.16, Erithacus Ltd., UK).

Example 5

Expression, Fermentation and Purification of Human DP IV and its Mutant Variants Strains and Plasmid:
P. pastoris strain X-33 and the vector pPICαC were purchased from Invitrogen (USA). E. coli XL-10 cells were provided from Stratagene (USA).

Plasmid Construction and DNA Sequencing.
The DP IV encoding region (Δ1-36) plus $his_6$-tag contained in a pcDNA-3.1 vector was amplified using primers DP IV-21 (TCATCGATGCATCATCATCATCATCAT) and DP IV-22 (TAGGTACCGCTAAGGTAAAGAGAAAC) while implementing the restriction sites for KpnI and BspD1. This fragment was digested with the restriction enzymes KpnI and BspD1 as well as the vector pPCR-ScriptCam (Stratagene, USA), afterwards vector and PCR product were ligated and transformed into the E. coli-strain XL-10. Insertion and orientation was confirmed applying restriction enzyme analysis and partial sequencing. That was followed by excision of the DP IV encoding region from the pPCR-ScriptCam vector with the same restriction enzymes KpnI and BspD1 and its ligation into the Pichia vector p PICαC, which was also treated with the same restriction enzymes before.

Site Directed Mutagenesis:
Single amino acid mutations were carried out with the QuickChange Site-directed Mutagenesis Kit from Stratagene (USA). Following primers were used to introduce the mutations:

```
R310A-DP IV:
DP IV-84  GACATGGGCAACACAAGAAGCAATTTCTTTGCAGTGGC
DP IV-85  GCCACTGCAAAGAAATTGCTTCTTGTGTTGCCCATGTC

R560A-DP IV:
DP IV-73:  GCAGACACTGTCTTCGCACTGAACTGGGCCACTTACC
DP IV-74b: GGTAAGTGGCCCAGTTCAGTGCGAAGACAGTGTCTGC

W629A-DP IV:
DP IV-75: GCAATTTGGGGCTGGTCATAGCGAGGGTACGTAACC
DP IV 76: GGTTACGTACCCTCGCTATGACCAGCCCCAAATTGC.
```

Transformation of P. pastoris X-33:
The vector pPICαC containing the DP IV-variants was linearized using the restriction enzyme Sac I. Transformation was carried out with an electroporation system from BioRad (Germany) according to the Invitrogen Pichia expression kit manual.

Media and Buffers:
YPD, BMMY, and BMGY for shake flask expression were prepared as described in the Invitrogen Pichia expression kit manual using reagents obtained from Difco. Media for fermentation were composed as described in the Invitrogen Pichia fermentation process guidelines using chemicals purchased from Sigma (Deisenhofen, Germany).

Small-scale Expression Studies:
Single colonies were grown in BMGY at 250 rpm, 28° C. overnight. Induction of gene expression was initiated after a media exchange to BMMY. DP IV activity in the expression medium was assayed after 48 hours. Clones displaying highest activity were further monitored in a shaking flask culture (15 ml BMGY and 15 ml BMMY respectively) regarding growth rate and expression rate.

Fermentation:
The clone displaying the highest DP IV activity was used to inoculate 5 ml of BMGY. After 16-18 h of growth at 250 rpm and 28° C. 1 ml of the culture was used to start a 200 ml BMGY flask shake preculture. The cells were grown for 16-18 h at 28° C. A 2 l fermentation was started with the 200 ml inoculum according to the Invitrogen Pichia fermentation process guidelines.

Purification of DP IV:
Expression medium was centrifuged at 40,000*g for 20 minutes to pellet the yeast cells. The supernatant was filtered to remove any residual solids using a 45 µM cellulose acetate filter from Satorius (Germany). Medium was adjusted to pH 7.6 while adding 300 mM NaCl and 50 mM sodium phosphate buffer.

Affinity chromatography was carried out at 4° C. with a Ni-NTA sepharose column (Qiagen, Germany). The column was pre-equilibrated with 300 mM NaCl, 50 mM $NaH_2PO_4$-buffer pH 7.6. The enzyme was eluted with 250 mM imidazole. DP IV assay and SDS-PAGE monitored the purification process. The fractions with the highest DP IV content was further concentrated by ultra-filtration in an Amicon apparatus (cut off 10 kDa) to 0.5 ml.

Gel filtration:
The 0.5 ml ultra-filtrate were applied to a Superdex 200 HiLoad 26/60 column (Pharmacia, Upsalla, Sweden) with a flow rate at 0.25 ml/m in using a 300 mM NaCl, 50 mM $NaH_2PO_4$-buffer pH 7.6 at 4° C. The purification process was monitored via SDS-PAGE and activity assay.

DP IV Assay:
DP IV activity assays were performed spectrofluorimetrically using H-Gly-Pro-AMC (Bachem, Heidelberg, Germany) as substrate and a 0.1M HEPES buffer pH 7.6 plus 0.05M NaCl (Sigma, Deisenhofen, Germany) while monitoring the releasing of AMC by DP IV ($\lambda_{excitation}$=380 nm; $\lambda_{emission}$=460 nm).

SDS-PAGE Analysis:
Proteins were analysed by SDS-PAGE using 12% separating gels with 3% stacking gel. Gels were stained applying Coomassie brilliant blue R-250.

Protein Determination:
Protein concentrations were determined using the BioRad (Germany) Bradford assay kit according to the instructions of the manufacturer.

Western Blot Analysis:
Analytical gel electrophoreses in SDS-polyacrylamid gels were performed according to Laemmli [1] with separation gels containing 12% acrylamide. The separated proteins were transferred to a nitrocellulose membrane (Schleicher & Schuell, Germany) following standard procedures. To detect his-tagged protein a penta-his-tag-antibody and a secondary antibody provided from Qiagen (Germany) (1:2000) was used. Chemo-luminescence was assayed according to the manufacturers protocol (SuperSignal™ West Pico, PIERCE).

Substrates:

All investigated bioactive peptides were obtained from Bachem (Heidelberg, Germany), with exception of glucagon, GIP and its analogs and fragments. These peptides were synthesized at applicant's laboratories.

Example 6

Synthesis of DP IV-Substrates

Glucagon, GIP and the GIP analogs were synthesized with an automated synthesizer SYMPHONY (RAININ) using a modified Fmoc-protocol. Cycles were modified by using double couplings from the 15$^{th}$ amino acid from the C-terminus of the peptide with five-fold excess of Fmoc-amino acids and coupling reagent. The peptide couplings were performed by TBTU/NMM-activation using a 0.23 mmol substituted NovaSyn TGR-resin or the corresponding preloaded Wang-resin at 25 µmol scale. The cleavage from the resin was carried out by a cleavage-cocktail consisting of 94.5% TFA, 2.5% water, 2.5% EDT and 1% TIS.

Analytical and preparative HPLC were performed by using different gradients on the LiChrograph HPLC system of Merck-Hitachi. The gradients were made up from two solvents: (A) 0.1% TFA in $H_2O$ and (B) 0.1% TFA in acetonitrile. Analytical HPLC were performed under the following conditions: solvents were run (1 ml/min) through a 125-4 Nucleosil RP18-column, over a gradient from 5%-50% B over 15 min and then up to 95% B until 20 min, with UV detection ($\lambda$=220 nm). Purification of the peptides was carried out by preparative HPLC on either a 250-20 Nucleosil 100 RP8-column or a 250-10 LiChrospher 300 RP18-column (flow rate 6 ml/min, 220 nm) under various conditions depending on peptide chain length. For the identification of the peptide analogues, laser desorption mass spectrometry was employed using the HP G2025 MALDI-TOF system of Hewlett-Packard.

Example 7

Computer-Assisted Model for Specificity Examinations of Proline-Specific Proteases By means of homology modeling approaches a tertiary-structure-models of human DP IV and porcine DP IV have been developed.

The structure of prolyl oligopeptidase (Fülöp, V., et al. (1998) Prolyl Oligopeptidase: An unusual β-propeller domain regulates proteolysis. Cell 94, 161-170) (Brookhaven Protein Data Bank entry: lqfm) was used as a target to model the structure of DP IV.

COMPOSER (Blundell, T. L.; Sibanda, B. L.; Stemberg, M. J. E.; Thornton, J. M. Knowledge-based prediction of protein structures and the design of novel molecules. *Nature* 1987, 326, 347-352; Blundell, T. L.; Carney, D.; Gardner, S.; Hayes, F.; Howlin, B.; Hubbard, T.; Overington, J.; Singh, D. A.; Sibanda, B. L.; Sutcliffe, M. Knowledge-based protein modelling and design. *Eur. J. Biochem.* 1988, 172, 513-520) a program for homology modeling which is included in the molecular graphics program package SYBYL (TRIPOS Associates Inc., 1699 S. Hanley Road, Suite 303, St. Louis, Mo. 63144) (TRIPOS Associates Inc.) was used to generate the model of DP IV. The amino acid sequences were aligned using the BLOSUM30 matrix (Henikoff, S.; Henikoff, J. G. Amino acid substitution matrices from protein blocks. Proc. Natl. Acad. Sci. USA, (1992), 89, 10915-10919). Afterwards, the modeling procedure consisted of the following steps: structurally conserved regions (SCRs) were identified and a framework of conserved regions was defined as mean positions of structurally equivalent Cα-atoms. Structurally variable regions (SVRs, loops) were selected from a program attached database of peptide fragments in order to satisfy end-to-end distances of the SCRs already positioned in the framework. Loops which could not be formed with this procedure were added manually to complete the structure. The conformations of these loops (mainly in the propeller domain) were determined by simulated annealing techniques in heating the temperature to 700 K and subsequently cooling to 100 K by fixing the remaining part of the structure. This procedure was repeated 30 times. All resulting low temperature structures were minimized using the Kollman all-atom force field (Weiner, S. J.; Kollman, P. A.; Case, D. A.; Singh, U. C.; Ghi, C.; Alagona, G.; Profeta, S.; Weiner, P. A new Force Field for molecular mechanical simulation of nucleic acids and proteins, *J. Am. Chem. Soc.,* 1984, 106, 765-784). Loop conformations with the lowest energy which fulfill all criteria by analyzing the stereo-chemical quality of the protein structure by means of PROCHECK (Laskowski, R. A. et al. (1993) PROCHECK: a program to check the stereochemical quality of protein structures, J. Appl. Cryst. 26, 283-289) were used.

Small molecule ligands such as substrates of the type Xaa-Pro-p-Nitroanilide were docked with the "automatic" docking program GOLD (C. Bissantz, G. Folkers, D. Rognan; J. Med. Chem. 43, 4759-4767, 2000) to the catalytically active site of DP IV to inspect and analyze the principal correctness of the tertiary structure. Ligands such as GIP or glucagon and longer peptides of the GRF family were docked by application of molecular dynamics simulations. These simulations were started to form a random conformation of these compounds, manual positioned at the outer side of the pore formed by the propeller domain. A low force constant between the protonated N-terminus of the ligands and the side chain of Glu668, which is proposed to be the responsible residue for the recognition of the N-terminus of DP IV was added. Molecular dynamics simulations at 300 K for 100 ps using the Kollman all-atom force field were performed by fixing the backbone atoms of DP IV. All these longer peptides reached the catalytically active site (amino acid position S630), showing that ligands are penetrating through the propeller domain to dock to the active site. The resulting docking structures were optimized and subsequently analyzed to define the so called second binding site of DP IV-substrates.

Example 8

Validation of the Computer-assisted Model of DP IV

Glycosylation Sites

The following residues are assumed to be glycosylated and are therefore placed at the surface of the protein: Asn85, Asn92, Asn150, Asn219, Asn229, Asn281, Asn321, Asn520 and Asn685, which are displayed in FIG. 3. All these amino acid residues are accessible except Asn150 and 321, which are slightly buried but may become accessible by thermal moving of the loop region close to this position.

ADA-binding Site

Site directed mutagenesis studies proved that the residues L294, V341 and R343 play an important role in ADA binding to DP IV. Therefore, these residues have to be accessible too. These amino acid residues are displayed in FIG. 3. All these residues are situated at the surface of the protein and interact with ADA.

Binding of Small Inhibitors to the Active Site of DP IV

A number of Xaa-Pyrrolidine and Xaa-Proline dipeptides where docked to DP IV and their preferred interaction with the active site was examined (FIG. 4). One of the most important region is the proline recognition site. In POP this site is formed by the two to three amino acid residues. In analogy to POP the proline binding pocked in DP IV is formed also by two aromatic side chains, the two tyrosine residues Y670 and Y631 and by the hydrophobic residue V711.

The S2-binding site in DP IV must be responsible for the recognition of the protonated and positively charged N-terminus of DP IV ligands and preferred interactions of hydrophobic residues such as Val or Ile. The model shows that the side chain of Glu668 is able to form a salt bridge to the N-terminus of ligands. The recognition of the side chains is realized by interactions with the side chains of two other tyrosine residues (Y211 and Y330) and explains the preferred hydrophobic P2-residues of inhibitors.

Another DP IV-inhibitor, Lys(Z-nitro)-Pyrrolidine, which carries not a completely hydrophobic P2-side chain, was also docked to DP IV. The result is represented in FIG. 5. In the most stable docking arrangement a scorpion like conformation of the Lys-Z-nitro group can be observed, which finally leads to the formation of a strong hydrogen bond to R453. This additional interaction in comparison to usual dipeptide related ligands explains the high affinity and action of this compound.

Substrate Interactions and Aspects of the Catalytic Mechanism

The mode of interaction of substrates to DP IV is shown in FIG. 6. First, the substrates dock exactly in the following conformation: A hydrogen bond is formed between the N-H group and the carbonyl group (torsional angle $\Psi 2 \sim 80°$) of the first amino acid residue (C7-conformation) and the N-terminal amino group is turned out of a $\Psi 1$ torsion of 180° to about 120°. The scissile bond or better plane of the peptide bond to be cleaved is in a perpendicular orientation to the active serine side chain (S630) and allows the reactive attack of the serine to the peptide bond.

Of main importance is the side chain of Y547. The phenolic hydroxyl group forms a hydrogen bond to the carbonyl group of the scissile peptide bond. This interaction plays a very important role in the stabilisation of the tetrahedral intermediate and therefore in the catalytic mechanism in particular in the acylation step. Another interesting finding by Heins et al. (heins et al., Biochim. Biophys. Acta, 1988, 954(2),161-169) was the fact that in the case of proline (in P1) substrates usually the deacylation is the rate limiting step except, when in P2-position an Asp is introduced. A possible docking arrangement of such a substrate is displayed in FIG. 6. The aspartate side chain forms a hydrogen bond to the phenolic OH-group of Y547. This strong interaction prevents the cleaved dipeptide to move out of the binding site and thus shifts the thermodynamic equilibrium and the activation barrier somewhat to the tetrahedral intermediate site and consequently the acylation rate is considerably reduced and becomes rate limiting.

Docking Behavior of Ligands with Biological Importance

It has been demonstrated that the N-terminal nonapeptide of the HIV-tat protein shows inhibitory effects to DP IV. Docking studies of this compound were done with the complete DP IV model as described above. The resulting most stable binding arrangement is shown in FIG. 7.

There are some important interactions. Similar to the already discussed interaction of the substrate Asp-Pro-PNA D2 of Tat forms a hydrogen bond with Y330 and furthermore as seen for Lys-Z-nitro-Pyrrolidine, D5 forms a salt bridge with R453. Further considerable hydrophobic interactions occur between I8 and Y330 and another salt bridge is observed between the C-terminal E9 and R310 of DP IV.

Another similar peptide that was used for docking studies is the N-terminal nonapeptide of the tromboxane receptor (FIG. 8). Similar interactions as seen for HIV-tat were detected. Additionally important is the hydrophobic interaction between W2 and I742.

Example 9

Docking of GIP; VIP and Glucagons to DP IV

Several oligopeptides such as GIP, VIP, glucagon and others are hydrolysed by DP IV and therefore it is clear, that these substrates are docking to DP IV and reaching the active site. Extensive docking investigations by means of molecular dynamics simulations were done using the old model. From these studies the amino acid sequences of the hexapeptides, TFTSDY and TFTDDY and the degradation stabilized heptapeptide H-Ser-D-Glu-Thr-Gly-D-Val-D-Lys-D-Val-OH were derived and its ability to protect oligopeptide substrates from their interaction with a secondary binding site.

Results

The binding and hydrolysis of small dipeptide substrates were only slightly influenced when DP IV was preincubated with the hexapeptides TFTSDY or TFTDDY or the degradation stabilized heptapeptide H-Ser-D-Glu-Thr-Gly-D-Val-D-Lys-D-Val-OH but the affinity of larger oligopeptides such as GIP, VIP, glucagon and others was considerably reduced. These experiments clearly prove the existence of a secondary binding site.

How these rather long peptides reach the active site of DP IV without essential steric hindrance was investigated. GIP was placed at the top of the propeller domain with the N-terminus pointing to the direction middle to DP IV. A small constraint (additional force constant) was placed between the N-terminal nitrogen atom of GIP and a carboxyl oxygen atom of E668. Then a molecular dynamics simulation over 50.000 fs at 300 K was started with fixed backbone atoms of DP IV in the gas phase. Surprisingly it was shown that GIP moved in the pore rapidly without any considerable steric hindrance and was indeed able to reach the active site. Finally starting from the end structure of this "constrained" dynamic model, dynamic simulations with GIP already situated inside DP IV were repeated. The final optimized docking arrangement is shown in FIGS. 9 to 12 and the most important interactions are summarized in Tables 8 to 11.

TABLE 8

Most important interactions of GIP with DP IV

| GIP | DP IV | typ of interaction |
|---|---|---|
| NT | E668 | salt bridge |
| Y1-CO | N710 | H-bond |

TABLE 8-continued

Most important interactions of GIP with DP IV

| GIP | DP IV | typ of interaction |
|---|---|---|
| S2-OH | Y631 | H-bond |
| S2-CO | Y547 | H-bond (Catalysis!) |
| E3 | R560 | salt bridge |
| I7 | Y330 | hydrophob |
| D9 | R310 | salt bridge |
| Y10 | W154 | hydrophob |
| I12 | W157 | hydrophob |
| D15 | K463 (R318) | salt bridge |
| K16 | E464 (E91) | salt bridge |

TABLE 9

Most important interactions of VIP with DP IV

| VIP | DP IV | typ of interaction |
|---|---|---|
| NT | E668 | salt bridge |
| H1-CO | N710 | H-bond |
| H1-side chain | I742 | hydrophob |
| S2-OH | Y631 | H-bond |
| S2-CO | Y547 | H-bond (catalysis!) |
| D3 | R560 | salt bridge |
| D8 | R310 | salt bridge |
| Y10 | W154 | hydrophob |
| Y10-CO | S460 | H-bond |
| K15 | E464 | salt bridge |

TABLE 10

Most important interactions of Glucagon with DP IV

| Glucagon | DP IV | typ of interaction |
|---|---|---|
| NT | E668 | salt bridge |
| H1-CO | N710 | H-bond |
| H1-side chain | I742 | hydrophob |
| A2-CO | Y547 | H-bond |
| Q3 | R560 | H-bond |
| T5 | T152 | H-bond |
| T7 | Y416 | H-bond |
| S8 | Y330 | H-bond |
| D9-CO | Y416 | H-bond |
| D9 | R310 | salt bridge |
| Y10 | W154 | hydrophob |
| Y13 | L90 | hydrophob |
| D15 | R318 | salt bridge |
| R17 | E91 | salt bridge |

TABLE 11

Most important interactions of the
hexapeptide T(5)-F-T-S-D-Y with DP IV

| hexapeptide | DP IV | type of interaction |
|---|---|---|
| T5 | T152 | H-bond |
| T7 | Q153(CO-backbone) | H-bond |
| S8 | S552 | H-bond |
| D9 | R310 | salt bridge |
| Y10 | W154 | hydrophobic |
| Y10(OH) | T152(OH) | H-bond |
| Y10(OH) | T152(CO-backbone) | H-bond |
| Y10(CT) | S460(OH) | H-bond |

As can be seen in FIGS. 9 and 11, GIP is able to reach the active site of DP IV, but the C-terminal tail is still at the surface of the propeller domain.

The scissile peptide bond after Ser2 is exactly in an orientation required for optimal hydrolysis (FIG. 10). A number of important interactions which explain the affinity of GIP to DP IV were detected. These attractive interactions are summarized in Table 6. Interestingly a number of interactions were observed, which were already discussed for other ligands (see above).

Based on these results analogous docking studies were performed with VIP, glucagon and the hexapeptide TFTSDY (FIGS. 12 to 15) The results are summarized by listing the most attractive interactions in Tables 7 to 9.

These results prove that the oligopeptide ligands penetrate through the propeller domain to dock to the active site. Furthermore, some highly attractive interactions between the oligopeptide ligands and DP IV were shown, which explain the affinity of the calculated compounds and which were used to predict the structure of non-peptidic ligands for the secondary binding site of DP IV. Some preliminary structures of such non-peptidic ligands are provided in the description above.

Moreover, the results of these studies confirm the proposed docking of Lys-Z-nitro-Pyrrolidine, e.g. the interaction of the nitro-group with AR560. When the oligopeptide ligands have an Asp in third or fourth position in their amino acid sequence, a salt bridge with R560 is formed. By docking arrangement of the hexapeptide TFTSDY (FIG. 15), it was proven that this hexapeptide indeed prevents binding of oligopeptide ligands to the active site.

Example 10

Preparation of Porcine DP IV

DP IV was purified from porcine kidney. Approximately 2 kg cortex was removed from pig kidneys and cut in small pieces. This tissue material was washed with 0.9% NaCl solution overnight at 4° C. to remove remaining blood. The washed cortex was homogenized using an ultraturrax. During homogenization an equal amount of a 0.02 M sucrose solution containing 0.2% Triton X-100 was added. After homogenization the DP IV-protein was released from the membrane by an 18 h autolysis step at 30° C. Insoluble particles were removed by centrifugation at 15900×g for 30 min. After a first precipitation and centrifugation step (60% $(NH_4)_2SO_4$-saturation, 3 h, room temperature, centrifugation: 39200×g, 30 min) DP IV-activity remains in the supernatant. Second precipitation was conducted overnight at 4° C. and 85% saturation. After centrifugation the DP IV-containing pellet was dissolved in a minimal volume of a 25 mM phosphate buffer, pH 6.8 and dialyzed against 3×2l of this buffer over night. After additional centrifugation (30 min, 39200×g) the solution was concentrated to approximately 45 ml using an Arnicon ultrafiltration cell (cut-off 100 kDa) and again centrifuged at 44000×g. A preparative size exclusion chromatography was used as second purification step. 15 ml of the DP IV-containing solution were applied to a Sepharose 6B (Pharmacia) column (100 cm×2.6 cm) and eluted with the phosphate buffer, pH 6.8. The pooled fractions from 3 runs were further purified by anion exchange chromatography on a DEAE-Sephacel (Pharmacia) column (17 cm×2.5 cm). For binding the 25 mM phosphate buffer pH 6.8 was used and DP IV was eluted with a salt gradient from 39 mM to 150 mM NaCl in 5 column volumes. The final separation step was a high resolution anion exchange chromatography on a Uno Q column (6 ml, BioRad). The DP IV-containing fraction was diluted with an equal volume of $H_2O$ and applied to the column using a 25 mM Bis-Tris buffer pH 6.8. Elution was performed with a NaCl gradient from 0 to 60 mM. Final purification of the naturally glycosylated protein to homogeneity was achieved by preparative isoelectric focusing using the Rotofor system (BioRad). One run of the above procedure yields roughly 60mg of total protein, purified by a factor of approximately 280 and exhibiting a specific activity of always above 42 U/mg.

Example 11

Sequencing of Porcine DP IV cDNA

To obtain the cDNA sequence of porcine DP IV, total RNA was extracted from porcine kidney and RT-PCR was performed as described elsewhere. The sequence was submitted to GenBank (accession number: AY 198323).

Example 12

Synthesis of p-Iodo-Phe-Pyr-CN *TFA

Synthesis of p-Iodo-Phe-Pyr-CN *TFA, an slow-tight binding inhibitor of DP IV was performed according to known chemical protocols (Ashworth, D. M., Atrash, B., Baker, G. R., Baxter, A. J., Jenkins, P. D., Jones, D. M. & Szelke, M. (1996) *Bioorg. Medicinal Chem. Letter* 6, 1163-1166).

Boc-p-Iodo-Phe-Pro-NH$_2$. Triethylamine (163.8 ml, 1.17 mmol) was added to a solution of H-ProNH$_2$*HCl (118.5 mg, 0.782 mmol) in dry DMF (10 ml). Boc-p-Iodo-Phe-OSu (0.42 g, 0.86 mmol) was added in one portion and the mixture stirred for 16 h under an argon atmosphere. The solvent was evaporated and the residue treated in a standard way, i.e. the residue was partitioned between ethylacetate (60 ml) and 0.3N KHSO$_4$ solution (10 ml). The organic layer was further washed with saturated NaCHO$_3$ solution (10 ml), water (10 ml)and brine (5 ml). The solution was dried and evaporated at reduced pressure.

Boc-p-Iodo-Phe-Pyr-CN. Imidazole (38.96 mg, 0.572 mmol) was added to a solution of Boc-p-Iodo-Phe-Pro-NH$_2$ in dry pyridine (5 ml) under an argon atmosphere. The solution was cooled to −35° C., before the dropwise addition of POCl$_3$ (0.105 ml, 1.13 mmol). The reaction was stirred at −30° C.—to −20° C. for 60 min. The solution was then evaporated and the crude residue subjected to column chromatography (silica gel) to yield 180 mg (94%) of 2-(S)-cyano-1-[tert-(butoxycarbonyl)(p-Iodo-phenylalanyl)-pyrrolidine as a colourless oil.

p-Iodo-Phe-Pyr-CN *TFA. Deprotection was carried out by stirring with trifluoro acetic acid for 60min. Evaporation and lyophilisation from water afforded 82.7 mg of 2-(S)cyano-1-(p-Iodo-phenylalanyl)pyrrolidine as a white solid.

ESI-MS: calculated 369.0, found (M+H)$^+$=370.0

$^1$H-NMR: (D$_2$O), d (ppm): 1.55-1.61 (m, 1H), 1.7-1.82 (m, 1H), 1.91-2.19 (m, 2H), 2.49-2.62 (m, 1H), 2.89-3.09 (m, 1H), 3.19-3.21 (m, 1H), 3.21-3.34 (m, 1H), 4.31-4.39 (m, 1H), 4.61-4.69 (m, 4H), 6.91-7.00 (m, 2H), 7.60-7.71 (m, 2H)

$^{13}$C-NMR: (D$_2$O), d (ppm); 167.832, 131.656, 118.055, 93.173, 65.934, 52.250, 47.061, 46.428, 36.322, 29154, 24.063, Example 13

Crystallization and Crystal Transformation

Triclinic crystals were obtained at room temperature within several days by mixing equal volumes of protein at concentration of 20 mg/ml with the reservoir solution (20-22% PEG2K, 0.1 M ammonium sulfate, and 0.1 M Tris/HCl pH 8.0) using the sitting drop vapor diffusion method. The crystals were very sensitive towards manual handling and oxygen. Opening of the crystallization vials led to protein precipitation which was only partly reversible. These problems were solved by piercing the cover tape of the crystallization plates with a syringe and immediate covering of the crystallization drop with perfluoropolyether (PFPE) oil. By harvesting the crystals using a loop with humidity control most of the surrounding mother liquor gets replaced with the PFPE oil. Crystals were mounted on an in-house rotating anode. Crystals initially diffracted very weakly, typically below 10 Å. The humidity was then ramped down from 96.5% to 86.5% using a gradient of 0.5% (150 s)$^{-1}$ which induced a phase transition in the crystalline lattice order reflected by a dramatically improved diffraction pattern. At an optimal relative humidity crystals were flash frozen in the cold nitrogen stream and transported to the synchrotron for data collection. For ligand complex studies, DP IV-crystals were soaked with the inhibitor prior to the crystal transformation procedure. Data were processed and scaled using DENZO and SCALEPACK (Otwinowski, Z. & Minor, W. (1997) in *Meth. Enzym.*, eds. Carter, C. W. J. & Sweet, R. M. (Academic Press, Vol. 276, pp.307-326.).

Example 14
Structure Determination

The structure was determined by multiple wavelength anomalous dispersion (MAD) using a mercury derivative and subsequent non-crystallographic symmetry (NCS) electron density averaging. Briefly, local two-fold axes were determined by using the program GLRF (Tong, L. & Rossmann, M. G. (1990) *Acta Cryst. A*46, 783-792.). Next, a local Harker section perpendicular to the molecular dimer axis was cut out of the three-dimensional anomalous Patterson map using the program MAIN (Turk, D. (1992) in *Chemistry* (Technische Universität, München.), averaged along the orthogonal local two-fold axes, and subsequently input to RSPS (Knight, S. D. (2000) *Acta Cryst. D*52, 42-47) for automatic local doublet sites detection. We estimate this procedure to enhance the signal to noise ratio for about 50-100fold. The relative position of the two symmetry-related Hg-doublets was determined by translational search (Knight, S. D. (2000) *Acta Cryst. D*52, 42-47). By construction, the resulting sites follow the local symmetry and determine the translational NCS parameters. After heavy atom refinement and phasing (program MLPHARE) and solvent flipping (SOLOMON) (Collaborative Computational Project Number 4 (1994) *Acta Cryst. D*50, 760-763; Abrahams, J. P. & Leslie, A. G. W. (1996) *Acta Cryst. D*52, 30-42.), phases were extended to 2.0 Å resolution by NCS averaging using the program MAIN (Turk, D. (1992) in *Chemistry* (Technische Universität, Munchen.) which rendered the electron density readily interpretable, FIG. 25.

Model Building and Refinement.

Using the program MAIN, we placed the catalytic domain of POP in the electron density which served as a jump start in model building and sequence assignment of the DP IV-structure. The model was refined by using the program CNS (Brünger, A. T., Adams, P. D., Clore, G. M., Delano, W. L., Gros, P., Grossekunstleve, R. W., Jiang, J. S., Kuszewski, J., Nilges, M., Pannu, N. S., Read, R. J., Rice, L. M., Simonson, T. & Warren, G. L. (1998) *Acta Cryst*. D54, 905-921.) with current R-values of 21.7% (working set) and 24.9% (test set) and deviations from ideality of 0.008 Å (bond length) and 1.4 degree (angle deviation).

What is claimed is:

1. A method for the treatment of metabolic diseases in a mammal comprising co-administration to said mammal of (i) a compound which binds to a secondary binding site of DPIV and (ii) at least one anti-diabetic agent; wherein the compound is, TFTDDY (SEQ ID NO:4), H-Ser-D-Glu-Thr-Gly-D-Val-D-Lys-D-Val-OH, or a compound of formulas a), b), c) or d):

(a)
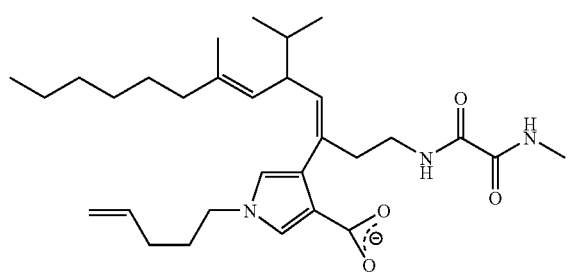

(b)
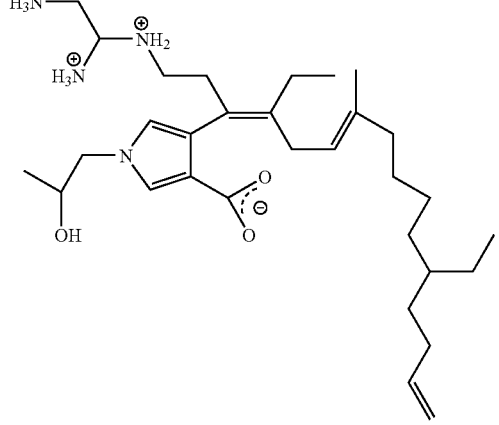

(c)
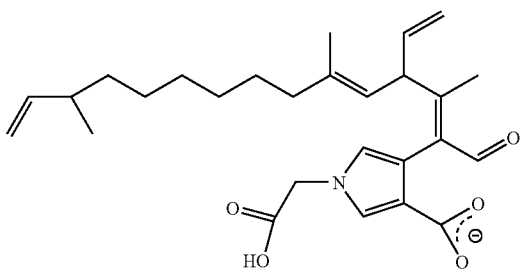

(d)
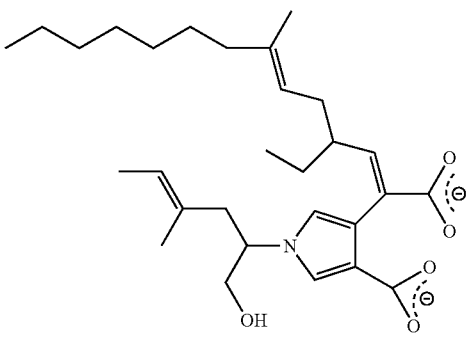

2. A method for the treatment of metabolic diseases in a mammal comprising co-administration to said mammal of (i) a compound which binds to a secondary binding site of DPIV and (ii) at least one anti-diabetic agent selected from the group consisting of:

DP IV inhibitors;
PPAR agonists;
biguanides such as metformin, phenformin or buformin;
protein tyrosine phosphatase-1B (PTP-1B) inhibitors;
insulin and insulin mimetics;
sulfonylureas and other insulin secretagogues;
α-glucosidase inhibitors or acarbose;
glucagon receptor agonists;

GLP-1, GLP-1 mimetics, and GLP-1 receptor agonists;
GLP-2, GLP-2 mimetics, and GLP-2 receptor agonists or teduglutide;
exendin-4, exendin-4 mimetics, exenatide;
GIP, GIP mimetics, and GIP receptor agonists;
PACAP, PACAP mimetics, and PACAP receptor 3 agonists;
PYY, PYY mimetics, PYY receptor agonists, and PYY receptor antagonists;
one or more cholesterol lowering agents selected from the group consisting of:
    HMG-CoA reductase inhibitors,
    sequestrants,
    nicotinyl alkohol, nicotinic acid and salts thereof,
    PPARα agonists,
    PPARγ agonists,
    PPARα/γ dual agonists,
    inhibitors of cholesterol absorption,
    acyl CoA:cholesterol acyltransferase inhibitors, and
    antioxidants;
PPARδ agonists;
anti-obesity compounds;
an ileal bile acid transporter inhibitor; and
anti-inflammatory agents;
wherein the compound is, TFTDDY (SEQ ID NO:4), H-Ser-D-Glu-Thr-Gly-D-Val-D-Lys-D-Val-OH, or a compound of formulas a), b), c) or d):

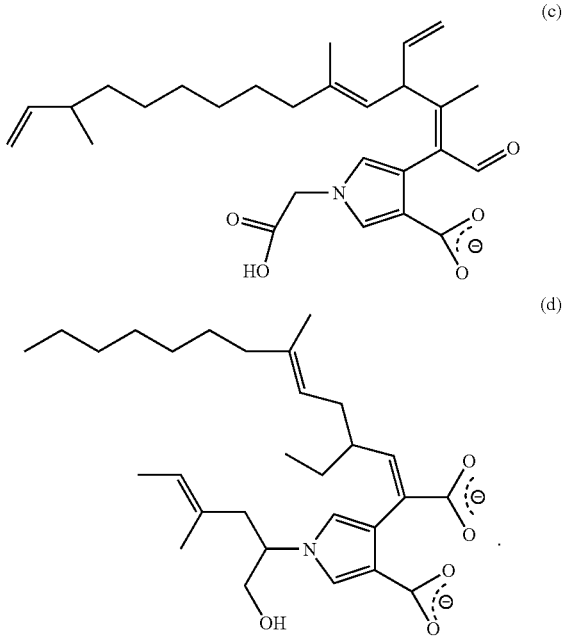

3. The treatment method according to claim 1 wherein the compound is selected from the group comprising: a consensus sequence of the GRF-peptide family, TFTDDY (SEQ ID NO:4), H-Ser-D-Glu-Thr-Gly-D-Val-D-Lys-D-Val-OH, and compounds of formulas a) to d):

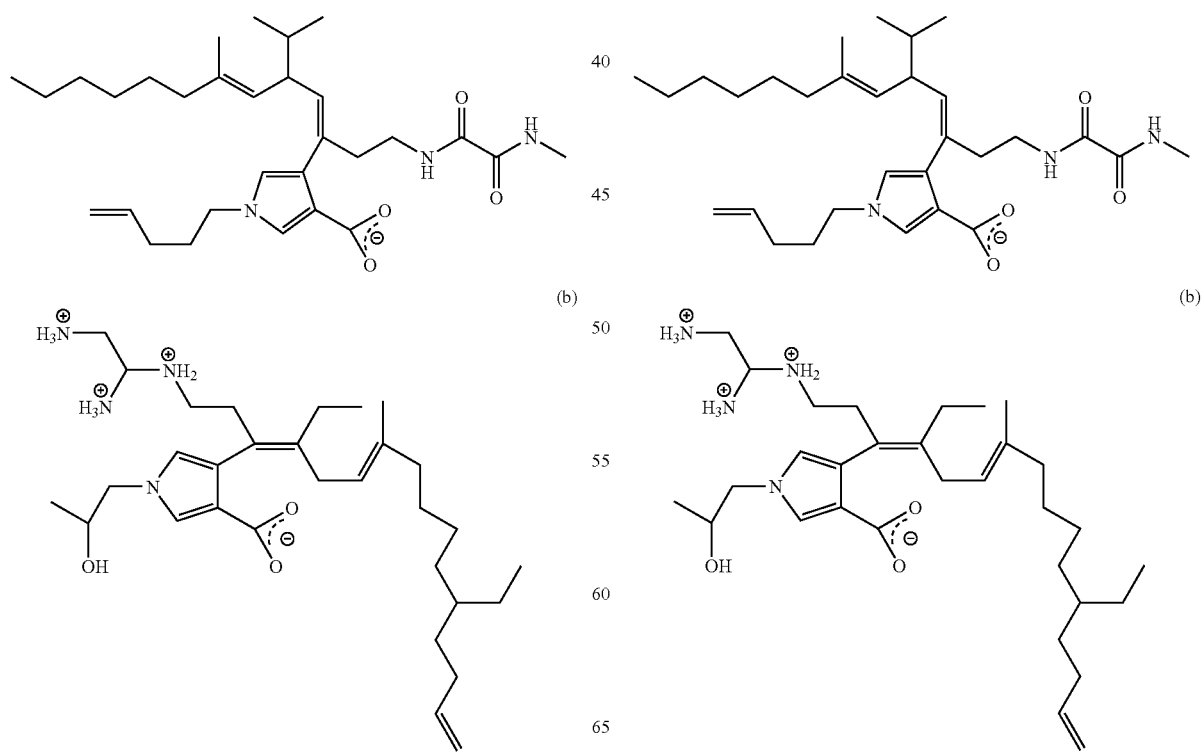

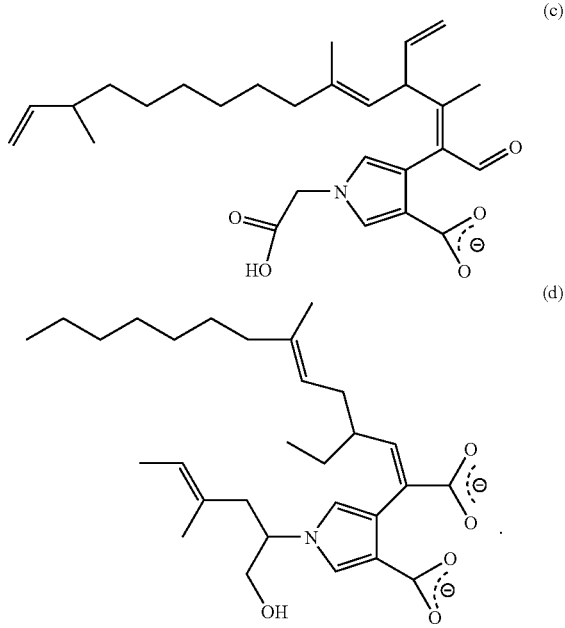

4. The treatment method according to claim 1 wherein the anti-diabetic agent is selected from DPIV inhibitors, metformin, exenatide, exendin-4, acarbose, insulin, and sulfonylureas.

5. The treatment method according to claim 1 wherein the metabolic disease is selected from Syndrome X, impaired glucose tolerance, glucosuria, lipid disorders, dyslipidemia, hyperlipidemia, hypertriglyceridemia, hypercholesterolemia, low HDL levels, high LDL levels, metabolic acidosis, hyperglycemia, diabetes mellitus, diabetic neuropathy and nephropathy and of sequelae caused by diabetes mellitus in mammals, metabolism-related hypertension and cardiovascular sequelae caused by hypertension in mammals.

6. The treatment method according to claim 1 wherein the compound blocks the product release site of DP IV.

7. The treatment method according to claim 1 wherein the compound prevents the tetramerization of DP IV.

8. The treatment method according to claim 1 wherein the compound comprises 3 to 20 amino acid residues.

9. The treatment method according to claim 1 wherein the compound comprises 5 to 12 amino acid residues.

10. The treatment method according to claim 1 wherein the compound comprises 5 to 7 amino acid residues.

11. A pharmaceutical composition comprising a compound which binds to a secondary binding site of DP IV, at least one anti-diabetic agent and a pharmaceutically acceptable carrier therefore.

12. The pharmaceutical composition of claim 11 wherein said at least one anti-diabetic agent is selected from the group consisting of:
DP IV inhibitors;
PPAR agonists;
biguanides such as metformin, phenformin or buformin;
protein tyrosine phosphatase-1B (PTP-1B) inhibitors;
insulin and insulin mimetics;
sulfonylureas and other insulin secretagogues;
α-glucosidase inhibitors or acarbose;
glucagon receptor agonists;
GLP-1, GLP-1 mimetics, and GLP-1 receptor agonists;
GLP-2, GLP-2 mimetics, and GLP-2 receptor agonists or teduglutide;
exendin-4, exendin-4 mimetics, exenatide;
GIP, GIP mimetics, and GIP receptor agonists;
PACAP, PACAP mimetics, and PACAP receptor 3 agonists;
PYY, PYY mimetics, PYY receptor agonists, and PYY receptor antagonists;
one or more cholesterol lowering agents selected from the group consisting of:
HMG-CoA reductase inhibitors,
sequestrants,
nicotinyl alkohol, nicotinic acid and salts thereof,
PPARα agonists,
PPARγ agonists,
PPARα/γ dual agonists,
inhibitors of cholesterol absorption,
acyl CoA:cholesterol acyltransferase inhibitors, and
antioxidants;
PPARδ agonists;
anti-obesity compounds;
an ileal bile acid transporter inhibitor; and
anti-inflammatory agents.

13. The pharmaceutical composition of claim 11 wherein said compound is TFTDDY (SEQ ID NO:4).

14. The pharmaceutical composition of claim 11 wherein said compound is H-Ser-D-Glu-Thr-Gly-D-Val-D-Lys-D-Val-OH.

15. The pharmaceutical composition of claim 11 wherein said compound which binds to a secondary binding site of DP IV and/or DP IV-like enzymes modulates the selectivity and/or activity of DP IV in a mammal.

16. The pharmaceutical composition of claim 11 wherein said compound which binds to a secondary binding site of DP IV and/or DP IV-like enzymes substantially prevents the interaction of DPIV with their binding proteins in a mammal.

17. The pharmaceutical composition of claim 11 wherein said secondary binding site of DPIV comprises the amino acid residues L90, E91, T152, W154, W157, R310, Y330, R318, Y416, S460, K463, E464 and R560 of DP IV.

18. The pharmaceutical composition of claim 11 wherein said secondary binding site of DPIV comprises the amino acid residues Glu361 and Ile407 and Nε2 of His363 of DP IV.

* * * * *